United States Patent [19]
Upasani et al.

[11] Patent Number: 6,143,736
[45] Date of Patent: Nov. 7, 2000

[54] METHODS, COMPOSITIONS, AND COMPOUNDS FOR ALLOSTERIC MODULATION OF THE GABA RECEPTOR BY MEMBERS OF THE ANDROSTANE AND PREGNANE SERIES

[75] Inventors: Ravindra B. Upasani; Haiji Xia, both of Foothill Ranch; Derk Hogenkamp, Carlsbad, all of Calif.

[73] Assignee: CoCensys, Inc., Irvine, Calif.

[21] Appl. No.: 09/349,902

[22] Filed: Jul. 8, 1999

Related U.S. Application Data

[62] Division of application No. 08/887,229, Jul. 2, 1997, Pat. No. 5,939,545, which is a continuation of application No. 08/389,820, Feb. 14, 1995, abandoned, which is a continuation-in-part of application No. 08/346,927, Nov. 23, 1994, abandoned, which is a continuation-in-part of application No. 08/196,919, Feb. 14, 1994, abandoned.

[51] Int. Cl.[7] .............................. A61K 31/56; C07J 41/00; C07J 5/00
[52] U.S. Cl. .......................... 514/169; 514/172; 514/176; 514/177; 514/178; 514/179; 514/180; 514/181; 514/182; 514/816; 514/817; 514/818; 514/899; 552/600; 540/106; 540/107; 540/108; 540/110
[58] Field of Search ................................... 514/169, 172, 514/176, 177, 178, 179, 180, 181, 182; 540/106, 107, 108, 110; 552/600

[56] References Cited

U.S. PATENT DOCUMENTS

| | | | |
|---|---|---|---|
| 3,274,179 | 9/1966 | Christensen | 260/239.55 |
| 3,983,111 | 9/1976 | Phillipps et al. | 260/239.5 |
| 4,898,694 | 2/1990 | Schwartz et al. | 260/397.5 |
| 5,120,723 | 6/1992 | Gee et al. | 514/176 |
| 5,208,227 | 5/1993 | Gee et al. | 514/172 |
| 5,232,917 | 8/1993 | Bolger et al. | 514/176 |
| 5,319,115 | 6/1994 | Tahir et al. | 552/609 |
| 5,359,054 | 10/1994 | Ottow et al. | 540/4 |
| 5,359,055 | 10/1994 | Tsuji et al. | 540/4 |

FOREIGN PATENT DOCUMENTS

| | | |
|---|---|---|
| 1 430 942 | 5/1972 | United Kingdom. |
| WO 93/03732 | 3/1993 | WIPO. |
| WO 93/05786 | 4/1993 | WIPO. |
| WO 93/18053 | 9/1993 | WIPO. |
| WO 94/27608 | 12/1994 | WIPO. |

OTHER PUBLICATIONS

Aird, R.B. and Gordan, G.S., "Anticonvulsive Properties of Desoxycorticosterone," *J. Amer. Med. Assoc.* 145:715–719 (1951).

Arafat et al., "Sedative and hypnotic effects of oral administration of micronized progesterone may be mediated through its metabolites," *Am. J. Obstet. Gynecol.* 159:1203–1209 (1988).

Bäckström et al., "Endocrinological Aspects of Cyclical Mood Changes During the Menstrual Cycle or the Premenstrual Syndrome," *J. Psychosom. Obstet. Gynaecol.* 2:8–20 (1983).

Bäckström et al., "Ovarian Steroid Hormones—Effects on mood, behaviour and brain excitability," *Acta Obstet. Gynecol. Scand. Suppl.* 130:19–24 (1985).

Belelli et al., "Anticonvulsant Profile of the Progesterone Metabolite 5–α–pregnan–3–α–ol–20–one," *Eur. J. Pharmacol.* 166:325–329 (1989).

Bodor, N., "Novel Approaches in Prodrug Design," *Drugs of the Future* 6:165–182 (1981).

Callachan et al., "Modulation of the $GABA_A$ receptor by progesterone metabolites," *Proc. R. Soc. Lond.* B 231 359–369 (1987).

Conney et al., "Decreased Central Depressant Effect of Progesterone and other Steroids in Rats Pretreated with Drugs and Insecticides," *J. Pharmacol. Exp. Ther.* 154:310–318 (1966).

Dennerstein et al., "Progesterone and the premenstrual syndrome: a double blind crossover trial," *British Med. J.* 290:1617–1621 (1985).

Gee, K.W. and Yamamura, H.I., "Benzodiazepines and Barbiturates: Drugs for the Treatment of Anxiety, Insomnia, and Seizure Disorders," in: Drugs in Central Nervous System Disorders, D.C. Horwell, ed., pp. 123–147 (1985).

Gee et al., "GABA–Dependent Modulation of the Cl⁻Ionophore by Steroids in Rat Brain," *Eur. J. Pharmacol.* 136:419–423 (1987).

Gee et al., "Modulation of the Chloride Ionophore by Benzodiazepine Receptor Ligands: Influence of γ–Aminobutyric Acid and Ligand Efficacy," *Molec. Pharmacol.* 30:218–225 (1986).

Gyermek, L., "Pregnanolone: A Highly Potent, Naturally Occurring Hypnotic–Anesthetic Agent," *Proc. Soc. Exper. Biol. Med.* 125:1058–1062 (1967).

Gyermek et al., "Structure–Activity Relationship of Some Steroidal Hypnotic Agents," *J. Med. Chem.* 11:117–125 (1968).

Harrison et al., "Structure–Activity Relationships for Steroid Interaction with the γ–Aminobutyric $Acid_A$ Receptor Complex," *J. Pharmacol. Exp. Ther.* 241:346–353 (1987).

Horwell et al., "A Facile Method to Append Peptidal Side–Chains onto Steroidal Templates," *Tetrahedron Lett.* 50:4225–4234 (Mar. 1994).

Jacobsen et al., "Novel 21–aminosteroids that inhibit iron–dependent lipid peroxidation and protect against central nervous system trauma," *J. Med. Chem.* 33:1145–1151 (1990).

(List continued on next page.)

*Primary Examiner*—Jose' G. Dees
*Assistant Examiner*—Barbara Badio
*Attorney, Agent, or Firm*—Sterne, Kessler, Goldstein & Fox P.L.L.C.

[57] ABSTRACT

Methods, compositions, and compounds for modulating the $GABA_A$ receptor-chloride ionophore complex to alleviate stress, anxiety, seizures, mood disorders, PMS and PND and to induce anesthesia.

35 Claims, 11 Drawing Sheets

OTHER PUBLICATIONS

Laidlaw, J., "Catamenial Epilepsy," *The Lancet*, pp. 1235–1237 (Dec. 15, 1956).

Lambert et al., "Actions of synthetic and endogenous steroids on the $GABA_A$ receptor," *Trends in Pharm. Sci. 8:*224–227 (1987).

Lawrence et al., "Benzodiazepine Anticonvulsant Action: γ–Aminobutyric Acid–Dependent Modulation of the Chloride Ionophore," *Biochem. Biophys. Res. Comm. 123:*1130–1137 (1984).

Lloyd, K.G. and Morselli, P.L., "Psychopharmacology of GABAergic Drugs," in: Psychopharmacology: The Third Generation of Progress, H.Y. Meltzer (ed.), Raven Press, NY, pp. 183–195 (1987).

Maddocks et al., "A Double–blind placebo–controlled trial of progesterone vaginal suppositories in the treatment of premenstrual syndrome," *Am. J. Obstet. Gynecol. 154:*573–581 (1986).

Majewska et al., "Steroids and Brain Activity. Essential Dialogue Between Body and Mind," *Biochem. Pharmacol. 36:*3781–3788 (1987).

Majewska et al., "Steroid Hormone Metabolites Are Barbiturate–Like Modulators of the GABA Receptor," *Science 232:*1004–1007 (1986).

Marker et al., "Isolation of epi–Pregnanol–3–one–20 from Human Pregnancy Urine," *J. Amer. Chem. Soc. 59:*616–618 (1937).

Mattson et al., "Medroxyprogesterone Therapy for Catamenial Epilepsy," *Advances in Epileptology*, vol. 15, Porter et al. (eds.), Washington, DC, Sep. 26–30, 1983, Raven Press, NY, pp. 279–282 (1984).

Mendelson et al., "Sleep induction by an adrenal steroid in the rat," *Psychopharmacology 93:*226–229 (1987).

Notari, R.E., "Theory and Practice of Prodrug Kinetics," *Meth. Enzymol. 112:*309–323 (1985).

Pfaff, D.W. and McEwen, B.S., "Actions of Estrogens and Progestins on Nerve Cells," *Science 219:*808–814 (1983).

Phillipps, G.H., "Structure–Activity Relationships in Steroidal Anaesthetics," Mol. Mech. Gen. Anaesth. Glaxo Symposium, pp. 32–47 (1974).

Phillipps, G.H., "Structure–Activity Relationships in Steroidal Anaesthetics," *J. Steroid Biochem. 6:*607–613 (1975).

Phillipps, G.H., "Water–Soluble Steroidal Anaesthetics," *J. Steroid Biochem. 11:*79–86 (1979).

Purdy et al., "Synthesis, Metabolism, and Pharmacological Activity of 3α–Hydroxy Steroids Which Potentiate GABA–Receptor–Mediated Chloride Ion Uptake in Rat Cerebral Cortical Synaptoneurosomes," *J. Med. Chem. 33:*1572–1581 (1990).

Raisinghani et al., "Uptake of Intravenously Administered Progesterone, Pregnanedione and Pregnanolone by the Rat Brain," *Acta Endocrinologica 57:*395–404 (1968).

Rościszewska et al., "Ovarian hormones, anticonvulsant drugs, and seizures during the menstrual cycle in women with epilepsy," *J. Neurol. Neurosurg. Psych. 49:*47–51 (1986).

Squires et al., "[$^{35}$S]t–Butylbicyclophosphorothionate Binds with High Affinity to Brain–Specific Sites Coupled to γ–Aminobutyric Acid–A and Ion Recognition Sites," *Molec. Pharmacol. 23:*326–336 (1983).

Swinyard, E.A. and Woodhead, J.H., "Experimental Detection, Quantification, and Evaluation of Anticonvulsants," in: Antileptic Drugs, Woodbury et al. (eds.), Raven Press, NY, pp. 111–126 (1982).

Wood et al., "In Vitro Characterization of Benzodiazepine Receptor Agonists, Antagonists, Inverse Agonists and Agonist/Antagonists," *J. Pharmacol. Exp. Ther. 231:*572–576 (1984).

Worms et al., "γ–Aminobutyric Acid (GABA) Receptor Stimulation. I. Neuropharmacological Profiles of Progabide (SL 76002) and SL 75102, with Emphasis on their Anticonvulsant Spectra," *J. Pharmacol. Exp. Ther. 220:*660–671 (1982).

European Search Report for Application No. EP 95 91 3478, mailed Nov. 6, 1997.

Supplemental European Search Report for Application No. EP 95 91 3478, mailed Mar. 20, 1998.

METHODS, COMPOSITIONS, AND COMPOUNDS FOR ALLOSTERIC MODULATION OF THE GABA RECEPTOR BY MEMBERS OF THE ANDROSTANE AND PREGNANE SERIES

CROSS REFERENCE TO RELATED APPLICATIONS

This application is a divisional of U.S. application No. 08/887,229, filed Jul. 2, 1997, now U.S. Pat. No. 5,939,545 which is a continuation of U.S. application No. 08/389,829, filed Feb. 14, 1995, now abandoned, which is a continuation-in-part of U.S. application No. 08/346,927, filed Nov. 23, 1994, now abandoned, which is a continuation-in-part of U.S. application No. 08/196,919, filed Feb. 14, 1994, now abandoned, the contents of each of which are fully incorporated by reference herein.

BACKGROUND OF THE INVENTION

The present invention is directed to methods, compositions, and compounds for modulating animal (and human) brain excitability via the gamma-aminobutyric acid A ($GABA_A$) receptor-chloride ionophore complex (GRC). Specifically, the present invention is directed to methods, compositions, and compounds for modulating brain excitability through binding to the neurosteroid receptor site on the GRC.

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −80 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization (change of potential from −80 mV to −50 mV). This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the GRC, the effect on brain excitability is mediated by GABA, a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs (i.e. reduced neuron excitability). In other words, the higher the chloride ion concentration in the neuron, the lower the brain excitability (the level of arousal).

It is well-documented that the GRC is responsible for the mediation of anxiety, seizure activity, and sedation. Thus, GABA and drugs that act like GABA or facilitate the effects of GABA (e.g., the therapeutically useful barbiturates and benzodiazepines (BZs) such as Valium) produce their therapeutically useful effects by interacting with specific regulatory sites on the GRC.

It has also been observed that a series of steroid metabolites interact with the GRC to alter brain excitability (Majewska, M. D. et al., "Steroid hormone metabolites are barbiturate-like modulators of the GABA receptor," *Science* 232:1004–1007 (1986); Harrison, N. L. et al., Structure-activity relationships for steroid interaction with the gamma-aminobutyric acid-A receptor complex," *J. Pharmacol. Exp. Ther.* 241:346–353 (1987)). Prior to the present invention, the therapeutic usefulness of these steroid metabolites was not recognized by workers in the field due to an incomplete understanding of the potency and site of action. Applicants' invention relates in part to a pharmaceutical application of the knowledge gained from a more developed understanding of the potency and site of action of certain steroid compounds.

The ovarian hormone progesterone and its metabolites have been demonstrated to have profound effects on brain excitability (Backstrom, T. et al., "Ovarian steroid hormones: effects on mood, behavior and brain excitability," *Acta Obstet. Gynecol. Scand. Suppl.* 130:19–24 (1985); Pfaff, D. W. and McEwen, B. S., "Actions of estrogens and progestins on nerve cells," *Science* 219:808–814 (1983); Gyermek et al., "Structure activity relationship of some steroidal hypnotic agents," *J. Med. Chem.* 11:117 (1968); Lambert, J. et al., "Actions of synthetic and endogenous steroids on the $GABA_A$ receptor," *Trends Pharmacol.* 8:224–227 (1987)). The levels of progesterone and its metabolites vary with the phases of the menstrual cycle. It has been well documented that progesterone and its metabolites decrease prior to the onset of menses. The monthly recurrence of certain physical symptoms prior to the onset of menses has also been well documented. These symptoms, which have become associated with premenstrual syndrome (PMS) include stress, anxiety, and migraine headaches (Dalton, K., *Premenstrual Syndrome and Progesterone Therapy*, 2nd edition, Chicago: Chicago yearbook, 1984). Patients with PMS have a monthly recurrence of symptoms that are present in premenses and absent in postmenses.

In a similar fashion, a reduction in progesterone has also been temporally correlated with an increase in seizure frequency in female epileptics (i.e., catamenial epilepsy; Laidlaw, J., "Catamenial epilepsy," *Lancet*, 1235–1237 (1956)). A more direct correlation has been observed with a reduction in progesterone metabolites (Rosciszewska et al., "Ovarian hormones, anticonvulsant drugs and seizures during the menstrual cycle in women with epilepsy," *J. Neurol. Neurosurg. Psych.* 49:47–51 (1986)). In addition, for patients with primary generalized petit mal epilepsy, the temporal incidence of seizures has been correlated with the incidence of the symptoms of premenstrual syndrome (Backstrom, T. et al., "Endocrinological aspects of cyclical mood changes during the menstrual cycle or the premenstrual syndrome," *J. Psychosom. Obstet. Gynaecol.* 2:8–20 (1983)). The steroid deoxycorticosterone has been found to be effective in treating patients with epileptic spells correlated with their menstrual cycles (Aird, R. B. and Gordan, G., "Anticonvulsive properties of deoxycorticosterone," *J. Amer. Med. Soc.* 145:715–719 (1951)).

A syndrome also related to low progesterone levels is postnatal depression (PND). Immediately after birth, progesterone levels decrease dramatically leading to the onset of PND. The symptoms of PND range from mild depression to psychosis requiring hospitalization; PND is associated with severe anxiety and irritability. PND-associated depression is not amenable to treatment by classic antidepressants and women experiencing PND show an increased incidence of PMS (Dalton, K., 1984).

Collectively, these observations imply a crucial role for progesterone and deoxycorticosterone and more specifically their metabolites in the homeostatic regulation of brain excitability, which is manifested as an increase in seizure activity or symptoms associated with catamenial epilepsy, PMS, and PND. The correlation between reduced levels of progesterone and the symptoms associated with PMS, PND, and catamenial epilepsy (Backstrom et al., 1983; Dalton, K., 1984) has prompted the use of progesterone in their treatment (Mattson et al., "Medroxyprogesterone therapy of catamenial epilepsy, " in *Advances in epileptology: XVth Epilepsy International Symposium*, Raven Press, New York, 279–282, 1984, and Dalton, K., 1984). However, progesterone is not consistently effective in the treatment of the aforementioned syndromes. For example, no dose-response relationship exists for progesterone in the treatment of PMS (Maddocks, et al., "A double-blind placebo-controlled trial of progesterone vaginal suppositories in the treatment of premenstrual syndrome," *Obstet. Gynecol.* 154:573–581 (1986); Dennerstein, et al., *British Medical Journal,* 290:16–17 (1986)).

The publications and references referred to above and hereafter in this specification are incorporated herein by reference.

SUMMARY OF THE INVENTION

The present invention is directed to methods, compositions, and compounds for modulating brain excitability. More particularly, the invention relates to the use of 3α-hydroxylated steroid derivatives, acting at a newly identified site on the GR complex, to modulate brain excitability in a manner that will alleviate stress, anxiety, insomnia, mood disorders (such as depression) that are amenable to GR-active agents, and seizure activity. Compositions and compounds effective for such treatment are within the scope of the invention.

The compounds used in and forming part of the invention are modulators of the excitability of the central nervous system as mediated by their ability to regulate chloride ion channels associated with the $GABA_A$ receptor complex. Applicants' experiments have established that the compounds used in and of the invention have anticonvulsant and anxiolytic activity similar to the actions of known anxiolytic agents such as the BZs, but act at a distinct site on the GR complex.

The relationship of endogenous metabolites of progesterone to processes associated with reproduction (estrus cycle and pregnancy) is well established (Marker, R. E., Kamm, O., and McGrew, R. V., "Isolation of epi-pregnanol-3-one-20 from human pregnancy urine," *J. Am. Chem. Soc.* 59:616–618 (1937)). Prior to the present invention, however, it was not recognized how to treat disorders by modulating brain excitability through the use of progesterone metabolites amd their derivatives. Therefore, this invention is directed to methods, compositions, and compounds to treat disorders by modulating brain excitability using the compounds of this invention. Representative disorders treated in the present invention are epilepsy, anxiety, pre-menstrual syndrome (PMS), post-natal depression (PND), mood disorders (such as depression) that are amenable to GR-active agents, and insomnia. The compounds of the invention can also be used to induce anesthesia.

BRIEF DESCRIPTION OF THE DRAWINGS

The present invention may be better understood and its advantages appreciated by those skilled in the art by referring to the accompanying drawings wherein.

DETAILED DESCRIPTION OF THE PREFERRED EMBODIMENTS

Figure 1A:
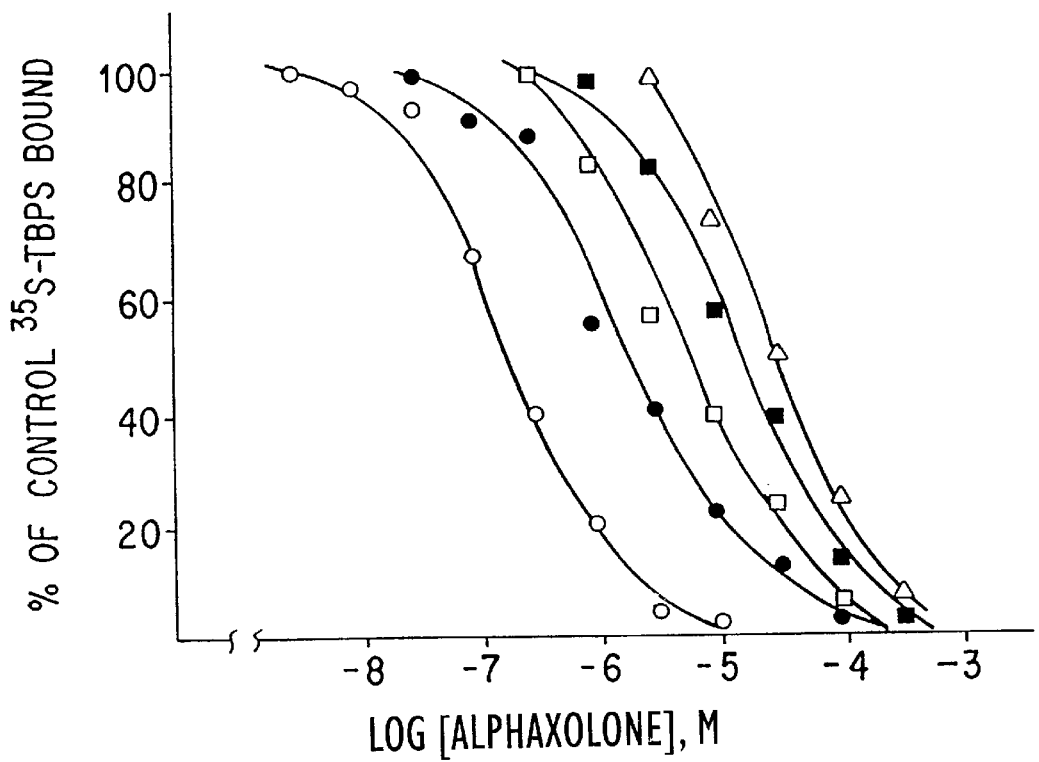
FIGS. 1A and 1B are plots of the percent binding of [$^{35}$S] t-butylbicyclophosphorothionate ([$^{35}$S] TBPS) to the cell membranes of rat brain vs. log concentration of the alphaxalone (also called alfaxalone) and GABA in various concentrations of (+)bicuculline.

The compounds of and used in the invention are derivatives of various 3α-hydroxylated-pregnanes and 3α-hydroxylated-androstanes, and ester, ether, sulfonate, sulfate, phosphonate, phosphate, oxime, thiosulfate, heterocyclic and heteroaryl derivatives thereof, and derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process; see Notari, R. E., "Theory and Practice of Prodrug Kinetics," *Methods in Enzymology,* 112:309–323 (1985); Bodor, N., "Novel Approaches in Prodrug Design," *Drugs of the Future,* 6(3): 165–182 (1981); and Bundgaard, H., "Design of Prodrugs: Bioreversible-Derivatives for Various Functional Groups and Chemical Entities," in *Design of Prodrugs* (H. Bundgaard, ed.), Elsevier, New York (1985). It should be noted that some of the synthetic derivatives forming part of the present invention may not be true prodrugs because, in addition to the above characteristics, they also possess intrinsic activity. However, for purposes of this application they will be referred to as prodrugs.

Our studies (Gee, K. W. et al., "GABA-dependent modulation of the Cl ionophore by steroids in rat brain," *European Journal of Pharmacology*, 136:419–423, 1987) have demonstrated that the 3α-hydroxylated steroids used in the invention are orders of magnitude more potent than others have reported (Majewska, M. D. et al. (1986) and Harrison, N. L. et al. (1987)) as modulators of the GR complex. Majewska et al. and Harrison et al. teach that the 3α-hydroxylated-5-reduced steroids are only capable of much lower levels of effectiveness. Our in vitro and in vivo experimental data demonstrate that the high potency of these steroids allows them to be therapeutically useful in the modulation of brain excitability via the GR complex. The most potent steroids useful in the present invention include derivatives of major metabolites of progesterone and deoxycorticosterone. These steroids can be specifically used to modulate brain excitability in stress, anxiety, insomnia, mood disorders (such as depression) that are amenable to GR-active agents, and seizure disorders in a therapeutically beneficial manner. Furthermore, we have demonstrated that these steroids interact at a unique site on the GR complex which is distinct from other known sites of interaction (i.e., barbiturate, BZ, and GABA) where therapeutically beneficial effects on stress, anxiety, sleep, mood disorders and seizure disorders have been previously elicited (Gee, K. W. and Yamamura, H. I., "Benzodiazepines and Barbiturates: Drugs for the Treatment of Anxiety, Insomnia and Seizure Disorders," in *In Central Nervous System Disorders*, pages 123–147, D. C. Horvell, ed., 1985; Lloyd, K. G. and Morselli, P. L., "Psychopharmacology of GABAergic Drugs," in *Psychopharmacology: The Third Generation of Progress*, pages 183–195, H. Y. Meltzer, ed., Raven Press, N.Y., 1987). These compounds are desirable for their duration, potency and oral activity (along with other forms of administration).

The steroid derivatives of this invention are those having one of the following structural formula (I):

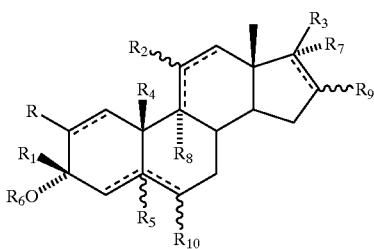

wherein R, $R_1$, $R_2$, $R_3$, $R_4$, $R_5$, $R_6$, $R_7$, $R_8$, $R_9$ and $R_{10}$ are further defined herein and the dotted lines are single or double bonds. The structure having Formula I includes androstanes, pregnanes ($R_4$=methyl), 19-nor-androstanes, and norpregnanes ($R_4$=H).

The present invention also includes pharmaceutically acceptable esters and salts of the compounds of Formula I, including acid addition salts. It is believed that the 3α-hydroxyl may also be masked as a pharmaceutically acceptable ester due to the fact that the ester will be cleaved off as the prodrug is converted to drug form. These are referred to herein as cleavable esters.

Definitions

In accordance with the present invention and as used herein, the following terms are defined with the following meaning, unless explicitly stated otherwise.

The term "alkyl" refers to saturated aliphatic groups including straight chain, branched chain, and cyclic groups, all of which may be optionally substituted. Suitable alkyl groups include methyl, ethyl, and the like, and may be optionally substituted.

The term "alkenyl" refers to unsaturated groups which contain at least one carbon-carbon double bond and includes straight chain, branched chain, and cyclic groups, all of which may be optionally substituted.

The term "alkynyl" refers to unsaturated hydrocarbon groups which contain at least one carbon-carbon triple bond and includes straight chain and branched chain groups which may be optionally substituted. Suitable alkynyl groups include propynyl, pentynyl, and the like which may be optionally substituted with cyano, acetoxy, halo, hydroxy or keto. Preferred alkynyl groups have five to eighteen carbon atoms. More preferred alkynyl groups have five to twelve carbon atoms. Most preferred alkynyl groups have five to seven carbon atoms.

The term "alkoxy" refers to the ether —OR wherein R is alkyl.

The term "aryloxy" refers to the ether —OR wherein R is aryl.

The term "aryl" refers to aromatic groups which have at least one ring having a conjugated pi electron system and includes carbocyclic aryl and biaryl, both of which may be optionally substituted.

The term "carbocyclic aryl" refers to groups wherein the ring atoms on the aromatic ring are carbon atoms. Carbocyclic aryl groups include phenyl and naphthyl groups optionally substituted. Substituted phenyl has preferably one to three, four or five substituents, such being advantageously, lower alkyl, amino, amido, cyano, carboxylate ester, hydroxy, lower alkoxy, halogen, lower acyl, and nitro.

The term "aralkyl" refers to an alkyl group substituted with an aryl group. Suitable aralkyl groups include benzyl, and the like, and may be optionally substituted.

The term "alkanoyloxy" refers to —O—C(O)R, wherein R is alkyl, alkenyl, alkynyl, aryl or aralkyl.

The term "carbalkoxyl" refers to —C(O)OR, wherein R is alkyl, alkenyl, alkynyl, aryl or aralkyl.

The term "carboxamido" refers to —C(O)NRR$_1$, wherein R and R$_1$ are independently selected from hydrogen, alkyl, alkenyl, alkynyl, aryl or aralkyl.

The term "dialkylamino" refers to —NRR" where R and R" are independently lower alkyl groups or together form the rest of a morpholino group. Suitable dialkylamino groups include dimethyl amino, diethylamino, and morpholino.

The term "acyl" refers to the alkanoyl group —C(O)R where R is alkyl, alkenyl, alkynyl, aryl, or aralkyl.

The term "amino" refers to NRR', wherein R and R' are independently hydrogen, lower alkyl or are joined together to give a 5 or 6-membered ring, e.g. pyrrolidine or piperidine rings.

The term "optionally substituted" or "substituted" refers to groups substituted by one to three, four or five substituents, independently selected from lower alkyl (acylic and cyclic), aryl (carboaryl and heteroaryl), alkenyl, alkynyl, alkoxy, halo, haloalkyl (including trihaloalkyl, e.g. trifluoromethyl), amino, mercapto, alkylthio, alkylsulfinyl, alkylsulfonyl, nitro, alkanoyl, alkanoyloxy, alkanoyloxyalkanoyl, alkoxycarboxy, carbalkoxy (—COOR, wherein R is lower alkyl), carboxamido (—CONRR', wherein R and R' are independently lower alkyl), formyl, carboxyl, hydroxy, cyano, azido, keto and cyclic ketals thereof, alkanoylamido, heteroaryloxy, heterocarbocyclicoxy, and hemisuccinate ester salts.

The term "lower" is referred to herein in connection with organic radicals or compounds defines such as one up to and including ten, preferably up to and including six, and advantageously one to four carbon atoms. Such groups may be straight chain, branched chain, or cyclic.

The term "heterocyclic" refers to carbon containing radicals having four, five, six, or seven membered rings and one, two or three O, N or S heteroatoms, e.g., thiazolidine, tetrahydrofuran, 1,4-dioxane, pyrrolidine, piperidine, quinuclidine, dithiane, tetrahydropyran, ε-caprolactone, ε-caprolactam, ω-thiocaprolactam, and morpholine.

The term "heteroaryl" refers to carbon containing 5–14 membered cyclic unsaturated radicals containing one, two, three or four O, N or S atoms and having 6, 10 or 14π electrons delocalized in one or more rings, e.g., pyridine, oxazole, indole, purine, pyrimidine, imidazole, benzimidazole, indazole, 2H-1,2,4-triazole, 1,2,3-triazole, 2H-1,2,3,4-tetrazole, 1H-1,2,3,4-tetrazole, benzotriazole, 1,2,3-triazolo[4,5-b]pyridine, thiazole, isoxazole, pyrazole, quinoline, cytosine, thymine, uracil, adenine, guanine, pyrazine, picolinic acid, picoline, furoic acid, furfural, furyl alcohol, carbazole, 9H-pyrido[3,4-b]indole, isoquinoline, pyrrole, thiophene, furan, 9(10H)-acridone, phenoxazine, and phenothiazine, each of which may be optionally substituted as discussed above.

The term "dioic acids" refers to $C_{1-5}$ alkylene groups substituted with two carboxy groups, for example, malonic acid, succinic acid, glutaric acid, adipic acid, pimelic acid, and suberic acid. Hemi-ester salts of the dioic acids include the sodium, lithium, potassium, magnesium and calcium salts thereof.

The term "β-acetyl-thiosulfate salt" refers is intended to include the sodium, lithium, potassium, magnesium and calcium salts thereof.

The term "pharmaceutically acceptable esters or salts" refers to esters or salts of Formula I derived from the combination of a compound of this invention and an organic or inorganic acid or base.

According to the present invention, ketals include diethers of lower alkanols, e.g. dimethyl and diethyl ketals, as well as cyclic ketals which include diethers of $C_{2-3}$ alkanediols, e.g. ethylene ketals and propylene ketals.

Examples of substituents which can be used in the compounds of Formula I are:

R is hydrogen, halogen, optionally substituted 1-alkynyl, lower alkoxy, alkyl, dialkylamino, or substituted alkyl;

$R_1$ is a substituted aralkynyl, arylalkyl, arylalkenyl, aryl, optionally substituted aralkylalkynyl, alkanoyloxyalkynyl, optionally substituted heteroaryloxyalkynyl, oxoalkynyl or a ketal thereof, cyanoalkynyl, optionally substituted heteroarylalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl;

$R_2$ is hydrogen, hydroxy, alkoxy, alkanoyloxy, carbalkoxyl, a keto group or amino group;

$R_3$ is an acetyl group, a ketal of an acetyl group; an alkoxyacetyl group, an alkylthioacetyl group, an alkylsulfinylacetyl group, an alkylsulfonylacetyl group, an aminoacetyl group, a trifluoroacetyl group; a hydroxyacetyl group; an alkoxyalkylacetyl group, e.g. a methoxymethylacetyl group or an ethoxymethyl-2'-methylene acetyl group; a hydroxyalkyl group, e.g. a hydroxymethyl group, a 1'-hydroxyethyl group, a 1'-hydroxypropyl group, or a 2'-hydroxy-2'-propyl group; a hydroxyacetyl dioic acid hemi-ester salt, e.g. a succinyloxyacetyl group; an alkanoyloxyacetyl group, e.g. an acetoxyacetyl group; or a sulfoxyacetyl group; an alkylacetyl group, e.g. a methylacetyl group; a haloacetyl group; an ethynyl group; an optionally substituted heteroarylacetyl group; an optionally substituted heteroaralkylacetyl group which is also optionally substituted on the alkylene with a hydroxy, alkoxy, alkanoyloxy or carbalkoxyl group; an optionally substituted heterocyclicacetyl group; an acetyl thiosulfate salt; a cyano group; a alkylmethylene group (together with $R_7$); or an alkoxymethylene group (together with $R_7$);

$R_4$ is hydrogen or methyl, $R_5$ is hydrogen;

$R_6$ is hydrogen, alkanoyl, aminocarbonyl, or alkoxycarbonyl;

$R_7$ is hydrogen, halogen, hydroxy, alkoxy, alkanoyloxy, carbalkoxyl, a methylene group (together with $R_3$), or an alkoxymethylene group (together with $R_3$);

$R_8$ is hydrogen or halogen;

$R_9$ is hydrogen, halogen, alkyl, alkoxy, arylalkoxy or amino; and $R_{10}$ is hydrogen, halogen, alkyl, haloalkyl, hydroxy, alkoxy, alkanoyloxy, carbalkoxyl, cyano, thiocyano or mercapto; provided that when $R_3$ is an optionally substituted heteroarylacetyl group or acetylthiosulfate salts or when R is an optionally substituted 1-alkynyl group, then $R_1$ may further be hydrogen, alkyl, alkenyl, aryl, aralkyl, alkynyl, optionally substituted aralkynyl, alkoxyalkyl, aminoalkyl, cyano, cyanoalkyl, thiocyanoalkyl, or azidoalkyl.

A preferred group of compounds of Formula I are compounds where R is hydrogen or lower alkoxy. More preferred are compounds where R, $R_5$, $R_6$, $R_7$, $R_8$, $R_9$ and $R_{10}$ are hydrogen.

Another group of preferred compounds are compounds of Formula I where $R_1$ is substituted aralkynyl, e.g. $R_1$ is 4-substituted phenylalkynyl such as 4-acetylphenylethynyl, 4-methoxyphenylethynyl, 4-N,N-dimethylaminophenylethynyl, 4-cyanophenylethynyl, 4-carboxyphenylethynyl ethyl ester, 4-N,N-dialkylamidophenylethynyl, or where $R_1$ is oxoalkynyl, hydroxyalkynyl, acetoxyalkynyl, cyanoalkynyl, or alkoxyalkynyl.

An additional group of preferred compounds are wherein $R_3$ is acetyl, heteroarylacetyl, heterocyclic-acetyl, hydroxyalkyl, hydroxyacetyl, and their esters with physiologically acceptable acids. More preferably, $R_3$ is acetyl, β-succinyloxyacetyl, alkoxyacetyl, acetylthiosulfate salts, pyrazolylacetyl, or imidazolylacetyl.

An additional group of preferred compounds are wherein:

R is hydrogen, fluoro, chloro or lower alkoxy;

$R_1$ is substituted arylethynyl;

$R_2$ is hydrogen, a keto group or a dimethylamino group;

$R_3$ is a β-acetyl group, a dimethyl ketal of a β-acetyl group, a trifluoroacetyl group, a β-(hydroxyacetyl) group, a β-methoxymethylacetyl group, a β-(ethoxy)methyl-2'-methylene acetyl group, a β-(1'-hydroxyethyl) group, a β-(1'-hydroxypropyl) group, a β-(2'-hydroxy-2'propyl) group, a β-succinyloxyacetyl group, a β-hydroxyacetyl sodium succinate group, a β-acetoxyacetyl group, a β-sulfoxyacetyl group, a β-methylacetyl group, a β-chloroacetyl group, or a β-ethynyl group;

$R_4$ is hydrogen or methyl;

$R_5$, $R_6$, $R_7$, $R_8$, $R_9$ and $R_{10}$ are hydrogen;

the dotted lines all represent single bonds; and $R_7$ is hydrogen or, when $R_3$ is β-hydroxyacetyl, $R_7$ is hydrogen or hydroxy.

Further preferred compounds are compounds of Formula I which are esters of hydroxyl groups at positions 3, 20 and/or 21. Preferred esters are those obtained from their corresponding acids and dioic acids: acetic, propionic, maleic, fumaric, ascorbic, pimelic, succinic, glutaric, bismethylene-salicylic, methanesulfonic, ethane-disulfonic, oxalic, tartaric, salicylic, citric, gluconic, itaconic, glycolic, p-aminobenzoic, aspartic, glutamic, gamma-amino-butyric, α-(2-hydroxyethylamino)propionic, glycine and other α-amino acids, phosphoric, sulfuric, glucuronic, and 1-methyl-1,4-dihydronicotinic.

Preferred are the following compounds: 3α-hydroxy-3β-phenylethynyl-5β-pregnan-20-one, 3α-hydroxy-3β-phenylethynyl-5α-pregnan-20-one, 3α-hydroxy-3β-(3',4'-dimethoxyphenyl)ethynyl-5β-pregnan-20-one, 3α-hydroxy-3β-(4'-methylphenyl)ethynyl-5β-pregnan-20-one, 3α-hydroxy-3β-(2'-methoxyphenyl)ethynyl-5β-pregnan-20-one, 3α-hydroxy-3β-(4'-carboxyphenyl)ethynyl-5β-pregnan-20-one ethyl ester, 3α-hydroxy-3β-(4'-acetoxyacetylpbenyl)ethynyl-5β-pregnan-20-one, 3β-(4'-acetylphenyl)ethynyl-3α-hydroxy-5α-pregnan-20-one, 3β-(4'-acetylphenyl)ethynyl-3α-hydroxy-5β-pregnan-20-one, 3β-(4'-dimethylaminophenyl)ethynyl-3α-hydroxy-5β-pregnan-20-one, 3β-(4'-biphenyl)ethynyl-3α-hydroxy-5β-pregnan-20-one, 3α-hydroxy-3β-(4'-nitrophenyl)ethynyl-5β-pregnan-20-one, 3α-hydroxy-3β-(4'-methoxyphenyl)ethynyl-5β-pregnan-20-one, 3β-(4'-trifluoromethylphenyl)ethynyl-3α-hydroxy-5β-pregnan-20-one, 3β-(4'-chlorophenyl)ethynyl-3α-hydroxy-5β-pregnan-20-one, 3β-(4'-cyanophenyl)ethynyl-3α-hydroxy-5β-pregnan-20-one, 3β-(4'(R/S)-hydroxypentynyl)-3α-hydroxy-5β-pregnan-20-one, 3α-hydroxy-3β-phenyl-5β-pregnan-20-one, 3α-hydroxy-3β-benzyl-5β-pregnan-20-one, 3α-hydroxy-3β-(2'-phenylethyl)-5β-pregnan-20-one, 3α-hydroxy-3β-[2-(3',4'-dimethoxyphenyl)ethyl]-5β-pregnan-20-one, 3α-hydroxy-3β-[6'-oxo-1'-heptynyl]-5β-pregnan-20-one, 3α-hydroxy-3β-(7'-oxo-1'-octynyl)-5β-pregnan-20-one, 3α-hydroxy-3β-(4'-oxo-1'-pentynyl)-5β-pregnan-20-one, 3β-[5'-(R/S)-hydroxyhexynyl]-3α-hydroxy-5β-pregnan-20-one, 3β-(4'-hydroxybutnyl)-3α-hydroxy-5β-pregnan-20-one, 3β-(4'-hydroxybutynyl)-3α-hydroxy-5α-pregnan-20-one, 3α-hydroxy-21-(1'-imidazolyl)-5β-pregnan-20-one, 3α-hydroxy-3β-methyl-21-(1',2',4'-triazolyl)-5α-pregnan-20-one, 3β-(4'-acetoxyphenylethynyl)-3α-hydroxy-5β-pregnan-20-one, 3β-(4'-acetylphenylethynyl)-3α-hydroxy-19-nor-5β-pregnan-20-one, 3β-(4'-carboxyphenylethynyl)-3α-hydroxy-19-nor-5β-pregnan-20-oneethylester, 3β-(4'-carboxyphenylethynyl)-3α-hydroxy-5α-pregnan-20-oneethylester, 3β-[4'-(N,N-diethylcarboxamido)phenyl]ethynyl-3α-hydroxy-5β-pregnan-20-one, 3α-hydroxy-3β-[5-oxo-1-hexynyl]-5β-pregnan-20-one, 3α-hydroxy-3β-[5'-oxo-1'-hexynyl]-5β-pregnan-20-one cyclic 5'-(1,2-ethanediyl acetal), 3β-(5-cyano-1-pentynyl)-3α-hydroxy-5β-pregnan-20-one, 3α-hydroxy-3β-(2-pyridyl)-5β-pregnan-20-one, 3α-hydroxy-3β-(6-hydroxy-1-hexynyl)-3α-hydroxy-5β-pregnan-20-one, 3β-(6'-hydroxy-1'-hexynyl)-3α-hydroxy-5β-pregnan-20-one 6'-hemisuccinate sodium salt, 3β-(5'-hydroxy-1'-pentynyl)-3α-hydroxy-5β-pregnan-20-one, 3β-(5'-hydroxy-1'-pentynyl)-3α-hydroxy-5β-pregnan-20-one 5'-hemisuccinate sodium salt, 3β-(4'-hydroxy-1'-butynyl)-3α-hydroxy-5β-pregnan-20-one 4'-hemisuccinate sodium salt, 3β-(4'-cyano-1'-butynyl)-3α-hydroxy-5β-pregnan-20-one, 3β-(5'-acetoxy-1'-pentynyl)-3α-hydroxy-5β-pregnan-20-one, 3β-(4'-acetoxy-1'-butynyl)-3α-hydroxy-5β-pregnan-20-one, 3β-(4'-acetoxy-1'-butynyl)-3α-hydroxy-5α-pregnan-20-one, 3β-(6'-acetoxy-1'-hexynyl)-3α-hydroxy-5β-pregnan-20-one, 3α-hydroxy-3β-[3-(2'-propynyloxy)-1-propynyl]-5β-pregnan-20-one, 3α-hydroxy-3β-(3-methoxy-1-propynyl)-5β-pregnan-20-one, 3α-hydroxy-3β-(3-methoxy-1-propynyl)-5α-pregnan-20-one, 3α-hydroxy-3β-[3-(4'-pyridinyloxy)-1-propynyl]-5β-pregnan-20-one, 3α-hydroxy-3β-[3-(1'H-1,2,3-triazol-1'-yl)-1-propynyl]-5β-pregnan-20-one, 3α-hydroxy-3β-[3-(2'H-1,2,3-triazol-2'-yl)-1-propynyl]-5β-pregnan-20-one, 3α-hydroxy-3β-(2'-thienyl)ethynyl-5β-pregnan-20-one, 3α-hydroxy-3β-(3'-phenyl-1'-propynyl)-5β-pregnan-20-one, 3α-hydroxy-3β-(3'-phenylpropyl)-5β-pregnan-20-one, 3α-hydroxy-3β-[3-(1'H-pyrazol-1'-yl)-1-propynyl]-5β-pregnan-20-one, 3β-(3'-acetylphenylethynyl)-3α-hydroxy-5β-pregnan-20 -one, 3β-(3'-acetoxy-3'-propynyl)-3α-hydroxy-5β-pregnan-20-one, 3α-hydroxy-3β-(4-hydroxybutyn-1-yl)-21-(1-imidazolyl)-5β-pregnan-20-one, 3α-hydroxy-3β-(4-hydroxybutyn-1-yl)-21-(1-imidazolyl)-5β-19-nor-pregnan-20-one, 3α-hydroxy-3β-(4-hydroxybutyn-1-yl)-21-(1,2,3-triazol-2-yl)-5β-19-norpregnan-20-one, 3α-hydroxy-21-(1-imidazolyl)-5α-pregnan-20-one, sodium S-(3α-hydroxy-3β-methyl-5α-pregnan-20-on-21-yl)thiosulfate, sodium S-(3α-hydroxy-3β-methoxymethyl-5α-pregnan-20-on-21-yl)thiosulfate, sodium S-(3α-hydroxy-5β-pregnan-20-on-21-yl)thiosulfate, sodium S-(3α-hydroxy-3β-trifluoromethyl-5β-pregnan-20-on-21-yl)thiosulfate, sodium S-[3α-hydroxy-3β-(4'-hydroxybutynyl)-5β-pregnan-20-on-21-yl]thiosulfate, sodiumS-(3α-hydroxy-5α-pregnan-20-on-21-yl)thiosulfate, and 3β-(4'-acetylphenylethynyl)-3α,21-dihydroxy-5β-pregnan-20-one, 3β-(4'-acetylphenylethynyl)-3α,21-dihydroxy-5α-pregnan-20-one, 3β-(4'-acetylphenylethynyl)-3α,21-dihydroxy-5β-pregnan-20-one 21-hemisuccinate sodium salt, and 3β-(4'-acetylphenylethynyl)-3α,21-dihydroxy-5α-pregnan-20-one 21-hemisuccinate sodium salt.

The more preferred neuroactive steroids include 3β-(4'acetylphenyl)ethynyl-3α-hydroxy-5α-pregnan-20-one, 3β-(4'-carboxyphenyl)ethynyl-3α-hydroxy-5α-pregnan-20-one ethyl ester, 3β-(4'-acetylphenyl)ethynyl-3α-hydroxy-5β-pregnan-20-one, 3β-(4'-carboxylphenyl)ethynyl-3α-hydroxy-5β-pregnan-20-one ethyl ester, 3β-(4'-acetylphenyl)ethynyl-3α-hydroxy-5β-19-norpregnan-20-one, 3β-(4'-carboxylphenyl)ethynyl-3α-hydroxy-5β-19-norpregnan-20-oneethylester, 3β-(4'-dimethylaminophenyl)ethynyl-3α-hydroxy-5β-pregnan-20-one, 3β-(4'-biphenyl)ethynyl-3α-hydroxy-5β-pregnan-20-one, 3α-hydroxy-3β-(4'-methoxyphenyl)ethynyl-5β-pregnan-20-one, 3β-(4'-trifluoromethylphenyl)ethynyl-3α-hydroxy-5β-pregnan-20-one, 3β-(4'-chlorophenyl)ethynyl-3α-hydroxy-5β-pregnan-20-one, 3β-[4'(R/S)-hydroxypentynyl]-3α-hydroxy-5β-pregnan-20-one, 3β-(4'-hydroxybutynyl)-3α-hydroxy-5β-pregnan-20-one; 3β-(4'-hydroxybutynyl)-3α-hydroxy-5α-pregnan-20-one; 3α-hydroxy-3β-[3-(2'H-1,2,3-triazol-2'-yl)-1-propynyl]-5β-pregnan-20-one; 3α-hydroxy-21-(1-imidazolyl)-5β-pregnan-20-one, 3β-(4'acetylphenylethynyl)-3α,21-dihydroxy-5β-pregnan-20-one, 3β-(4'-acetylphenylethynyl)-3α,21-dihydroxy-5α-pregnan-20-one, 3β-(4'-acetylphenylethynyl)-3α,21-dihydroxy-5β-pregnan-20-one 21-hemisuccinate sodium salt, and 3β-(4'-acetylphenylethynyl)-3α,21-dihydroxy-5α-pregnan-20-one 21-hemisuccinate sodium salt.

The especially preferred neuroactive steroids include 3β-(4'-acetylphenyl)ethynyl-3α-hydroxy-5α-pregnan-20-one, 3β-(4'-acetylphenyl)ethynyl-3α-hydroxy-5β-pregnan-20-one, 3β-(4'-carboxylphenyl)ethynyl-3α-hydroxy-5α-pregnan-20-one ethyl ester, 3β-(4'-carboxylphenyl)ethynyl-3α-hydroxy-5β-pregnan-20-one ethyl ester, 3β-(4'-dimethylaminophenyl)ethynyl-5β-pregnan-20-one, 3β-(4'-biphenyl)ethynyl-3α-hydroxy-5β-pregnan-20-one, 3β-(4'-hydroxybutynyl)-3α-hydroxy-5β-pregnan-20-one 3β-(4'-hydroxybutynyl)-3α-hydroxy-5α-pregnan-20-one; 3α-hydroxy-3β-[3-(2'H-1,2,3-triazol-2'-yl)-1-propynyl]-5β-pregnan-20-one; 3α-hydroxy-21-(1-imidazolyl)-5β-pregnan-20-one, 3β-(4'-acetylphenylethynyl)-3α,21-dihydroxy-5β-pregnan-20-one, 3β-(4'-Acetylphenylethynyl)-3α,21-dihydroxy-5α-pregnan-20-one, 3β-(4'-Acetylphenylethynyl)-3α,21-dihydroxy-5β-pregnan-20-one 21-hemisuccinate sodium salt, 3β-(4'-Acetylphenylethynyl)-3α,21-dihydroxy-5α-pregnan-20-one 21-hemisuccinate sodium salt and 3β-[4'(R/S)-hydroxypentynyl]-3α-hydroxy-5β-pregnan-20-one.

Synthetic Methods

The compounds according to the invention may be prepared by any convenient method, e.g. using conventional techniques such as are described in "Steroid Reactions," Djerassi, published in 1963 by Holden-Day, Inc., San Francisco or "Organic Reactions in Steroid Chemistry", Fried and Edwards, published in 1972 by Van Nostrand-Reinhold Co., New York.

General Methods 20-hydroxy pregnanes were prepared by the reduction of 20-keto pregnanes with conventional reducing agents.

21-Hemisuccinates were prepared from pregnan-20-one derivatives which were first brominated with molecular bromine to obtain the corresponding 21-bromo pregnanes. The bromo compounds were then reacted with various dioic acids, such as succinic acid, in the presence of an amine to yield 21-hydroxy esters. The resulting esters from the dioic acids were then converted to their sodium salts by conventional means.

21-Oxygenated compounds of this type may be prepared by a reaction sequence in which a pregnan-20-one is oxidized with lead tetraacetate to give a 21-acetoxy derivative, hydrolysis of the acetate to give a 21-alcohol, and acylation with an appropriate carboxylic acid derivative, for example, an anhydride or acid chloride or other reagent capable of replacing the hydrogen of the hydroxyl group, such as methanesulfonyl chloride.

Pregn-17-enes may be formed by the reaction of a 17-ketosteroid with a Wittig reagent such as the ylide derived from treatment of a n-propyltriphenylphosphonium bromide with a strong base such as potassium t-butoxide.

EXAMPLE 1

3α-Hydroxy-3β-(2'-phenylethyl)-5β-pregnan-20-one

A solution of 3α-hydroxy-3β-phenylethynyl-5β-pregnan-20-one (44 mg) was dissolved in EtOAc (12 mL), Pd/C (5%, 12 mg) was added and the mixture was hydrogenated at 400 Kpa pressure overnight at rt. Filtration of the catalyst followed by evaporation of the solvent yielded the crude product, which was purified by chromatography over silica gel to isolate the pure title compound (33 mg); mp 153–154° C.; TLC $R_f$ (hexane:acetone 7:3)=0.4.

EXAMPLE 2

3α-(3',4'-Dimethoxyphenylethynyl)-3β-hydroxy-5β-pregnan-20-one and 3β-(3',4'-Dimethoxyphenylethynyl)-3α-hydroxy-5β-pregnan-20-one A solution of 2,2-dibromo-1-(3',4'-dimethoxyphenyl)ethene (prepared by the Wittig reaction of 3,4-dimethoxybenzaldehyde with carbon tetrabromide in the presence of triphenyl phosphine) (966 mg, 3 mmol) in dry THF (15 mL) was treated under $N_2$ with n-BuLi (2.5 M in THF, 6 mmol, 2.4 mL) at −78° C. The mixture was stirred at this temperature for 2 hours and a solution of 5β-pregnan-3,20-dione cyclic 20-(1,2-ethanediyl acetal) (720 mg, 2 mmol) in dry THF (10 mL) was added dropwise over a period of 30 min. After stirring the resulting mixture at −78° C. for 2 hr, the cooling bath was removed and the stirring was continued at rt for another hr. It was then quenched with 2 N HCl solution (1 mL) at −10° C. The solvent was removed and the residue was then dissolved in acetone (25 mL). After adding 2 N HCl (10 mL) the solution was stirred at rt for 2 hr. Sat. $NaHCO_3$ soln. was added to neutralize the acid. The solvents were removed and the residue was extracted with EtOAc. The organic layer was washed with water, dil. $NaHCO_3$ soln., water, and brine. After drying over anhyd. $MgSO_4$ the solution was filtered and evaporated to yield the crude product (1.2 g). This crude product was then dissolved in a small amount of $CH_2Cl_2$ and poured on a column of silica gel. Elution with the toluene:acetone mixture (96:4) gave a phenylacetylene compound, which was not characterized. Further elution with the same solvent yielded 3α-(3',4'-dimethoxyphenylethynyl)-3β-hydroxy-5β-pregnan-20-one (120 mg) as a first fraction, and 3β-(3',4'-dimethoxyphenylethynyl)-3α-hydroxy-5β-pregnan-20-one as a second fraction (430 mg); mp 82–88° C.

An analogous method was used to prepare: 3β-(4'-methoxyphenylethynyl)-3α-hydroxy-5β-pregnan-20-one; 3β-(4'-chlorophenylethynyl)-3α-hydroxy-5β-pregnan-20-one; 3β-(2'-methoxyphenylethynyl)-3α-hydroxy-5β-pregnan-20-one; 3β-(4'-biphenylethynyl)-3α-hydroxy-5β-pregnan-20-one; 3β-(4'-dimethylaminophenylethynyl)-3α-hydroxy-5β-pregnan-20-one; and 3β-(4'-cyanophenylethynyl)-3α-hydroxy-5β-pregnan-20-one.

EXAMPLE 3

3β-(3',4'-Dimethoxyphenylethyl)-3α-hydroxy-5β-pregnan-20-one

A mixture of Pd/C (5%, 28 mg) and EtOAc (12 mL) was presaturated with hydrogen by stirring it under hydrogen for 10 min. A solution of 3β-(3',4'-dimethoxyphenylethynyl)-3α-hydroxy-5β-pregnan-20-one (185 mg) in EtOAc (5 mL) was then added and the mixture was hydrogenated at 300 Kpa pressure overnight at rt. Filtration of the catalyst followed by evaporation of the solvent yielded the crude product, which was purified by chromatography over silica gel (hexane:acetone 4:1) to isolate the pure title compound (135 mg); TLC $R_f$ (hexane:acetone 4:1)=0.14.

EXAMPLE 4

3β-(4'-Nitrophenylethynyl)-3α-hydroxy-5β-pregnan-20-one

A solution of 2,2-dibromo-1-(4-nitrophenyl)ethene (prepared by the Wittig reaction of 4-nitrobenzaldehyde with carbon tetrabromide in the presence of triphenyl phosphine) (296 mg, 1 mmol) in dry THF (20 mL) was treated under $N_2$ with n-BuLi (2.5 M in THF, 2 mmol, 0.8 mL) at −95° C. The mixture was stirred at −80 to −100° C. for 0.5 hr and then a solution of 5β-pregnan-3,20-dione cyclic 20-(1,2-ethanediyl acetal) (120 mg, 0.5 mmol) in dry THF (10 mL) was added dropwise over a period of 10 min. After stirring the resulting mixture at −80° C. for 1 hr, and then at 0° C. for 1 more hr it was quenched with $NH_4Cl$ solution (3 mL). The solvent was removed and the residue was then dissolved in acetone (25 mL). After adding 2 N HCl (10 mL) the solution was stirred at rt for 1 hr. Saturated NaHCO$_3$ soln. was added to neutralize the acid. The solvents were removed and the residue was extracted with CH$_2$Cl$_2$. The organic layer was washed with water, and brine. After drying over anhyd. MgSO$_4$ the solution was filtered and evaporated to yield the crude product (400 mg). This crude product was then dissolved in a small amount of CH$_2$Cl$_2$ and poured on a column of silica get. Elution with toluene:acetone mixture (96:4) gave the title compound as a brown solid (70 mg); TLC R$_f$ (toluene:acetone 95:5)=0.18.

EXAMPLE 5

3β-Hydroxy-3α-phenyl-5β-pregnan-20-one and 3α-hydroxy-3β-phenyl-5β-pregnan-20-one A solution of 5β-pregnan-3,20-dione cyclic 20-(1,2-ethanediyl acetal) (720 mg, 2 mmol) in 15 ml of dry THF was treated with phenyl magnesium bromide (3 M in THF, 6 mmol, 2 mL) at −70° C. After stirring the mixture at this temperature for 3 hr and then at rt for 2 hr, it was quenched with 2 N HCl (1 mL). The solvent was removed and the residue was dissolved in acetone (20 mL). After adding 1 N HCl (5 mL) the solution was stirred at rt for 15 hr. The solvents were removed and the residue was extracted with CH$_2$Cl$_2$. The organic layer was washed with water, dil. NaHCO$_3$ soln., water, and brine. After drying over anhyd. MgSO$_4$ the solution was filtered and evaporated to yield the crude product (1.3 g). This crude product was then dissolved in a small amount of CH$_2$Cl$_2$ and poured on a column of silica gel. Elution with toluene:acetone mixture (95:5) gave a 3α-phenyl-3β-hydroxy-5β-pregnan-20-one (420 mg) as a first fraction. Further elution with the same solvent mixture yielded 3β-phenyl-3α-hydroxy-5β-pregnan-20-one (185 mg), m.p. 182–184° C.

EXAMPLE 6

3β-Hydroxy-3α-benzyl-5β-pregnan-20-one and 3α-hydroxy-3β-benzyl-5β-pregnan-20-one A solution of benzyl magnesium bromide (2 M in THF, 2 mmol, 1 mL) was diluted with THF (15 mL) and was treated dropwise with a solution of 5β-pregnan-3,20-dione cyclic 20-(1,2-ethanediyl acetal) (360 mg, 1 mmol) in dry THF (15 mL) at −60° C. After stirring the mixture at this temperature for 1 hr and then at rt for 15 hr, it was quenched with 2 N HCl (1 mL). The solvent was removed and the residue was dissolved in acetone (20 mL). After adding 1 N HCl (5 mL) the solution was stirred at rt for 30 min. It was neutralized with 2 N NaOH. The precipitated solid was collected by filtration, washed with water and dried to yield 3β-hydroxy-3α-benzyl-5β-pregnan-20- one (238 mg). The filtrate was extracted with EtOAc. The organic layer was washed with water, dil. NaHCO$_3$ soln., water, and brine. After drying over anhyd. MgSO$_4$ the solution was filtered and evaporated to give the crude product (160 mg). This crude product was then dissolved in a small amount of CH$_2$Cl$_2$ and poured on a column of silica gel. Elution with toluene:acetone mixture (95:5) gave 3β-hydroxy-3α-benzyl-5β-pregnan-20-one (40 mg) as a first fraction. Further elution with the same solvent mixture yielded 3α-hydroxy-3β-benzyl-5β-pregnan-20-one (30 mg), which was crystallized from hexane:CH$_2$Cl$_2$ (4:1) as colorless rods (15 mg); m.p. 133–141° C.; TLC R$_f$ (toluene:acetone 9:1)=0.5.

EXAMPLE 7

3β-[3'(R/S)-Hydroxybutynyl]-3α-hydroxy-5β-pregnan-20-one

A solution of 3 (R/S)-hydroxybutyne (0.470 mL, 6 mmol) in dry THF (15 mL) was treated with n-BuLi (2.5 M in THF, 12 mmol, 4.8 mL) at −70° C. After stirring the mixture at this temperature for 0.5 hr, a solution of 5β-pregnan-3,20-dione cyclic 20-(1,2-ethanediyl acetal) (1.08 g, 3 mmol) in dry THF (30 mL) was added and the mixture was stirred at −78° C. for 1 hr. The cooling bath was removed and the mixture was stirred at rt for another 1.5 hr. It was then quenched with NH$_4$Cl solution (3 mL). The solvent was removed and the residue was the dissolved in acetone (10 mL). After adding 2 N HCl (5 mL), the solution was stirred at rt for 1 hr. Saturated NaHCO$_3$ soln. was added to neutralize the acid. The solvents were removed and the residue was extracted with EtOAc. The organic layer was washed with water, dil. NaHCO$_3$ soln., water, and brine. After drying over anhyd. MgSO$_4$ the solution was filtered and evaporated to yield the crude product (1.4 g). This crude product was then dissolved in a small amount of CH$_2$Cl$_2$ and poured on a column of silica gel. Elution with toluene:acetone mixture (85:15 ) gave 3β-[3'(RS)-hydroxybutynyl]-3α-hydroxy-5β-pregnan-20-one (145 mg) as a colorless solid; TLC R$_f$ (toluene:acetone 4:1)=0.24.

An analogous method was used to prepare: 3β-[4'(R/S)-hydroxypentynyl]-3α-hydroxy-5β-pregnan-20-one.

EXAMPLE 8

3β-(4'-Acetylphenylethynyl)-3α-hydroxy-5α-pregnan-20-one

A solution of 4-iodoacetophenone (95 mg, 0.39 mmol), 3β-ethynyl-3α-hydroxy-5α-pregnan-20-one (106 mg, 0.3 mmol) in dry degassed pyrrolidine (3 mL) was stirred under argon at rt. Bis(triphenylphosphine)palladium(II) dichloride (5 mg) and CuI (5 mg) were added and the mixture was stirred at rt for 15 hr. The TLC showed 100% conversion of the starting material, hence, the mixture was quenched with NH$_4$Cl solution (15 mL) and was extracted with EtOAc. The organic layer was washed with water, dil. NaHCO$_3$ soln., water, and brine. After drying over anhyd. MgSO$_4$ the solution was filtered and evaporated to yield the crude product (150 mg). This crude product was then dissolved in a small amount of CH$_2$Cl$_2$ and poured on a column of silica gel. Elution with hexane:acetone mixture (4:1) afforded 3β-(4'-acetylphenylethynyl)-3α-hydroxy-5α-pregnan-20-one (35 mg) as a colorless solid; TLC R$_f$ (hexane:acetone 7:3)=0.4.

An analogous method was used to prepare: 3α-hydroxy-3β-(4'-trifluoromethylphenylethynyl)-5β-pregnan-20-one; 3β-(4'-acetylphenylethynyl)-3α-hydroxy-5β-pregnan-20-one; 3α-hydroxy-3β-(4'-methylphenylethynyl)-5β-pregnan-20-one; 3α-hydroxy-3β-(4'-acetoxyacetylphenylethynyl)-5β-pregnan-20-one; 3β-(3'-hydroxyphenylethynyl)-3α-hydroxy-5β-pregnan-20-one; 3β-(2',4'-difluorophenylethynyl)-3α-hydroxy-5β-pregnan-20-one; 3β-(pentafluorophenylethynyl)-3α-hydroxy-5β-pregnan-20-one; and 3α-hydroxy-3β-(4'-carboxyphenylethynyl)-5β-pregnan-20-one ethyl ester.

EXAMPLE 9

3αHydroxy-21-(1'-imidazolyl)-5β-pregnan-20-one

3α-Hydroxy-21-bromo-5β-pregnan-20-one

To a flask containing a solution of 3α-hydroxy-5β-pregnan-20-one (5.15 g, 16.5 mmol)in methanol (100 mL) was added a solution of bromine (1.1 mL) in methanol (30 mL) dropwise in such a rate to maintain the brown color of the bromine until this color was persistent. Then water (200 mL) was added and the mixture was extracted with CH$_2$Cl$_2$ (3×100 mL). The combined extracts were dried over Na$_2$SO$_4$. Removal of the solvent resulted in the product as a foamy white solid (6.63 g). Other 21-bromo-pregnan-20-ones (3β-ethynyl-3α-hydroxy-21-bromo-5β-pregnan-20-one, 3β-methyl-3α-hydroxy-21-bromo-5α-pregnan-20-one and 3α-hydroxy-3β-trifluoromethyl-12-bromo-5β-19-norpregnan-20-one) were synthesized using the same method.

3α-Hydroxy-21-(1'-imidazolyl)-5β-pregnan-20-one

A mixture of 3α-hydroxy-21-bromo-5β-pregnan-20-one (0.86 g) and imidazole (0.37 g) in CH$_3$CN (12 mL) was heated under Ar to reflux for 1 h and cooled to 25° C. It was then poured into a separatory funnel containing NH$_4$Cl solution (100 mL, aq. sat.) and the product was extracted with EtOAc )3×50 mL). The combined organics were dried over Na$_2$SO$_4$ and the solvent was removed in vacuo. The pure product (0.59 g, 42%) was isolated by flash column chromatography.

The compounds 3α-hydroxy-21-(1'-benzimidazolyl)-5β-pregnan-20-one, 3α-hydroxy-21-[1 H-(4-methyl-5-carbethoxy)imidazol-1-yl)-5β-pregnan-20-one ethylester, 3α-hydroxy-21-(1'-imidazolyl)-5α-pregnan-20-one, 3β-ethynyl-3α-hydroxy-21-(1'-imidazolyl)-5β-pregnan-20-one, 3α-hydroxy-21-(1 H-3,5-dimethylpyrazolyl)-5β-pregnan-20-one, 3α-hydroxy-21-(1'-imidazolyl)-3β-methyl-5α-pregnan-20-one, 3α-hydroxy-21-(1'-pyrazolyl)-5α-pregnan-20-one, 3β-ethynyl-3α-hydroxy-21-(1'-pyrazolyl)-5β-pregnan-20-one, 21-(1'-benzimidazolyl)-3α-hydroxy-3β-methyl-5α-pregnan-20-one, 3α-hydroxy-21-(1'-pyrazolyl)-3β-methyl-5α-pregnan-20-one, 3α-hydroxy-21-(pyrazol-1-yl)-5β-pregnan-20-one, 3α-hydroxy-21-[1 H-(2-methyl)imidazol-1-yl)-5β-pregnan-20-one, 3α-hydroxy-21-[1 H-(2'-formyl)imidazol-1-yl)]-5β-pregnan-20-one, 3α-hydroxy-21-(1 H-imidazol-1-yl)-3β-trifluoromethyl-5β-19-norpregnan-20-one, and 3α-hydroxy-21-(pyrazol-1-yl)-3β-trifluoromethyl-5β-19-norpregnan-20-one were synthesized according to Example 9.

EXAMPLE 10

3α-Hydroxy-3β-methyl-21-(1',2',4'-triazolyl)-5α-pregnan-20one:

To a solution of 1,2,4-triazole (146 mg) in THF (15 mL) under Ar was added NaH (56 mg) and the mixture obtained was stirred at 25° C. for 20 min. Then a solution 3β-methyl-3α-hydroxy-21-bromo-5α-pregnan-20-one (300 mg) in THF was added and the mixture thus obtained was stirred for 5 hr. It was then poured into a separatory funnel containing water (40 mL) and the product was extracted with CH$_2$Cl$_2$ (3×50 mL). The combined organics were dried over Na$_2$So$_4$ and the solvent was removed in vacuo. The pure product (187 mg, 64%) was isolated by flash column chromatography.

3α-Hydroxy-21-(2' H-1,2,3,4-tetrazol-2'-yl)-5β-pregnan-20-one, 3α-hydroxy-21-(2 H-1,2,3-triazol-2-yl)-5β-pregnan-20-one, 3α-hydroxy-21-(9' H-purin-9'-yl)-5β-pregnan-20-one, 3α-hydroxy-3β-methyl-21-(2' H-1',2',3'-triazol-2'-yl)-5α-pregnan-20-one, 3β-ethynyl-3α-hydroxy-21-(1',2',4'-triazolyl)-5β-pregnan-20-one, 3α-hydroxy-3β-methyl-21-(1',2',3'-triazol-1'-yl)-5α-pregnan-20-one, 3α-hydroxy-21-(1',2',4'-triazol-1-yl)-5β-pregnan-20-one, 3α-hydroxy-21-(1' H-1,2,3,4-tetrazol-1'-yl)-5β-pregnan-20-one, 3α-hydroxy-21-[1 H-(4-nitro)imidazol-1-yl)-5β-pregnan-20-one, 3α-hydroxy-21-(7' H-purin-7'-yl)-5β-pregnan-20-one, 3α-hydroxy-21-[1 H-(4',5'-dicyano)imidazol-1-yl)]-5β-pregnan-20-one, 3α-hydroxy-21-(1'-1,2,4-triazol-1-yl)-3β-trifluoromethyl-5β-19-norpregnan-20-one, and 3α-hydroxy-21-[1 H-(4',5'-dichloro)imidazol-1-yl)]-5β-pregnan-20-one, were synthesized according to the procedures set forth in Example 10.

EXAMPLE 11

3β-(4'-Acetoxyphenylethynyl)-3α-hydroxy-5β-pregnan-20-one a. 3β-(4'-Hydroxyphenylethynyl)-3α-hydroxy-5β-pregnan-20-one A solution of 2,2-dibromo-1-(4-hydroxyphenyl)ethene (prepared by the Wittig reaction of 4-hydroxybenzaldehyde with carbon tetrabromide in the presence of triphenyl phosphine) (1.25 mg, 4.5 mmol) in dry THF (25 mL) was treated under N$_2$ with n-BuLi (2.5 M in THF, 13.5 mmol, 5.4 mL) at −70° C. The mixture was then stirred at −70° C. temp. for 0.5 hr, and a solution of 5β-pregnan-3,20-dione, cyclic 20-(1,2-ethanediyl acetal) (810 mg, 2.25 mmol) in dry THF (25 mL) was added dropwise over a period of 10 min. After stirring the resulting mixture at −78° C. for 30 min, the cooling bath was removed and the stirring was continued at rt for another hr. It was then quenched with sat. NH$_4$Cl solution (4 mL) at −10° C. The solvent was removed and the residue was then dissolved in acetone (25 mL). After adding 2 N HCl (6 mL) the solution was stirred at rt for 15 min. Sat. NaHCO$_3$ soln. was added to neutralize the acid. The solvent was removed under reduced pressure and the crude product (1.3 g) was used as such for the next step.

b. 3β-(4'-Acetoxyphenylethynyl)-3α-hydroxy-5β-pregnan-20-one

The crude product from the above step was dissolved in CH$_2$Cl$_2$ (5 mL) and pyridine (3 mL). The resulting solution was added to a ice-cold mixture of acetyl chloride (3 mL) and pyridine (3 mL). The mixture was stirred at 0° C. for 30 min. and was poured into ice (50 g). 2 N HCl (10 mL) was added and the mixture was diluted with more CH$_2$Cl$_2$. The organic layer was separated, washed with water, brine, and dried over anhyd. MgSO$_4$. Removal of solvent gave a crude solid (2 g) which was purified by column chromatography over silica gel. Elution with toluene:acetone mixture (95:5) gave 3α-(4'-acetoxyphenylethynyl)-3β-hydroxy-5β-pregnan-20-one (150 mg). Further elution with the same solvent mixture yielded 3β-(4'-acetoxphenylethynyl)-3α-hydroxy-5β-pregnan-20-one (530 mg); m.p. 171–176° C.; TLC R$_f$ (hexane:acetone 7:3)=0.41.

EXAMPLE 12

3β-(4'-Acetylphenylethynyl)-3α-hydroxy-19-nor-5β-pregnan-20-one

A solution of 4-iodoacetophenone (60 mg, 0.24 mmol), 3β-ethynyl-3α-hydroxy-19-nor-5β-pregnan-20-one (80 mg, 0.24 mmol) in dry degassed triethylamine (0.5 mL) was stirred under argon at 23° C. Bis(triphenylphosphine)-palladium(II)dichloride (5 mg) and CuI (5 mg) were added and the mixture was stirred at this temp. for 45 min. CH$_2$Cl$_2$ (4 mL) was added and the mixture was stirred at 23° C. for 3 hr. The TLC showed 100% conversion of the starting material, hence, the solvent was removed and the residue was purified by chromatography on silica gel. Elution with hexane:acetone (4:1) gave 3β-(4'-acetylphenyl-ethynyl)-3α-hydroxy-19-nor-5β-pregnan-20-one (30 mg) as a colorless solid; mp 65–67° C., TLC R$_f$ (hexane:acetone 4:1)=0.12.

EXAMPLE 13

3β-(4'-Carboxyphenylethynyl)-3α-hydroxy-19-nor-5β-pregnan-20-one ethyl ester

A solution of ethyl 4-iodobenzoate (70 mg, 0.24 mmol) and 3β-ethynyl-3α-hydroxy-19-nor-5β-pregnan-20-one (80 mg, 0.24 mmol) in dry degassed triethylamine (1 mL) was stirred under argon at 23° C. Bis(triphenylphosphine)-palladium(II)dichloride (5 mg) and CuI (5 mg) were added and the mixture was stirred at this temp. for 1 hr. CH$_2$Cl$_2$ (4 mL) was added and the mixture was stirred at 23° C. for 3 hr. The TLC showed 100% conversion of the starting material, hence, the solvent was removed and the residue was purified by chromatography on silica gel. Elution with hexane:acetone (4:1) gave 3β-(4'-carboxyphenylethynyl)-3α-hydroxy-19-nor-5β-pregnan-20-one ethyl ester (22 mg) as a colorless solid; mp 164–166° C., TLC $R_f$ (hexane:acetone 4:1)=0.27.

EXAMPLE 14

3β-(4'-Carboxyphenylethynyl)-3α-hydroxy-5α-pregnan-20-one ethyl ester

A solution of ethyl 4-iodobenzoate (83 mg, 0.3 mmol), 3β-ethynyl-3α-hydroxy-5α-pregnan-20-one (103 mg, 0.3 mmol) in dry degassed triethylamine (1 mL) was stirred under argon at 23° C. Bis(triphenylphosphine)-palladium(II) dichloride (5 mg)and CuI (5 mg) were added and the mixture was stirred at this temp. for 1 hr. $CH_2Cl_2$ (4 mL) was added and the mixture was stirred at 23° C. for 1.5 hr. The TLC showed 100% conversion of the starting material, hence, the solvent was removed and the residue was purified by chromatography on silica gel. Elution with hexane:acetone (4:1) gave 3β-(4'-carboxyphenylethynyl)-3α-hydroxy-5α-pregnan-20-one ethyl ester (10 mg) as a colorless solid; map 190–192° C., TLC $R_f$ (hexane:acetone 4:1)=0.27.

EXAMPLE 15

3β-[4'-(N,N-diethylcarboxamido)phyenyl]ethynyl-3α-hydroxy-5β-pregnan-20-one

A solution of 4-(N,N-diethylcarboxamido)iodobenzene (91 mg, 0.3 mmol), 3β-ethynyl-3α-hydroxy-5β-pregnan-20-one (103 mg, 0.3 mmol) in dry degassed triethylamine (1 mL) was stirred under argon at 23° C. Bis(triphenylphosphine)palladium(II)dichloride (5 mg) and CuI (5 mg) were added and the mixture was stirred at this temp. for 1 hr. $CH_2Cl_2$ (4 mL) was added and the mixture was stirred at 23° C. for 0.5 hr. The TLC showed 100% conversion of the starting material, hence, the solvent was removed and the residue was purified by chromatography on silica gel. Elution with hexane:acetone (3:1) gave 3β-[4'-(N,N-diethylcarboxamido)phenyl]ethynyl-3α-hydroxy-5α-pregnan-20-one ethyl ester (18 mg) as a colorless solid; TLC $R_f$ (hexane:acetone 3:1)=0.22.

EXAMPLE 16

3α-Hydroxy-3β-[5-oxo-1-hexynyl]-5β-pregnan-20-one cyclic (1,2-ethanediyl acetal)

A solution of 1-hexyn-5-one cyclic (1,2-ethanediyl acetal) (493 mg, 3.52 mmol) in dry THF (15 mL) was treated with n-BuLi (2.5 M in THF, 3 mmol, 1.2 mL) at –60° C. After stirring the mixture at –78° C. for 0.5 hr, a solution of 5β-pregnan-3,20-dione, cyclic 20-(1,2-ethanediyl acetal) (360 mg, 1 mmol) in THF (15 mL) was added and the mixture was stirred at –78° C. for 1 hr. The cooling bath was removed and the mixture was quenched with $NH_4Cl$ solution (3 mL). The solvent was removed and the residue was then dissolved in acetone (40 mL). After adding 1 N HCl (4 mL) the solution was stirred at rt for 15 min. Sat. $NaHCO_3$ soln. was added to neutralize the acid. The solvents were removed and the residue was extracted with EtOAc. The organic layer was washed with water, dil. $NaHCO_3$ soln., water, and brine. After drying over anhyd. $MgSO_4$ the solution was filtered and evaporated to yield the crude product (700 mg). This crude product was then dissolved in a small amount of $CH_2Cl_2$ and poured on a column of silica gel. Elution with toluene:acetone mixture (93:7) gave 3α-hydroxy-3β-[5-oxo-1-hexynyl]-5β-pregnan-20-one cyclic (1,2-ethanediyl acetal) (210 mg) as a colorless solid; mp 130–133° C.; TLC $R_f$ (toluene:acetone 9:1)=0.33.

EXAMPLE 17

3α-Hydroxy-3β-[5-oxo-1-hexynyl]-5β-pregnan-20-one

3α-Hydroxy-3β-[5-oxo-1-hexynyl]-5β-pregnan-20-one cyclic (1,2-ethanediyl acetal) (95 mg) was dissolved in acetone (5 mL). After adding 2 N HCl (1 mL) the solution was stirred at rt for 3 hr. Sat. $NaHCO_3$ soln. was added to neutralize the acid. The solvents were removed and the residue was extracted with EtOAc. The organic layer was washed with water, water, and brine. After drying over anhyd. $MgSO_4$ the solution was filtered and evaporated to yield the crude title product (100 mg), which was then crystallized from hexane-acetone as colorless rods, yield 63 mg; mp 104–106° C.; TLC $R_f$ (hexane:acetone 7:3)=0.27.

An analogous method was used to prepare 3α-hydroxy-3β-[6-oxo-1-heptynyl]-5β-pregnan-20-one, using 1-heptyn-6-one cyclic 6-(1,2-ethanediyl acetal).

EXAMPLE 18

3β-(5-Cyano-1-pentynyl)-3α-hydroxy-5β-pregnan-20-one

A solution of 5-cyanopentyne (0.84 mL, 8 mmol) in dry THF (20 mL) was treated with n-BuLi (2.5 M in THF, 7.8 mmol, 3.2 mL) at –70° C. After stirring the mixture at –75° C. for 0.5 hr, a solution of 5β-pregnan-3,20-dione, cyclic 20-(1,2-ethanediyl acetal) (720 mg, 2 mmol) in THF (20 mL) was added and the mixture was stirred at –78° C. for 0.5 hr. The cooling bath was removed and the mixture was quenched with $NH_4Cl$ solution (3 mL). The solvent was removed and the residue was then dissolved in acetone (40 mL). After adding 1 N HCl (4 mL) the solution was stirred at rt for 15 min. Sat. $NaHCO_3$ soln. was added to neutralize the acid. The solvents were removed and the residue was extracted with EtOAc. The organic layer was washed with water, and brine. After drying over anhyd. $MgSO_4$ the solution was filtered and evaporated to yield the crude product (1.55 g). The crude product was then dissolved in a small amount of $CH_2Cl_2$ and poured on a column of silica gel. Elution with toluene:acetone mixture (95:5) gave 3α-(5-cyano-1-pentynyl)-3β-hydroxy-5β-pregnan-20-one (170 mg) as a first fraction. Further elution with the same solvent mixture yielded 3β-(5-cyano-1-pentynyl)-3α-hydroxy-5β-pregnan-20-one (480 mg) as a colorless solid; mp 134–136° C.; TLC $R_f$ (hexane:acetone 7:3)=0.3.

An analogous method was used to prepare 3β-(4-cyano-1-butynyl)-3α-hydroxy-5β-pregnan-20-one.

EXAMPLE 19

3α-Hydroxy-3β-(2-pyridyl)ethynyl-5β-pregnan-20-one

A solution of 2-ethynylpyridine (270 mg, 2.6 mmol) in dry THF (15 mL) was treated with n-BuLi (2.5 M in THF, 2.5 mmol, 1 mL) at –60° C. After stirring the mixture at –78° C. for 0.5 hr, a solution of 5β-pregnan-3,20-dione, cyclic 20-(1,2-ethanediyl acetal) (170 mg, 0.47 mmol) in THF (15 mL) was added and the mixture was stirred at –78° C. for 1 hr. The cooling bath was removed and the mixture was quenched with $NH_4Cl$ solution (3 mL). The solvent was removed and the residue was then dissolved in acetone (25 mL). After adding 2 N HCl (2 mL) the solution was stirred at rt for 15 min. Sat. $NaHCO_3$ soln. was added to neutralize the acid. The solvents were removed and the residue was extracted with EtOAc. The organic layer was washed with water, and brine. After drying over anhyd. $MgSO_4$ the solution was filtered and evaporated to yield the crude product (360 mg). This crude product was then dissolved in a small amount of $CH_2Cl_2$ and poured on a column of silica gel. Elution with toluene:acetone mixture (95:5) gave the unreacted ethynylpyridine as a first fraction. Further elution with the same solvent mixture yielded 3β-(2-pyridyl) ethynyl-3α-hydroxy-5β-pregnan-20-one (170 mg) as a colorless solid; mp 192–195° C.; TLC $R_f$ (toluene:acetone 87:13)=0.21.

EXAMPLE 20

3β-(6-hydroxy-1-hexynyl)-3α-hydroxy-5β-pregnan-20-one

A solution of 5-hexyn-1-ol (1.35 mL, 12 mmol) in dry THF (15 mL) was treated with n-BuLi (9.6 mL, 2.5 M in THF, 24 mmol) at −65° C. After stirring the mixture at −78° C. for 0.5 hr, a solution of 5β-pregnan-3,20 -dione, cyclic 20-(1,2-ethanediyl acetal) (1.08 g, 3 mmol) in THF (20 mL) was added and the mixture was stirred at −78° C. for 1 hr. The cooling bath was removed and the stirring was continued at rt for 45 min. The mixture was then quenched with NH$_4$Cl solution (5 mL). The solvent was removed the residue was extracted with EtOAc. The organic layer was washed with water, dil. NaHCO$_3$ soln., water, and brine. After drying over anhyd. MgSO$_4$. The solution was filtered and evaporated to yield the crude product (1.90 g). This crude product was then crystallized from EtOAc to yield the pure product as colorless rods (890 mg). this was then dissolved in acetone (120 mL). After adding 2 N HCl (3 mL) the solution was stirred at rt for 15 min. Sat. NaHCO$_3$ soln. was added to neutralize the acid. The solvents were removed and the residue was extracted with EtOAc. The organic layer was washed with water, and brine. After drying over anhyd. MgSO$_4$, the solution was filtered and evaporated to yield the crude product. This crude product was then dissolved in a small amount of CH$_2$Cl$_2$ and poured on a column of silica gel. Elution with toluene:acetone mixture (95:5) gave the unreacted hexynol as a first fraction. Further elution with the same solvent mixture yielded 3α-(6-hydroxy-1-hexynyl)-3β-hydroxy-5β-pregnan-20-one (60 mg), and then 3β-(6-hydroxy-1-hexynyl)-3α-hydroxy-5β-pregnan-20-one (620 mg) as a colorless solid; mp 132–134° C.; TLC R$_f$ (hexane:acetone 7:3)=0.23.

EXAMPLE 21

3β-(6'-Hydroxy-1'-hexynyl)-3α-hydroxy-5β-pregnan-20-one 6'-hemisuccinate sodium salt a. 3β-(6'-Hydroxy-1'-hexynyl)-3α-hydroxy-5β-pregnan-20-one 6'-hemisuccinate A solution of 3β-(6'-hydroxy-1'-hexynyl)-3α-hydroxy-5β-pregnan-20-one (600 mg, 1.45 mmol) in pyridine (5 mL) was treated with succinic anhydride (600 mg, 6 mmol) and 4-(N,N-dimethyl)aminopyridine (20 mg). The mixture was heated to 70–75° C. for 1.25 hr. The tlc showed 100% conversion. It was cooled to rt and was poured into ice-2 N HCl. The organics were extracted with EtOAc. The organic layer was washed with 0.2 N HCl, water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with hexane:acetone mixture (7:3) gave 3β-(6'-hydroxy-1'-hexynyl)-3α-hydroxy-5β-pregnan-20-one 6'-hemisuccinate (700 mg); TLC R$_f$ (hexane:acetone:AcOH 70:30:0.5)=0.21.

b. 3β-(6'-hydroxy-1'-hexynyl)-3α-hydroxy-5βpregnan-20-one 6'-hemisuccinate sodium salt A mixture of the above hemisuccinate (400 mg), NaHCO$_3$ (68 mg), water (8 mL), and CH$_2$Cl$_2$ (1 mL) was stirred at rt for 15 min. The solvent was removed and the residue was freeze-dried to yield the sodium salt as a colorless solid (400 mg).

EXAMPLE 22

3β-(5'-Hydroxy-1'-pentynyl)-3α-hydroxy-5β-pregnan-20-one

A solution of 4-pentyn-1-ol (1.1 mL, 12 mmol) in dry THF (15 mL) was treated with n-BuLi (9.9 mL, 2.5 M in THF, 24.5 mmol) at −65° C. After stirring the mixture at −78° C. for 0.5 hr, a solution of 5β-pregnan-3,20-dione, cyclic 20-(1,2-ethanediyl acetal) (1.08 g, 3 mmol) in THF (20 mL) was added and the mixture was stirred at −78° C. for 1 hr. The cooling bath was removed and the stirring was continued at rt for 45 min. The mixture was then quenched with NH$_4$Cl solution (5 mL). The solvent was removed the residue was then dissolved in acetone (30 mL). After adding 2 N HCl (7 mL) the solution was stirred at rt for 15 min. Sat. NaHCO$_3$ soln. was added to neutralize the acid. The solvents were removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with toluene:acetone:EtOAc mixture (70:15:15) gave the unreacted pentynol as a first fraction. Further elution with the same solvent mixture yielded 3α-(5'-hydroxy-1'-pentynyl)-3β-hydroxy-5β-pregnan-20-one (100 mg), and then 3β-(5'-hydroxy-1'-pentynyl)-3α-hydroxy-5β-pregnan-20-one (650 mg) as a colorless solid; mp 160–163° C.; TLC R$_f$ (toluene:acetone:EtOAc 70:15:15)=0.28.

An analogus method was used to prepare: 3β-(4'-hydroxy-1'-butynyl)-3α-hydroxy-5β-pregnan-20-one; 3β-(4'-hydroxy-1'-butynyl)-3α-hydroxy-5β-19-norpregnan-20-one; 3β-(4'-hydroxy-1'-hydroxy-1'-butynyl)-3α-hydroxy-5α-pregnan-20-one; 3β-[4'(R/S)-hydroxy-1'-pentynyl]-3α-hydroxy-5α-pregnan-20-one; 3β-[3'(R/S)-hydroxy-1'-butynyl]-3α-hydroxy-5α-pregnan-20-one; and 3β-(3'-hydroxy-1'-propynyl)-3α-hydroxy-5β-pregnan-20-one.

EXAMPLE 23

3β-(5'-Hydroxy-1'-pentynyl)-3α-hydroxy-5β-pregnan-20-one 5'-hemisuccinate sodium salt a. 3β-(5'-hydroxy-1'-pentynyl)-3α-hydroxy-5β-pregnan-20-one 5'-hemisuccinate A solution of 3β-(6'-hydroxy-1'-hexynyl)-3α-hydroxy-5β-pregnan-20-one (350 mg, 0.87 mmol) in pyridine (3 mL) was treated with succinic anhydride (380 mg, 3.8 mmol) and 4-(N,N-dimethyl)aminopyridine (20 mg). The mixture was heated to 65–70° C. for 1 hr. The TLC showed 100% conversion. It was cooled to rt and was poured into ice-2 N HCl. The organics were extracted with EtOAc. The organic layer was washed with 0.2 N HCl, water, and brine. After drying over anhyd. MgSO$_4$ the solution was filtered and evaporated to yield the crude product (900 mg). This crude product was then dissolved in a small amount of CH$_2$Cl$_2$ and poured on a column of silica gel. Elution with hexane:acetone mixture (7:3) gave 3β-(5'-hydroxy-1'-pentynyl)-3α-hydroxy-5β-pregnan-20-one 5'-hemisuccinate (350 mg); TLC R$_f$ (hexane:acetone:AcOH 70:30:0.5)=0.25.

b. 3β-(5'-hydroxy-1'-pentynyl)-3α-hydroxy-5β-pregnan-20-one 5'-hemisuccinate sodium salt A mixture of the above hemisuccinate (345 mg), NaHCO$_3$ (60 mg), water (5 mL), THF (2 mL), and CH$_2$Cl$_2$ (1 mL) was stirred at rt for 1 hr. The solvent was removed and the residue was freeze-dried to yield the sodium salt as a colorless solid (340 mg).

An analogous method was used to prepare hemisuccinate sodium salts from: 3β-(4'-hydroxy-1'-butynyl)-3α-hydroxy-5β-pregnan-20-one; 3β-(4'-hydroxy-1'-butynyl)-3α-hydroxy-5β-19-norpregnan-20-one; 3β-(4'-hydroxy-1'-butynyl)-3α-hydroxy-5α-pregnan-20-one; 3β-[4'(R/S)-hydroxy-1'-pentynyl]-3α-hydroxy-5α-pregnan-20-one; 3β-[3'(R/S)-hydroxy-1'-butynyl]-3α-hydroxy-5α-pregnan-20-one; and 3β-(3'-hydroxy-1'-propynyl)-3α-hydroxy-5β-pregnan-20-one.

EXAMPLE 24

3β-(5'-Acetoxy-1'-pentynyl)-3α-hydroxy-5β-pregnan-20-one

A solution of pyridine (280 mg) in CH$_2$Cl$_2$ (2 mL) was treated with acetyl chloride (280 mg) at 0–5° C. A solution of 3β-(5'-hydroxy-1'-pentynyl)-3α-hydroxy-5β-pregnan-20-one (130 mg) in CH$_2$Cl$_2$ (3 mL) was added. The stirring was continued at 0° C. for 20 min. The TLC showed 100% conversion, hence, the mixture was poured into ice-2 N HCl (20 g, 2 mL). The organics were extracted with EtOAc. The organic layer was washed with 0.2 N HCl, water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with toluene:acetone mixture (9:1) gave 3β-(5'-acetoxy-1'-pentynyl)-3α-hydroxy-5β-pregnan-20-one (100 mg); mp 84–87° C.; TLC R$_f$ (hexane:acetone 70:30)=0.38.

EXAMPLE 25

3β-(4'-Acetoxy-1'-butynyl)-3α-hydroxy-5β-pregnan-20-one

A solution of pyridine (280 mg) in CH$_2$Cl$_2$ (2 mL) was treated with acetyl chloride (280 mg) at 10° C. A solution of 3β-(4'-hydroxy-1'-butynyl)-3α-hydroxy-5β-pregnan-20-one (110 mg) in CH$_2$Cl$_2$ (3 mL) was added. The stirring was continued at 10° C. for 30 min. The TLC showed 100% conversion, hence, the mixture was poured into ice-2 N HCl (20 g, 3 mL). The organics were extracted with EtOAc. The organic layer was washed with 0.2 N HCl, water, and brine. After drying over anhyd. MgSO$_4$ the solution was filtered and evaporated to yield the crude product. This crude product was then dissolved in a small amount of CH$_2$Cl$_2$ and poured on a column of silica get. Elution with hexane:acetone mixture (4:1) gave 3β-(4'-acetoxy-1'-butynyl)-3α-hydroxy-5β-pregnan-20-one (92 mg); mp 170–173° C.; TLC R$_f$ (hexane:acetone 70:30)=0.3.

EXAMPLE 26

3β-(6'-Acetoxy-1'-hexynyl)-3α-hydroxy-5β-pregnan-20-one

A solution of pyridine (2 mL) in CH$_2$Cl$_2$ (10 mL) was treated with acetyl chloride (2 mL) at 0° C. A solution of 3β-(6'-hydroxy-1'-hexynyl)-3α-hydroxy-5β-pregnan-20-one (400 mg, 0.96 mmol) in CH$_2$Cl$_2$ (5 mL) was added. The stirring was continued at 0° C. for 20 min. The TLC showed 100% conversion, hence, the mixture was poured into ice-2 N HCl (50 g, 11 mL). The organics were extracted with EtOAc. The organic layer was washed with 0.2 N HCl, water, and brine. After drying over anhyd. MgSO$_4$ the solution was filtered and evaporated to yield the crude product (500 mg). This crude product was then dissolved in a small amount of CH$_2$Cl$_2$ and poured on a column of silica gel. Elution with toluene:acetone mixture (95:5) gave 3β-(6'-acetoxy-1'-hexynyl)-3α-hydroxy-5β-pregnan-20-one (130 mg); mp 85–87° C.; TLC R$_f$ (toluene:acetone 93:7)=0.2.

EXAMPLE 27

3α-Hydroxy-3β-[3-(2'-propynyloxy)-1-propynyl]-5β-pregnan-20-one

A solution of propargyl ether (0.3 mL, 3 mmol) in dry THF (10 mL) was treated with n-BuLi (2.4 M in THF, 3 mmol, 1.25 mL) at −70° C. After stirring the mixture at −75° C. for 0.5 hr, a solution of 5β-pregnan-3,20-dione, cyclic 20-(1,2-ethanediyl acetal) (360 mg, 1 mmol) in THF (10 mL) was added and the mixture was stirred at −78° C. for 1 hr. The cooling bath was removed and the mixture was quenched with NH$_4$Cl solution (5 mL). The solvent was removed and the residue was then dissolved in acetone (40 mL). After adding 1 N HCl (4 mL) the solution was stirred at rt for 15 min. Sat. NaHCO$_3$ soln. was added to neutralize the acid. The solvents were removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica get. Elution with toluene:acetone mixture (95:5) gave 3β-Hydroxy-3α-[3-(2'-propynyloxy)-1-propynyl]-5β-pregnan-20-one (31 mg) as a first fraction. Further elution with the same solvent mixture yielded 3α-hydroxy-3β-[3-(2'-propynyloxy)-1-propynyl]-5β-pregnan-20-one (255 mg) as a colorless solid; mp 103–106° C.; TLC R$_f$ (toluene:acetone 95:5)=0.39.

Example 28

3α-Hydroxy-3β-(3-methoxy-1-propynyl)-5β-pregnan-20-one

A solution of methyl propargyl ether (0.25 mL, 3 mmol) in dry THF (10 mL) was treated with n-BuLi (2.4M in THF, 2.9 mmol, 1.20 mL) at −70° C. After stirring the mixture at −75° C. for 0.5 hr, a solution of 5-β-pregnan-3,20-dione, cyclic 20-(1,2-ethanediyl acetal) (185 mg, 0.5 mmol) in THF (10 mL) was added and the mixture was stirred at −78° C. for 20 min. The cooling bath was removed and the mixture was quenched with NH$_4$Cl solution (2 mL). The solvent was removed and the residue was then dissolved in acetone (25 mL). After adding 2N HCl (2 mL) the solution was stirred at rt for 15 min. Sat. NaHCO$_3$ soln. was added to neutralize the acid. The solvents were removed and the residue was extracted with EtOAc. The organic layer was washed with water, and brine. After drying over anhyd. MgSO$_4$ the solution was filtered and evaporated to yield the crude product (250 mg). This crude product was then dissolved in a small amount of CH$_2$Cl$_2$ and poured on a column of silica gel. Elution with toluene:acetone mixture (93:7) gave 3β-hydroxy-3α-(3-methoxy-1-propynyl)-5β-pregnan-20-one (19 mg) as a first fraction. Further elution with the same solvent mixture yielded 3α-hydroxy-3β-(3-methoxy-1-propynyl)-5β-pregnan-20-one (115 mg) as a colorless solid; mp 155–159° C.; TLC R$_f$ (hexane:acetone)=0.25.

Example 29

3α-Hydroxy-3β-[3-(4'-pyridinyloxy)-1-propynyl]-5β-pregnan-20-one

A solution of propargyl 4-pyridyl ether (prepared according to (Thummel et al, *J. Org. Chem.* 1978, 43, 4882) (173 mg, 1.3 mmol) in dry THF (15 mL) was treated with n-BuLi (2.5M in THF, 1.3 mmol, 0.52 mL) at −70° C. After stirring the mixture at −75° C. for 0.5 hr, a solution of 5β-pregnan-3,20-dione, cyclic 20-(1,2-ethanediyl acetal) (180 mg, 0.5 mmol) in THF (15 mL) was added and the mixture was stirred at −78° C. for 20 min. The cooling bath was removed and the stirring was continued at rt for 1 hr. The mixture was quenched with NH$_4$Cl solution (2 mL). The solvent was removed and the residue was then dissolved in acetone (25 mL). After adding 2N HCl (2 mL) the solution was stirred at rt for 20 min. Sat. NaHCO$_3$ soln. was added to neutralize the acid. The solvents were removed and the residue was extracted with EtOAc. The organic layer was washed with water, and brine. After drying over anhyd. MgSO$_4$ the solution was filtered and evaporated to yield the crude product (250 mg). This crude product was then dissolved in a small amount of $CH_2Cl_2$ and poured on a column of silica gel. Elution with $CH_2Cl_2$:acetone mixture (90:10) gave 3α-hydroxy-3β-[3-(4'-pyridinyloxy)-1-propynyl]-5β-pregnan-20-one (145 mg) as a colorless solid; mp 84–90° C.; TLC $R_f$ ($CH_2Cl_2$:acetone 85:15)=0.17.

Example 30

3α-Hydroxy-3β-[3-(1'H-1,2,3-triazol-1'-yl)-1-propynyl]-5β-pregnan-20-one

A solution of 1-(2-propynyl)-1H-1,2,3-triazole (prepared by the reaction of triazole with propargyl bromide) (77 mg, 0.72 mmol) in dry THF (10 mL) was treated with n-BuLi (2.5M in THF, 0.72 mmol, 0.28 mL) at −70° C. After stirring the mixture at −75° C. for 0.5 hr, a solution of 5β-pregnan-3,20-dione, cyclic 20-(1,2-ethanediyl acetal) (130 mg, 0.36 mmol) in THF (10 mL) was added and the mixture was stirred at −78° C. for 1 hr. The cooling bath was removed and the mixture was quenched with $NH_4Cl$ solution (1 mL). The solvent was removed and the residue was then dissolved in acetone (25 mL). After adding 2N HCl (2 mL) the solution was stirred at rt for 30 min. Sat. $NaHCO_3$ soln. was added to neutralize the acid. The solvents were removed and the residue was extracted with EtOAc. The organic layer was washed with water, and brine. After drying over anhyd. $MgSO_4$ the solution was filtered and evaporated to yield the crude product. This crude product was then dissolved in a small amount of $CH_2Cl_2$ and poured on a column of silica gel. Elution with toluene:acetone mixture (85:15) gave 3α-hydroxy-3β-[3-(1'H-1,2,3-triazol-1'-yl)-1-propynyl]-5β-pregnan-20-one (56 mg) as a colorless solid; mp 142–144° C.; TLC $R_f$ (hexane:acetone 7:3)=0.33.

Example 31

3α-Hydroxy-3β-[3-(2'H-1,2,3-triazol-2'-yl)-1-propynyl]-5β-pregnan-20-one

A solution of 2-(2-propynyl)-2H-1,2,3-triazole (prepared by the reaction of triazole with propargyl bromide) (35 mg, 0.33 mmol) in dry THF (10 mL) was treated with n-BuLi (2.5M in THF, 0.33 mmol, 0.15 mL) at −70° C. After stirring the mixture at −75° C. for 0.5 hr, a solution of 5β-pregnan-3,20-dione, cyclic 20-(1,2-ethanediyl acetal) (60 mg, 0.16 mmol) in THF (10 mL) was added and the mixture was stirred at −78° C. for 1 hr. The cooling bath was removed and the mixture was quenched with $NH_4Cl$ solution (1 mL). The solvent was removed and the residue was then dissolved in acetone (25 mL). After adding 2N HCl (2 mL) the solution was stirred at rt for 30 min. Sat. $NaHCO_3$ soln. was added to neutralize the acid. The solvents were removed and the residue was extracted with EtOAc. The organic layer was washed with water, and brine. After drying over anhyd. $MgSO_4$ the solution was filtered and evaporated to yield the crude product. This crude product was then dissolved in a small amount of $CH_2Cl_2$ and poured on a column of silica gel. Elution with toluene:acetone mixture (85:15) gave pregnan-3,20-dione (20 mg) as a first fraction. Further elution with the same solvent yielded 3α-hydroxy-3β-[3-(2'H-1,2,3-triazol-2'-yl)-1-propynyl]-5β-pregnan-20-one (20 mg) as a colorless solid; mp 139–140° C.; TLC $R_f$ (hexane:acetone 4:1)=0.17.

Example 32

3α-Hydroxy-3β-(2'-thienyl)ethynyl-5β-pregnan-20-one

A solution of 4-iodothiophene (63 mg, 0.3 mmol), 3β-ethynyl-3α-hydroxy-5β-pregnan-20-one (103 mg, 0.3 mmol) in dry degassed triethylamine (1 mL) was stirred under argon at 23° C. Bis(triphenylphosphine)palladium(II) dichloride (5 mg) and CuI (5 mg) were added and the mixture was stirred at this temp. for 45 min. $CH_2Cl_2$ (5 mL) was added and the mixture was stirred at 23° C. for 1 hr. The TLC showed 100% conversion of the starting material, hence, the solvent was removed, and the residue was purified by chromatography on silica gel. Elution with hexane:acetone (4:1) gave 3α-hydroxy-3β-(2'-thienyl)ethynyl-5β-pregnan-20-one (50 mg) as a colorless solid; mp 205–206° C., TLC $R_f$ (hexane:acetone 4:1)=0.35.

An analogus method was used to prepare 3α-hydroxy-3β-(5'-acetyl-2'-thienyl)ethynyl-5β-pregnan-20-one; mp 226–228° C., TLC $R_f$ (hexane:acetone 4:1)=0.14.

Example 33

3α-Hydroxy-3β-(3'-phenyl-1'-propynyl)-5β-pregnan-20-one

A solution of 3-phenyl-1-propyne (0.25 mL, 2 mmol) in dry THF (17 mL) was treated with n-BuLi (2.5M in THF, 2 mmol, 0.8 mL) at −70° C. After stirring the mixture at −75° C. for 10 min., a solution of 5β-pregnan-3,20-dione, cyclic 20-(1,2-ethanediyl acetal) (206 mg, 0.6 mmol) in THF (10 mL) was added and the mixture was stirred at −78° C. for 20 min. The cooling bath was removed and the mixture was quenched with $NH_4Cl$ solution (5 mL). The solvent was removed and the residue was then dissolved in acetone (15 mL). After adding 2N HCl (4 mL) the solution was stirred at rt for 20 min. Sat. $NaHCO_3$ soln. was added to neutralize the acid. The solvents were removed and the residue was extracted with EtOAc. The organic layer was washed with water, and brine. After drying over anhyd. $MgSO_4$ the solution was filtered and evaporated to yield the crude product (460 mg). This crude product was then dissolved in a small amount of $CH_2Cl_2$ and poured on a column of silica gel. Elution with toluene:acetone mixture (85:15) gave the unreacted phenylpropyne as a first fraction. Further elution with the same solvent yielded 3α-hydroxy-3β-(3'-phenyl-1'-propynyl)-5β-pregnan-20-one (175 mg) as a colorless solid; mp 124–132° C.; TLC $R_f$ (hexane:acetone 7:3)=0.46.

Example 34

3α-Hydroxy-3β-(3'-phenylpropynyl)-5β-pregnan-20-one

A solution of the above phenylpropynyl derivative (50 mg) in EtOAc (10 mL) was hydrogenated over Pd/C (10 mg, 5%) under 2 atm. of $H_2$ for 45 min. The mixture was then filtered through a small pad of Celite, and concentrated to yield the title compound as a colorless solid (40 mg); mp 41–46° C.; $R_f$ (hexane:acetone 7:3)=0.48.

Example 35

3α-Hydroxy-3β-[3-(1'H-pyrazol-1'-yl)-1-propynyl]-5β-pregnan-20-one

A solution of 1-(2-propynyl)-1H-pyrazole (prepared by the reaction of pyrazole with propargyl bromide (160 mg, 1.5 mmol) in dry THF (15 mL) was treated with n-BuLi (2.5M in THF, 1.5 mmol, 0.6 mL) at −70° C. After stirring the mixture at −75° C. for 0.5 hr, a solution of 5β-pregnan-3,20-dione, cyclic 20-(1,2-ethanediyl acetal) (180 mg, 0.5 mmol) in THF (15 mL) was added and the mixture was stirred at −78° C. for 1 hr. The cooling bath was removed and the mixture was quenched with $NH_4Cl$ solution (1 mL). The solvent was removed and the residue was then dissolved in acetone (25 mL). After adding 2N HCl (2 mL) the solution was stirred at rt for 30 min. Sat. NaHCO$_3$ soln. was added to neutralize the acid. The solvents were removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica gel. Elution was toluene:acetone mixture (9:1) gave 3α-hydroxy-3β-[3-(1'H-pyrazol-1'-yl)-1-propynyl]-5β-pregnan-20-one (80 mg) as a colorless solid; mp 113–115° C.; TLC R$_f$ (toluene:acetone 9:1)=0.19.

Example 36

3β-(3'-Acetylphenylethynyl)-3α-hydroxy-5β-pregnan-20-one

A solution of 3-iodoacetophenone (74 mg, 0.3 mmol), 3β-ethynyl-3α-hydroxy-5β-pregnan-20-one (103 mg, 0.3 mmol) in dry degassed triethylamine (1 mL) was stirred under argon at 23° C. Bis(triphenylphosphine)palladium(II) dichloride (5 mg) and CuI (5 mg) were added and the mixture was stirred at this temp. for 45 min. CH$_2$Cl$_2$ (5 mL) was added and the mixture was stirred at 23° C. for 1.5 hr. The TLC showed 100% conversion of the starting material, hence, the solvent was removed and the residue was purified by chromatography on silica gel. Elution with hexane:acetone (85:15) gave 3β-(3'-acetylphenylethynyl)-3α-hydroxy-5β-pregnan-20-one (30 mg) as a colorless solid; mp ° C., TLC R$_f$ (hexane:acetone 4:1)=0.

Example 37

3β-(3'-Acetoxy-3'-propynyl)-3α-hydroxy-5β-pregnan-20-one

A solution of pyridine (280 mg) in CH$_2$Cl$_2$ (2 mL) was treated with acetyl chloride (280 mg) at 0–5° C. A solution of 3β-(3'-hydroxy-1'-propynyl)-3α-hydroxy-5β-pregnan-20-one (130 mg) in CH$_2$Cl$_2$ (3 mL) was added. The stirring was continued at 0° C. for 30 min. The TLC showed 100% conversion, hence, the mixture was poured into ice-2N HCl (20 g, 3 mL). The organics were extracted with EtOAc. The organic layer was washed with 0.2N HCl, water, and brine. After drying over anhyd. MgSO$_4$ the solution was filtered and evaporated to yield the crude product (150 mg). This crude product was then dissolved in a small amount of CH$_2$Cl$_2$ and poured on a column of silica gel. Elution with toluene:acetone mixture (4:1) gave 3β-(3'-acetoxy-1'-propynyl)-3α-hydroxy-5β-pregnan-20-one (110 mg); mp 132–150° C.; TLC R$_f$ (hexane:acetone 70:30)=0.37.

Example 38

3α-Hydroxy-3β-(4-hydroxybutyn-1-yl)-21-(1-imidazolyl)-5β-pregnan-20-one a. 21-Bromo-3α-hydroxy-3β-(4-hydroxybutyn-1-yl)-5β-pregnan-20-one A solution of 3α-hydroxy-3β-(4-hydroxybutyn-1-yl)-5β-pregnan-20-one (386 mg, 1 mmol) in MeOH (20 mL) was treated with two drops of acetyl chloride, followed by bromine (1.2 mmol). The mixture was stirred at rt for 2.5 hr and was poured into ice-water. The separated solid was collected by filtration, washed with water, dried (410 mg). This semi-dried solid was then dissolved in EtOAc and dried over anhyd. MgSO$_4$. Filtration and removal of the solvent gave the crude bromo derivative, and it was used as such for the next step.

b. 3α-Hydroxy-3β-(4-hydroxybutyn-1-yl)-21-1-imidazolyl)-5β-pregnan-20-one

A suspension of NaH (138 mg, 95%, 5.46 mmol) in THF (10 mL) was treated with a solution of imidazole (345 mg, 5.1 mmol) in THF (10 mL) at rt. After stirring the mixture for 30 min a solution of the crude bromo derivative (95 mg, 0.2 mmol) in THF (10 mL) was added. The stirring was continued at rt for 1 hr. Sat. NH$_4$Cl soln. was added and the solvent was removed. The residue was extracted with EtOAc. The organic layer was washed with water, and brine. After drying over anhyd. MgSO$_4$ the solution was filtered and evaporated to yield the crude product (100 mg). This crude product was then dissolved in a small amount of CH$_2$Cl$_2$ and poured on a column of silica gel. Elution with CH$_2$Cl$_2$:MeOH:NEt$_3$ (95:4.5:0.5) mixture gave 3α-hydroxy-3β-(4-hydroxybutyn-1-yl)-21-(1-imidazolyl)-5β-pregnan-20-one (40 mg) as a colorless solid; mp 117–119° C.; TLC R$_f$ (CH$_2$Cl$_2$:MeOH:NEt$_3$ 95:4.5:0.5) 0.21.

Similarly prepared were 3α-hydroxy-3β-(4-hydroxybutyn-1-yl)-21-(1,2,4-triazol-1-yl)-5β-pregnan-20-one; mp 208–210° C.; TLC R$_f$ (CH$_2$Cl$_2$:MeOH:NEt$_3$ 95:4.5:0.5) 0.24; 3α-hydroxy-3β-(4-hydroxybutyn-1-yl)-21-(tetrazol-1--yl)-5β-pregnan-20-one; mp 110–112° C.; TLC R$_f$ (CH$_2$Cl$_2$:MeOH:NEt$_3$ 96:3.5:0.5) 0.11; 3α-hydroxy-3β-(4-hydroxybutyn-1-yl)-21-(1,2,3-triazol-1-yl)-5β-pregnan-20-one; mp 101–104° C.; TLC R$_f$ (CH$_2$Cl$_2$:MeOH:NEt$_3$ 95:4.5:0.5) 0.2.

Example 39

3α-Hydroxy-3β-(4-hydroxybutyn-1-yl)-21-(1-imidazolyl)-5β-norpregnan-20-one a. 21-Bromo-3α-hydroxy-3β-(4-hydroxybutyn-1-yl)-5β-19-norpregnan-20-one A solution of 3α-hydroxy-3β-(4-hydroxybutyn-1-yl)-21-(1-imidazolyl)-5β-norpregnan-20-one (710 mg, 1.9 mmol) in MeOH (60 mL) was heated to 33° C. and was treated with two drops of acetyl chloride, followed by bromine (2.28 mmol, (0.116 mL). The mixture was stirred at rt for 1.5 hr and was poured into ice-water. The separated solid was collected by filtration, washed with water, dried. This semi-dried solid was then dissolved in EtOAc and dried over anhyd. MgSO$_4$. Filtration and removal of the solvent gave the crude bromo derivative (870 mg), and it was used for the next step.

b. 3α-Hydroxy-3β-(4-hydroxybutyn-1-yl)-21-(1-imidazolyl)-5β-norpregnan-20-one

A suspension of NaH (138 mg, 95%, 5.46 mmol) in THF (10 mL) was treated with a solution of imidazole (345 mg, 5.1 mmol) in THF (10 mL) at rt. After stirring the mixture for 30 min a solution of the crude bromo derivative (90 mg, 0.2 mmol) in THF (10 mL) was added. The stirring was continued at rt for 1 hr. Sat. NH$_4$Cl soln. was added and the solvent was removed. The residue was extracted with EtOAc. The organic layer was washed with water, and brine. After drying over anhyd. MgSO$_4$ the solution was filtered and evaporated to yield the crude product (100 mg). This crude product was then dissolved in a small amount of CH$_2$Cl$_2$ and poured on a column of silica gel. Elution with CH$_2$Cl$_2$:MeOH:NEt$_3$ (95:4.5:0.5) mixture gave 3α-Hydroxy-3β-(4-hydroxybutyn-1-yl)-21-(1-imidazolyl)-5β-norpregnan-20-one (25 mg) as a colorless solid; mp 118–127° C.; TLC R$_f$ CH$_2$Cl$_2$:MeOH:NEt$_3$ 95:4.5:0.5) 0.28.

Example 40

3α-Hydroxy-3β-(4-hydroxybutyn-1-yl)-21-(1,2,3-triazol-2-yl)-5β-19-norpregnan-20-one and 3α-Hydroxy-3β-(4-hydroxybutyn-1-yl)-21-(1,2,3-triazol-1-yl)-5β-19-norpregnan-20-one A suspension of NaH (11 mg, 95%, 0.44 mmol) in THF (10 mL) was treated with a solution of 1,2,3-triazole (30 mg, 0.44 mmol) in THF (10 mL) at rt. After stirring the mixture for 30 min a solution of the crude 21-bromo-3α-hydroxy-3β-(4-hydroxybutyn-1-yl)-5β-pregnan-20-one (100 mg, 0.22 mmol) in THF (10 mL) was added. The stirring was continued at rt for 1 hr. Sat. NH$_4$Cl soln. was added and the solvent was removed. The residue was extracted with EtOAc. The organic layer was washed with water, and brine. After drying over anhyd. MgSO$_4$ the solution was filtered and evaporated to yield the crude product (100 mg). This crude product was then dissolved in a small amount of CH$_2$Cl$_2$ and poured on a column of silica gel. Elution with CH$_2$Cl$_2$:acetone (4:1) mixture gave 3α-hydroxy-3β-(4-hydroxybutyn-1-yl)-21-(2H-1,2,3-triazol-2-yl)-5β-19-nonpregnan-20-one (15 mg) as a first fraction; mp 158–160° C.; TLC R$_f$ (CH$_2$Cl$_2$:acetone 4:1) 0.36. Further elution with the same solvent mixture yielded 3α-hydroxy-3β-(4-hydroxybutyn-1-yl)-21-(1H-1,2,3-triazol-2-yl)-5β-19-nonpregnan-20-one (15 mg); mp 188–190° C.; TLC R$_f$ (CH$_2$Cl$_2$:acetone 4:1) 0.2.

Example 41

3α-Hydroxy-2β-morpholinyl-21-[1'-(1', 2', 4'-triazolyl)]-5α-pregnan-20-one

To a solution of 1,2,4-triazole (108 mg, 1.57 mmol) in dry THF (2.5 ml) was added sodium hydride (36 mg, 1.50 mmol). The mixture was stirred at 25° C. under argon for 0.5 hour. Then 3α-hydroxy-2β-morpholinyl-21-bromo-5α-pregnan-20-one (130 mg, 0.27 mmol) was added and the mixture was further stirred at 25° C. under argon for 2.5 hours. Water (20 ml) was added slowly to the reaction mixture. The product was extracted with ethyl acetate (3×25 ml). The combined extracts were washed with brine (20 ml) and water (3×20 ml). The organic solution obtained was dried over sodium sulfate and the solvent was removed in vacuo to give the crude product (130 mg). The pure product (90 mg, 71%) was obtained by flash chromatography (30 g of silica gel and 300 ml of mixed solvent of CH$_2$Cl$_2$:MeOH:Et$_3$N=95:4.5:0.5, R$_f$=0.14).

Example 42

3α-Hydroxy-21-(1'-uracil)-5α-pregnan-20-one

To a suspension of uracil (112 mg, 1 mmol) and K$_2$CO$_3$ (138 mg, 1 mmol) in DMF (1.5 mL) was added 3α-hydroxy-21-bromo-5α-pregnan-20-one (400 mg, 1 mmol) and the mixture obtained was stirred at 25° C. for 65 h. It was then poured into a separatory funnel containing water (60 ml) and ethyl acetate (100 mL). The water was removed after shaking and the white solid in the organic layer was obtained by filtration as the product (87 mg, 20%). m.p.262–265° C. (decomp).

Example 43

Sodium S-(3α-hydroxy-5α-pregnan-20-on-21-yl) thiosulfate

To a solution of 21-bromo-3α-hydroxy-5α-pregnan-20-one (500 mg, 1.26 mmol) dissolved in 50 mL of ethanol was added dropwise a solution of sodium thiosulfate (199 mg, 1.26 mmol) in 10 mL of water. The reaction was allowed to stir at rt until TLC (1:1 acetone/dichloromethane) indicated complete consumption of the starting bromide. Concentration of the reaction in vacuo gave the desired thiosulfate contaminated with sodium bromide. Flash column chromatography (silica gel eluted with a gradient from 1:1 to 3:1 acetone/dichloromethane) afforded 430 mg (75%) of the title compound as a white solid.

Similarly prepared were sodium S-(3α-hydroxy-3β-methyl-5α-pregnan-20-on-21-yl) thiosulfate, purified by flash chromatography as above, sodium S-(3α-hydroxy-3β-methoxymethyl-5α-pregnan-20-on-21-yl) thiosulfate, purified by recrystallization from 50:1 methanol/water, sodium S-(3α-hydroxy-5β-pregnan-20-on-21-yl) thiosulfate, purified by flash chromatography with silica gel and 3:1 acetone/ethanol, sodium S-[3α-hydroxy-3β-(4'-hydroxybutynyl)-5β-pregnan-20-on-21-yl] thiosulfate, purified by trituration with hot acetone, and sodium S-(3α-hydroxy-3β-trifluoromethyl-5β-19-nonpregnan-20-on-21-yl) thiosulfate, purified by trituration with hot acetone/chloroform.

Example 44

3α-Hydroxy-3β-(E)-(2-phenylethenyl)-5α-pregnan-20-one

Benzyl phenyl sulfoxide

To a solution of benzyl phenyl sulfide (Aldrich; 1.068 g, 5.33 mmol) in 25 mL of CH$_2$Cl$_2$ at −78° C. was slowly added a solution of m-chloroperbenzoic acid (Aldrich, 50–60%; 760 mg, 2.64 mmol if 60%) in 10 mL of CH$_2$Cl$_2$. After warming to room temperature and stirring overnight, the solution was added to 20 mL of a saturated NaHCO$_3$ solution. The aqueous layer was separated and extracted with CH$_2$Cl$_2$ (2×10 mL). The pooled organic layers were then dried (MgSO$_4$) and concentrated. The residue was subjected to flash column chromatography (silica gel, 10% acetone/hexane and 15% acetone/hexane) affording the sulfoxide (632 mg, 55%) as a white solid, mp 123–126° C.

20,20-ethylenedioxy-3α-hydroxy-3β-[[2-(phenylsulfinyl)-2-phenyl]ethyl]-5α-pregnane A solution of diisopropylamine (Aldrich, freshly distilled from CaH$_2$; 0.5 mL, 361 mg, 3.57 mmol) in 2 mL of dry THF was cooled to −10° C. and treated with a 1.6 M solution of n-BuLi in hexanes (Aldrich; 1.0 mL, 1.6 mmol) added dropwise via syringe. After 10 m, the reaction was cooled to −75° C. and a solution of benzyl sulfoxide (347 mg, 1.60 mmol) in 5 mL of dry THF was added dropwise via syringe over 30 m. To the resulting deep yellow solution was added 297 mg (0.79 mmol) of solid 20,20-ethylenedioxy-3(R)-5α-pregnan-3-spiro-2'-oxirane. The reaction was allowed to warm to rt and then warmed to 50° C. After 5 h, the reaction was allowed to cool to rt and added to 30 mL of ice-cold water. The resulting mixture was extracted with EtOAc (3×20 mL). The combined EtOAc layers were back extracted with a sat. NaCl solution, dried (Na$_2$SO$_4$) and concentrated. The residue was purified by flash chromatography (silica gel, gradient from 100% CH$_2$Cl$_2$ to 20% acetone/CH$_2$Cl$_2$.) affording the sulfoxide (405 mg, 86%) as a mixture of two diastereomers (based on two benzylic protons in $^1$H NMR).

3α-Hydroxy-3β-[[2-phenylsulfinyl)-2-phenyl]ethyl]-5α-pregnan-20-one

A solution of 20,20-ethylenedioxy-3α-hydroxy-3β-[[2-phenylsulfinyl)-2-phenyl]ethyl]-5α-pregnane (1.30 g, 2.21 mmol) in 15 mL of THF was cooled in an ice/water bath and an aqueous 1N HCl solution (3 mL) was added followed by 2 mL of acetone. After stirring at rt for 70 min, the reaction was recooled to 0° C. and added to an EtOAc/water mixture containing 6 mL of a sat. NaHCO$_3$ solution. The aqueous layer was extracted twice with EtOAc and the combined organic layers were extracted with a sat. NaCl solution, dried (Na$_2$SO$_4$) and concentrated. The residue was carried on to the next step without purification.

3α-Hydroxy-3β-(E)-(2-phenylethenyl)-5α-pregnan-20-one

A suspension of 3α-hydroxy-3β-[[2-phenylsulfinyl)-2-phenyl]ethyl]-5α-pregnan-20-one (963 mg, 1.76 mmol) in 6 mL of p-cymene containing 0.95 mL of 2,4,6-collidine was heated at 135° C. for 1 hr. After standing overnight at 0° C., the product had precipitated and was isolated by filtration. The crude product was washed with cold p-cymene (3×5 mL) and hexane (a total of 120 mL) and afforded 445 mg of the title compound as a white solid, mp 209–213° C.

Example 45

3α-Hydroxy-2β-trimethylsilylethynyl-5α-pregnan-20-one

A solution of trimethylsilylacetylene (0.5 mL, 0.347 g, 3.54 mmol) in 4 mL of dry THF was cooled to −78° C. and treated with a 2.5 M solution of n-BuLi in hexanes. Neat BF$_3$-Et$_2$O (0.3 mL, 0.346 g, 2.44 mmol) was added via syringe. After stirring at −78° C. for 5 m, a solution of 20,20-ethylenedioxy-5α-pregnan-2α,3α-epoxide (557 mg, 1.54 mmol) in 3 mL of dry THF was added over 12 m. After an additional 2.5 h, the reaction was added to a sat. NH$_4$Cl solution. The resulting mixture was extracted with EtOAc (3×25 mL). The combined organic layers were washed with a brine solution, dried (Na$_2$SO$_4$) and concentrated under reduced pressure. The crude reaction mixture was dissolved in 10 mL of acetone, cooled in an ice/water bath and treated with a 1N HCl solution (1 mL). After 1 h at rt, the reaction was added to an ether/water mixture containing 1 mL of a sat. NaHCO$_3$ solution. The aqueous layer was washed twice with ether and the pooled ether layers were washed with a sat. NaCl solution, dried (Na$_2$SO$_4$) and concentrated. Flash column chromatography (silica gel, 12.5% acetone/hexane) afforded 249 mg of the title compound as a white solid, mp 164–167° C.

The procedure above was used for the preparation of 3α-hydroxy-2β-(3'-methoxy-1'-propynyl)-5α-pregnan-20-one.

The hydrolysis of the trimethylsilyl compound with K$_2$CO$_3$/MeOH gave 3α-hydroxy-2β-ethynyl-5α-pregnan-20-one as a white solid, m.p. 179–189° C. (decomp.).

Example 46

3α,21-Dihydroxy-3β-ethynyl-5β-pregnan-20-one a. 21-Bromo-3β-ethynyl-3α-hydroxy-5β-pregnan-20-one A solution of 3β-ethynyl-3α-hydroxy-5β-pregnan-20-one (3 g, 8.77 mmol) in MeOH (110 mL) was treated with two drops of HBr (48%), followed by bromine (0.5 mL, 10.8 mmol). The mixture was stirred at room temperature for 1 hr and was poured into ice-water. The separated solid was collected by filtration, washed with water, and dried (3.2 g). This semi-dried solid was then dissolved in EtOAc and dried over anhyd. MgSO$_4$. Filtration and removal of the solvent gave the crude bromo derivative. This crude product was then dissolved in a small amount of CH$_2$Cl$_2$ and poured on a column of silica gel. Elution with hexane:EtOAc mixture (4:1) gave 21-bromo-3β-ethynyl-3α-hydroxy-5β-pregnan-20-one (3.2 g).

b. 3α,21-Dihydroxy-3β-ethynyl-5β-pregnan-20-one

A solution of the above bromo derivative (3.2 g) in acetone (100 mL) was treated with trifluoroacetic acid (5.8 mL, 76 mmol) and triethylamine (8.5 mL). The mixture was refluxed for 30 min. and then trifluoroacetic acid sodium salt (10 g) was added in portions over a period of 10 hr. After cooling to room temperature, a solution of sat. NaHCO$_3$ was added. The solvent was removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with hexane:EtOAc mixture (3:2) gave 3α,21-dihydroxy-3β-ethynyl-5β-pregnan-20-one (1.6 g). mp 156–157° C.; TLC R$_f$ (hexane:acetone 3:1)=0.2.

Example 47

3β-(4'-Acetylphenylethynyl)-3α,21-dihydroxy-5β-pregnan-20-one

A solution of 4-iodoacetophenone (1.22 g, 4.44 mmol), 3α,21-dihydroxy-3β-ethynyl-5β-pregnan-20-one (1.59 g, 4.44 mmol) in dry degassed triethylamine (7 mL) was stirred under argon at 23° C. Bis(triphenylphosphine)palladium chloride (15 mg) and CuI (5 mg) was added and the mixture was stirred at this temp. for 45 min. CH$_2$Cl$_2$ (30 mL) was added and the mixture was stirred at 23° C. for 1.5 hr. TLC showed 100% conversion of the starting material, hence, the solvent was removed and the residue was purified by chromatography on silica gel. Elution with hexane:acetone (4:1) gave 3β-(4'-acetylphenylethynyl)-3α,21-dihydroxy-5β-pregnan-20-one (1.3 g) as a colorless solid; mp 181–183° C., TLC R$_f$ (hexane:acetone 3:2)=0.14.

Example 48

3β-(4'-Acetylphenylethynyl)-3α,21-dihydroxy-5β-pregnan-20-one 21-hemisuccinate sodium salt a. 3β-(4'-Acetylphenylethynyl)-3α,21-dihydroxy-5β-pregnan-20-one21-hemisuccinate A solution of 3β-(4'-acetylphenylethynyl)-3α,21-dihydroxy-5β-pregnan-20-one (1.3 g, 6.76 mmol) in pyridine (8 mL) was treated with succinic anhydride (680 mg, 2.5 mmol) and 4-(N,N-dimethyl)aminopyridine (25 mg). The mixture was heated to 70–75° C. for 2.5 hr. TLC showed 100% conversion. Pyridine was removed and the residue was extracted with EtOAc. The organic layer was washed with 0.1N HCl, water, and brine. After drying over anhyd. MgSO$_4$, the solution was filtered and evaporated to yield the crude product. This crude product was then dissolved in a small amount of CH$_2$Cl$_2$ and poured on a column of silica gel. Elution with hexane:acetone mixture (7:3) gave 3β-(4'-acetylphenyl-ethynyl)-3α,21-dihydroxy-5β-pregnan-20-one 21-hemisuccinate (1.4 g).

b. 3β-(4'-Acetylphenylethynyl)-3α,21-dihydroxy-5β-pregnan-20-one 21-hemisuccinate sodium salt A mixture of the above hemisuccinate (1.5 g, 2.6 mmol), NaHCO$_3$ (220 mg, 2.6 mmol), water (10 mL), and CH$_2$Cl$_2$ (16 mL) was stirred at room temperature for 1 hr. The solvent was removed and the residue was freeze-dried to yield the sodium salt as a colorless solid (1.4 g).

Example 49

3α,21-Dihydroxy-3β-ethynyl-5α-pregnan-20-one a. 21-Bromo-3β-ethynyl-3α-hydroxy-5α-pregnan-20-one A solution of 3β-ethynyl-3α-hydroxy-5α-pregnan-20-one (2.3 g, 6.72 mmol) in MeOH (80 mL) was treated with two drops of HBr (48%), followed by bromine (0.4 mL, 7.73 mmol). The mixture was stirred at room temperature for 1 hr and was poured into ice-water. The separated solid was collected by filtration, washed with water, and dried (2.5 g). This semi-dried solid was then dissolved in EtOAc and dried over anhyd. $MgSO_4$. Filtration and removal of the solvent gave the crude bromo derivative. This crude product was then dissolved in a small amount of $CH_2Cl_2$ and poured on a column of silica gel. Elution with hexane:EtOAc mixture (85:15) gave 21-Bromo-3β-ethynyl-3α-hydroxy-5α-pregnan-20-one (2.1 g).

b. 3α,21-Dihydroxy-3β-ethynyl-5α-pregnan-20-one

A solution of the above bromo derivative (2.1 g, 5 mmol) in acetone (40 mL) was treated with trifluoroacetic acid (3.8 mL, 50 mmol) and triethylamine (5.5 mL). The mixture was refluxed for 30 min. and then trifluoroacetic acid sodium salt (10 g) was added in parts over a period of 10 hr. After cooling to room temperature, a solution of sat. $NaHCO_3$ was added. The solvent was removed and the residue was extracted with EtOAc. The organic layer was washed with water, and brine. After drying over anhyd. $MgSO_4$ the solution was filtered and evaporated to yield the crude product (1.6 g). This crude product was then dissolved in a small amount of $CH_2Cl_2$ and poured on a column of silica gel. Elution with hexane:EtOAc mixture (7.3) gave 3α,21-dihydroxy-3β-ethynyl-5α-pregnan-20-one (1.5 g), mp 214–218° C.; TLC $R_f$ (hexane:acetone 7:3)=0.33.

Example 50

3β-(4'-Acetylphenylethynyl)-3α,21-dihydroxy-5β-pregnan-20-one

A solution of 4-iodoacetophenone (962 mg, 4 mmol), 3α,21-dihydroxy-3β-ethynyl-5α-pregnan-20-one (1.2 g, 4 mmol) in dry degassed triethylamine (7 mL) was stirred under argon at 23° C. Bis(triphenyl-phosphine)palladium chloride (15 mg) and CuI (5 mg) were added and the mixture was stirred at this temp. for 45 min. $CH_2Cl_2$ (25 mL) was added and the mixture was stirred at 23° C. for 1.5 hr. TLC showed 100% conversion of the starting material, hence, the solvent was removed and the residue was purified by chromatography on silica gel. Elution with hexane:acetone (7:3) gave 3β-(4'-acetylphenylethynyl)-3α,21-dihydroxy-5β-pregnan-20-one (750 mg) as a colorless solid; mp 222–225° C., TLC $R_f$ (hexane:acetone 4:1)=0.13.

Example 51

3β-(4'-Acetylphenylethynyl)-3α,21-dihydroxy-5β-pregnan-20-one 21-hemisuccinate sodium salt a. 3β-(4'-Acetylphenylethynyl)-3α,21-dihydroxy-5β-pregnan-20-one21-hemisuccinate A solution of 3β-(4'-acetylphenylethynyl)-3α,21-dihydroxy-5β-pregnan-20-one (276 mg, 1.4 mmol) in pyridine (4 mL) was treated with succinic anhydride (680 mg, 2.7 mmol) and 4-(N,N-dimethyl)aminopyridine (20 mg). The mixture was heated to 70–75° C. for 2.5 hr. TLC showed 100% conversion. Pyridine was removed in vacuo and the residue was extracted with EtOAc. The organic layer was washed with 0.1N HCl, water, and brine. After drying over anhyd. $MgSO_4$ the solution was filtered and evaporated to yield the crude product. This crude product was then dissolved in a small amount of $CH_2Cl_2$ and poured on a column of silica gel. Elution with hexane:acetone mixture (7:3) gave 3β-(4'-acetylphenylethynyl)-3α,21-dihydroxy-5β-pregnan-20-one 21-hemisuccinate (400 mg).

b. 3β-(4'-Acetylphenylethynyl)-3α,21-dihydroxy-5β-pregnan-20-one 21-hemisuccinate sodium salt A mixture of the above hemisuccinate (400 mg, 0.7 mmol), $NaHCO_3$ (60 mg, 0.7 mmol), water (3 mL), and $CH_2Cl_2$ (5 mL) was stirred at room temperature for 1 hr. The solvent was removed and the residue was freeze-dried to yield the sodium salt as a colorless solid (390 mg).

Example 52

3α-Hydroxy-3β-(3-pyridyl)ethynyl-5β-pregnan-20-one

A solution of 3-bromopyridine (70 mg, 0.44 mmol), 3β-ethynyl-3α-hydroxy-5α-pregnan-20-one (150 mg, 0.44 mmol) in dry degassed diethylamine (1 mL) was stirred under argon at 23° C. Bis(triphenylphosphine)palladium chloride (10 mg) and CuI (5 mg) were added and the mixture was stirred at this temp. for 45 min. $CH_2Cl_2$ (4 mL) was added and the mixture was stirred at 23° C. for 1.5 hr. TLC showed 100% conversion of the starting material, hence, the solvent was removed and the residue was purified by chromatography on silica gel. Elution with hexane:acetone (3:1) gave 3α-hydroxy-3β-(3-pyridyl)ethynyl-5β-pregnan-20-one (30 mg) as a colorless solid; mp 230–35° C., TLC $R_f$ (hexane:acetone 7:3)=0.24.

Example 53

21-Bromo-3α-Hydroxy-3β-(3-hydroxypropyn-1-yl)-5β-pregnan-20-one

A solution of 3α-hydroxy-3β-(3-hydroxypropyn-1-yl)-5β-pregnan-20-one (483 mg, 1.3 mmol) in MeOH (20 mL) was heated to 33° C. and was treated with two drops of HBr (48%), followed by bromine (1.43 mmol, 0.73 mL). The mixture was stirred at 37° C. for 1 hr and was poured into ice-water. The separated solid was collected by filtration, washed with water, and dried. This semi-dried solid was then dissolved in EtOAc and dried over anhyd. $MgSO_4$. Filtration and removal of the solvent gave the crude 21-bromo-3α-hydroxy-3β-(3-hydroxypropyn-1-yl)-5β-pregnan-20-one (322 mg).

EXAMPLE 54

3α-Hydroxy-3β-(3-hydroxypropyn-1-yl)-21-(1,2,3-triazol-2-yl)-5β-pregnan-20-one and 3α-hydroxy-3β-(3-hydroxypropyn-1-yl)-21-(1,2,3-triazol-1yl)-5β-pregnan-20-one A suspension of NaH (30 mg, 95%, 1.2 mmol) in THF (10 mL) was treated with a solution of 1,2,3-triazole (69 mg, 1mmol) in THF (10 mL) at room temperature. After stirring the mixture for 30 min. a solution of the crude bromo derivative of Example 53 (162 mg, 0.37 mmol) in THF (10 mL) was added. The stirring was continued at room temperature for 1.5 hr. Sat. NH$_4$Cl soln. was added and the solvent was removed. The residue was extracted with EtOAc. The organic layer was washed with water, and brine. After drying over anhyd. MgSO$_4$ the solution was filtered and evaporated to yield the crude product (250 mg). This crude product was then dissolved in a small amount of CH$_2$Cl$_2$ and poured on a column of silica gel. Elution with CH$_2$Cl$_2$:acetone (6:4) mixture gave 3α-hydroxy-3β-(3-hydroxypropyn-1-yl)-21-(2H-1,2,3-triazol-2-yl)-5β-pregnan-20-one (40 mg) as a first fraction; mp 188–191° C.; TLC R$_f$ (CH$_2$Cl$_2$:acetone 6:4) 0.56. Further elution with the same solvent mixture yielded 3α-hydroxy-3β-(3-hydroxypropyn-1-yl)-21-(1H-1,2,3-triazol-1-yl)-5β-pregnan-20-one (40 mg); mp 135–140° C.; TLC R$_f$ (CH$_2$Cl$_2$:acetone 6:4) 0.34.

EXAMPLE 55

3β-(4'-Hydroxy-1'-butynyl)-3α-hydroxy-5β-pregnan-11,20-dione

A solution of 3-butyn-1-ol (0.4 mL, 5.2 mmol) in dry THF (15 mL) was treated with n-BuLi (4 mL, 2.5M in THF, 10 mmol) at −65° C. After stirring the mixture at −78° C. for 0.5 hr, a solution of 5β-pregnan-3,11,20-trione, cyclic 20-(1,2-ethanediyl acetal) (800 mg, 2.14 mmol) in THF (20 mL) was added and the mixture was stirred at −78° C. for 1 hr. The cooling bath was removed and the stirring was continued at room temperature for 45 min. The mixture was then quenched with NH$_4$Cl solution (5 mL). The solvent was removed the residue was then dissolved in acetone (30 mL). After adding 2N HCl (7 mL) the solution was stirred at rt for 15 min. Sat. NaHCO$_3$ soln. was added to neutralize the acid. The solvents were removed and the residue was extracted with EtOAc. The organic layer was washed with water, and brine. After drying over anhyd. MgSO$_4$ the solution was filtered and evaporated to yield the crude product. This crude product was then dissolved in a small amount of CH$_2$Cl$_2$ and poured on a column of silica gel. Elution with toluene:acetone mixture (3:1) gave the unreacted butynol as a first fraction. Further elution with the same solvent mixture yielded 3α-(4'-hydroxy-1'-butynyl)-3β-hydroxy-5β-pregnan-11,20-dione (100 mg), and then 3β-(4'-hydroxy-1'-butynyl)-3α-hydroxy-5β-pregnan-11,20-dione (400 mg) as a colorless solid; mp 158–162° C.; TLC R$_f$ (toluene:acetone 3:1)=0.16.

It will be obvious to one skilled in the art that the above described compounds may be present as mixtures of diastereomers which may be separated into individual diastereomers. Resolution of the diastereomers may be conveniently accomplished by gas or liquid chromatography or isolation from natural sources. Unless otherwise specified herein, reference in the specification and claims to the compounds of the invention, as discussed above, is intended to include all isomers, whether separated or mixtures thereof.

Where isomers are separated, the desired pharmacological activity will often predominate in one of the diastereomers. As disclosed herein, these compounds display a high degree of sterospecificity. In particular, those compounds have the greatest affinity for the GABA receptor complex are those with 3β-substituted-3α-hydroxypregnane steroid skeletons.

The compounds of and used in the invention, that being the nontoxic, pharmaceutically acceptable, natural and synthetic, direct acting and "prodrug" forms of progesterone, deoxycorticosterone, and androstane metabolites, have hitherto unknown activity in the brain at the GABA$_A$ receptor complex. The present invention takes advantage of the discovery of this previously unknown mechanism and activity.

The pharmaceutical compositions of this invention are prepared in conventional dosage unit forms by incorporating an active compound of the invention or a mixture of such compounds, with a nontoxic pharmaceutical carrier according to accepted procedures in a nontoxic amount sufficient to produce the desired pharmacodynamic activity in a subject, animal or human. Preferably, the composition contains the active ingredient in an active, but nontoxic amount, selected from about 1 mg to about 500 mg of active ingredient per dosage unit. This quantity depends on the specific biological activity desired and the condition of the patient. Desirable objects of the compositions and methods of this invention are in the treatment of stress, anxiety, PMS, PND, and seizures such as those caused by epilepsy to ameliorate or prevent the attacks of anxiety, muscle tension, and depression common with patients suffering from these central nervous system abnormalities. An additional desirable object of the composition and methods is to treat insomnia and produce hypnotic activity. Another desirable object of the compounds an methods is to induce anesthesia, particularly by intravenous administration.

The pharmaceutical carrier employed may be, for example, either a solid, liquid, or time release (see e.g. Remington's Pharmaceutical Sciences, 14th Edition, 1970). Representative solid carriers are lactose, terra alba, sucrose, talc, gelatin, agar, pectin, acacia, magnesium stearate, stearic acid, microcrystalline cellulose, polymer hydrogels and the like. Typical liquid carriers are propylene glycol, glycofurol, aqueous solutions of cyclodextrins, syrup, peanut oil, and olive oil and the like emulsions. Similarly, the carrier or diluent may include any time-delay material well known to the art, such as glycerol monostearate or glycerol distearate alone or with wax, microcapsules, microspheres, liposomes, and/or hydrogels.

A wide variety of pharmaceutical forms can be employed. Thus, when using a solid carrier, the preparation can be plain milled micronized, in oil, tableted, placed in a hard gelatin or enteric-coated capsule in micronized powder or pellet form, or in the form of a troche or lozenge. The compounds of and used in the invention may also be administered in the form of suppositories for rectal administration. Compounds may be mixed in material such as cocoa butter and polyethylene glycols or other suitable non-irritating material which is solid in rt but liquid at the rectal temperature. When using a liquid carrier, the preparation can be in the form of a liquid, such as an ampule, or as an aqueous or nonaqueous liquid suspension. Liquid dosage forms also need pharmaceutically acceptable preservatives and the like. In addition, because of the low doses that will be required as based on the data disclosed herein, parental administration, nasal spray, sublingual and buccal administration, and timed release skin patches are also suitable pharmaceutical forms for topical administration.

The method of producing anxiolytic, anticonvulsant, mood altering (such as anti-depressant) or hypnotic activity, in accordance with this invention, comprises administering to a subject in need of such activity a compound of the invention, usually prepared in a composition as described above with a pharmaceutical carrier, in a nontoxic amount sufficient to produce said activity.

During menses, the levels of excreted metabolites vary approximately fourfold (Roscixzewska, et al.). Therefore, therapy for controlling symptoms involves maintaining the patient at a higher level of progesterone metabolites than normal in the premenstrual state of PMS patients. Plasma levels of active and major metabolites are monitored during pre-menses and post-menses of the patient. The amount of the compounds of the invention administered, either singly or as mixtures thereof are thus calculated to reach a level which will exert $GABA_A$-receptor activity equal or higher than the level of progesterone metabolites in the normal subject during the premenses state.

The route of administration may be any route that effectively transports the active compound to the $GABA_A$ receptors that are to be stimulated. Administration may be carried out parenterally, enterally, rectally, intravaginally, intradermally, intramuscularly, sublingually, or nasally; the oral, intramuscular, and dermal routes are preferred. For example, one dose in a skin patch may supply the active ingredient to the patient for a period of up to one week. However, the parenteral route is preferred for status epilepticus.

Potency and Efficacy at the GR Site

The in vitro and in vivo experimental data show that the naturally-occurring metabolites of progesterone/deoxycorticosterone and their derivatives interact with high affinity at a novel and specific recognition site on the GR complex to facilitate the conductance of chloride ions across neuronal membranes sensitive to GABA (Gee et al., 1987 Harrison et al., 1987).

To those skilled in the art, it is known that the modulation of [$^{35}$S]t-butylbicyclophosphorothionate ([$^{35}$S]TBPS) binding is a measure of the potency and efficacy of drugs acting at the GR complex, which drugs may be of potential therapeutic value in the treatment of stress, anxiety, and seizure disorders (Squires, R. F., et al., "[$^{35}$S]t-Butylbicyclophophorothionate binds with high affinity to brain-specific sites coupled to a gamma aminobutyric acid-A and ion recognition site," Mol, Pharmacol., 23:326, 1983; Lawrence, L. J., et al., "Benzodiazepine anticonvulsant action: gamma-aminobutyric acid-dependent modulation of the chloride ionophore," Biochem. Biophys. Res. Comm., 123:1130–1137, 1984; Wood, et al., "In vitro characterization of benzodiazepine receptor agonists, antagonists, inverse agonists and agonist/antagonists," Pharmacol, Exp. Ther., 231:572–576, 1984). We performed several experiments to determine the nature of the modulation of [$^{35}$S] TBPS as affected by the compounds of the invention. We found that these compounds interact with a novel site on the GR complex which does not overlap with the barbiturate, the benzodiazepine or any other previously known sites. Furthermore, these compounds have high potency and efficacy at the GR complex, with stringent structural requirements for such activity. Preferred compounds which are useful in the present invention have an $IC_{50}$ of 2 μM or less in the [$^{35}$S]TBPS binding assay described herein below.

The procedure for performing this assay are fully discussed in: (1) Gee, et al., 1987; and (2) Gee, K. W., L. J. Lawrence, and H. I. Yamamura, "Modulation of the chloride ionophore by benzodiazepine receptor ligands: influence of gamma-aminobutyric acid and ligand efficacy," Molecular Pharmacology 30:218, 1986. These procedures were performed as follows:

Brains from male Sprague-Dawley rats were removed immediately following sacrifice and the cerebral cortices dissected over ice. A $P_2$ homogenate was prepared as previously described (Gee, et al., 1986). Briefly, the cortices were gently homogenized in 0.32M sucrose followed by centrifugation at 1000×g for 10 minutes. The supernatant was collected and centrifuged at 9000×g for 20 minutes. The resultant $P_2$ pellet was suspended as a 10% (original wet weight/volume) suspension in 50 mM Na/K phosphate buffer (pH 7.4) 200 mM NaCl to form the homogenate.

One hundred microliter (ml) aliquots of the $P_2$ homogenate (0.5 milligrams (mg) protein) were incubated with 2 nanomolar (nM) [$^{35}$S]TBPS (70–110 curies/millimole;, New England Nuclear, Boston, Mass.) in the presence of absence of the naturally occurring steroids or their synthetic derivatives to be tested. The tested compounds were dissolved in dimethylsulfoxide (Baker Chem. Co., Phillipsbury, N.J.) and added to the incubation mixture in 5 μL aliquots. The incubation mixture was brought to a final volume of 1 mL with buffer. Non-specific binding was defined as binding in the presence of 2 mM TBPS. The effect and specificity of GABA (Sigma Chem. Co., St. Louis, Mo.) was evaluated by performing all assays in the presence of GABA plus (+)bicuculline (Sigma Chem. Co.). Incubations maintained at 25° C. for 90 minutes (steady state conditions) were terminated by rapid filtration through glass fiber filters (No. 32, Schleicher and Schuell, Keene, N. H.). Filter-bound radioactivity was quantitated by liquid scintillation spectrophotometry. Kinetic data and compound/[$^{35}$S]TBPS dose-response curves were analyzed by nonlinear regression using a computerized iterative procedure to obtain rate constants and $IC_{50}$ (concentration of compound at which half-maximal inhibition of basal [$^{35}$S]TBPS binding occurs) values.

Figure 1B:
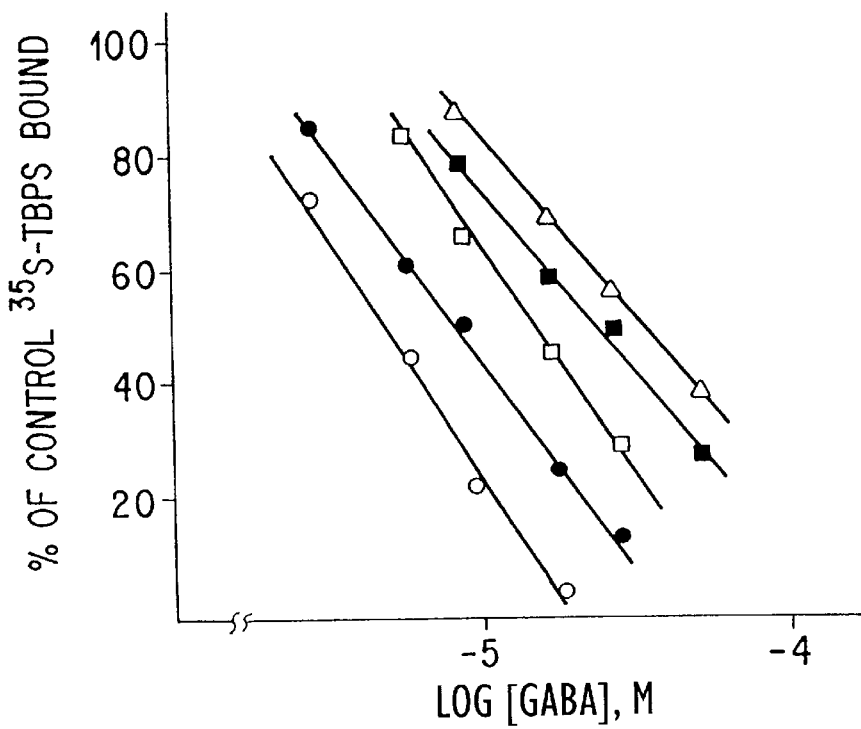

The experimental data obtained for this assay are also published in Gee, et al., 1987. The data discussed in this reference are shown as plots in FIGS. 1A and 1B. These plots show the effect of (+)bicuculline on the pregnane steroid alphaxalone (1A) and GABA (1B) modulation of 2 nM [$^{35}$S] TBPS binding to rat cerebral cortex. In these figures, (○) represents control without bicuculline; (●) represents 0.5 μM bicuculline; (□) represents 1.0 μM bicuculline; (■) represents 2.0 μM bicuculline; and (Δ) represents 3.0 μM bicuculline. In this experiment, the effect of (+)bicuculline on the ability of alphaxalone or GABA to inhibit the binding of [$^{35}$S]TBPS was determined. Bicuculline is known to be a competitive antagonist of GABA and a classical parallel shift in the dose-response curves is observed in FIG. 1B. In contrast, the steroid binding site identified by this work is distinct from the GABA/bicuculline site in FIG. 1A. The shift in dose-response curves induced by bicuculline when the inhibition of [$^{35}$S] TBPS binding is caused by alphaxalone is not parallel. This indicates that the GABA and steroid sites do not overlap.

Figure 2:
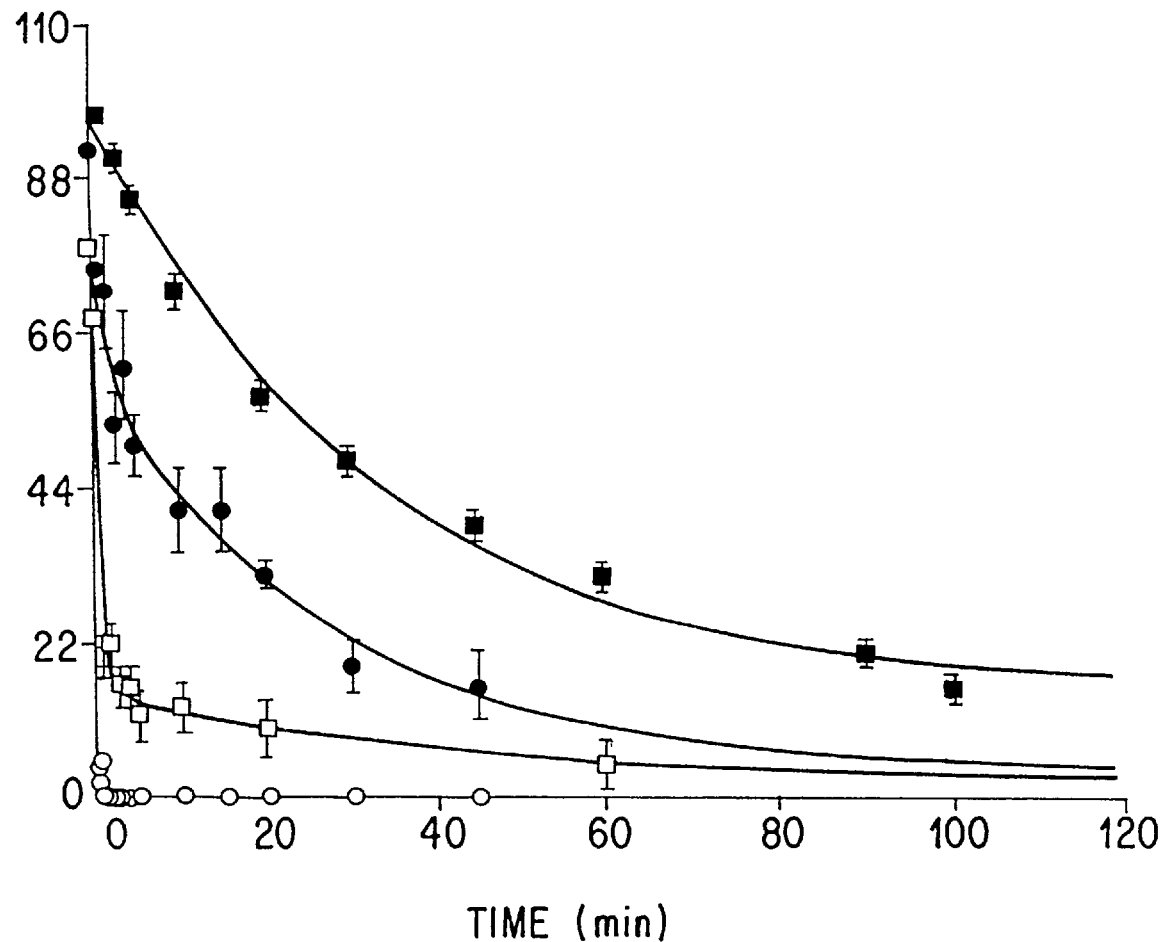
FIG. 2 shows time courses for the dissociation of 2 nM [$^{35}$S] TBPS from rat cortical $P_2$ homogenates initiated by the addition of 2 μM TBPS (■), 1 μM 3α5αP (□), 100 μM Na pentobarbital (●), and 1 μM 3α5αP+100 μM Na pentobarbital (○).

A second set of experiments were performed to demonstrate that steroids, barbiturates and benzodiazepines do not share common binding site on the GABA receptor. FIG. 2 shows the time course for the dissociation of [$^{35}$S] TBPS from rat cortical $P_2$ homogenates initiated by the addition of 2 μM TBPS(■), 1 μM 3α-hydroxy-5α-pregnan-20-one (□), 100 μM Na pentobarbital (●) and 1 μM 3α-OH-5α-pregnan-20-one+100 μM Na pentobarbital (○). The assay was performed in accordance with the procedures outlined above. These kinetic data show that the dissociation of [$^{35}$S] TBPS binding initiated by saturating concentration of 3α-hydroxy-5α-pregnan-20-one is potentiated by 100 μM Na pentobarbital. This effect is an indication that 3α-OH-5α-pregnan-20-one (steroid) and pentobarbital (barbiturate) bind to independent sites.

Figure 3:
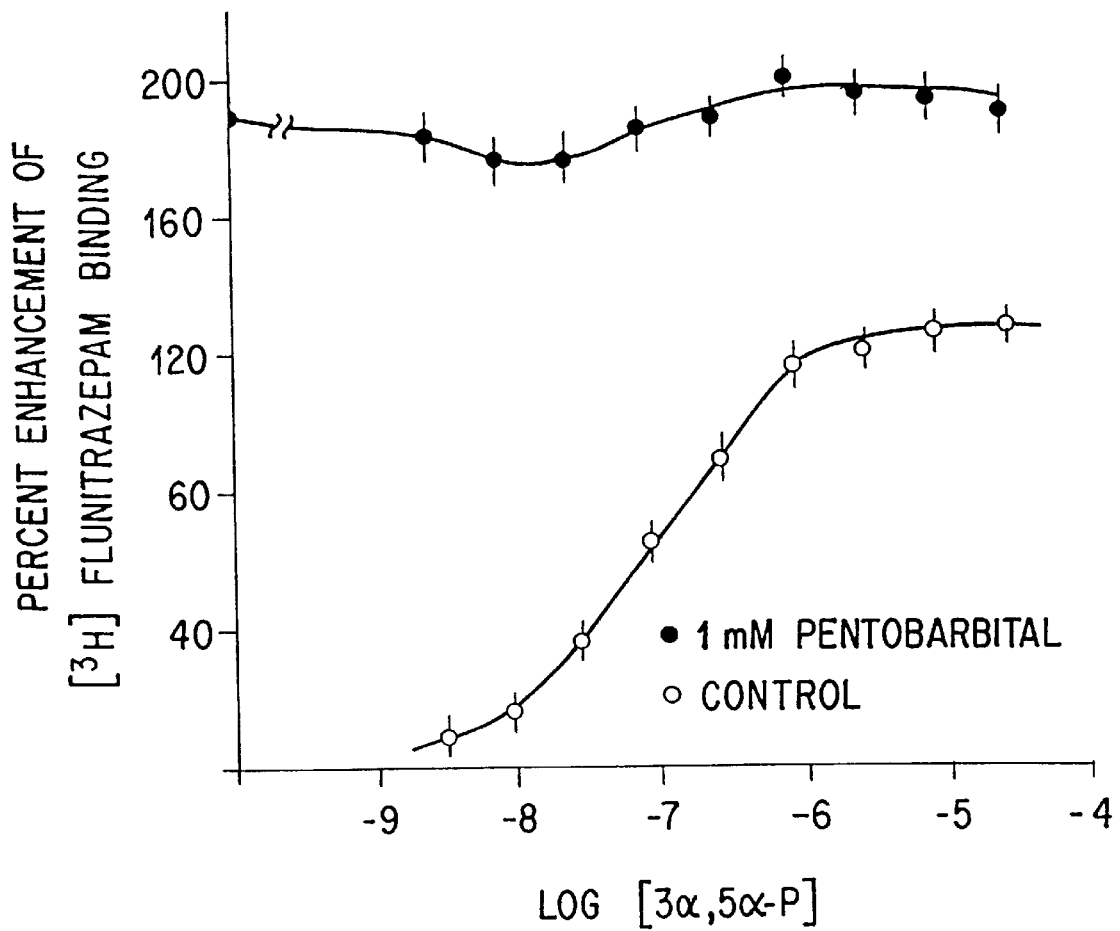
FIG. 3 is a plot showing the effect of a single dosage of pentobarbital on 3α-OH-5α-pregnan-20-one (3α-5α-P) modulation of [$^3$H]-flunitrazepam binding in rat hippocampal homogenates.

The third set of experiments examined the interactions between 3α-hydroxy-5α-pregnan-20-one and Na pentobarbital in the potentiation of ($^3$H) flunitrazepam (FLU) binding. These experiments further support the claim that steroids do not share common site of action with benzodiazepines and barbiturates. In this series of experiments, the effect of varying concentrations of 3α-hydroxy-5α-pregnan-20-one on ($^3$H) FLU binding in the presence or absence of a maximally stimulating concentration of Na pentobarbital. Since Na pentobarbital has greater maximum efficacy than that of 3α-hydroxy-5α-pregnan-20-one in potentiating ($^3$H) FLU binding, 3α-hydroxy-5α-pregnan-20-one should ultimately antagonize the effect of Na pentobarbital if the two interact competitively on the same site. This is not what was observed (FIG. 3). Thus, the data further support our conclusion that certain steroids including the compounds of and used in the invention interact with a novel site distinct from the barbiturate or BZ regulatory site on the GR complex. Because of this independent site of action, it is anticipated that these steroid compounds will have therapeutic profiles different from those of barbiturates and BZs.

Figure 4:
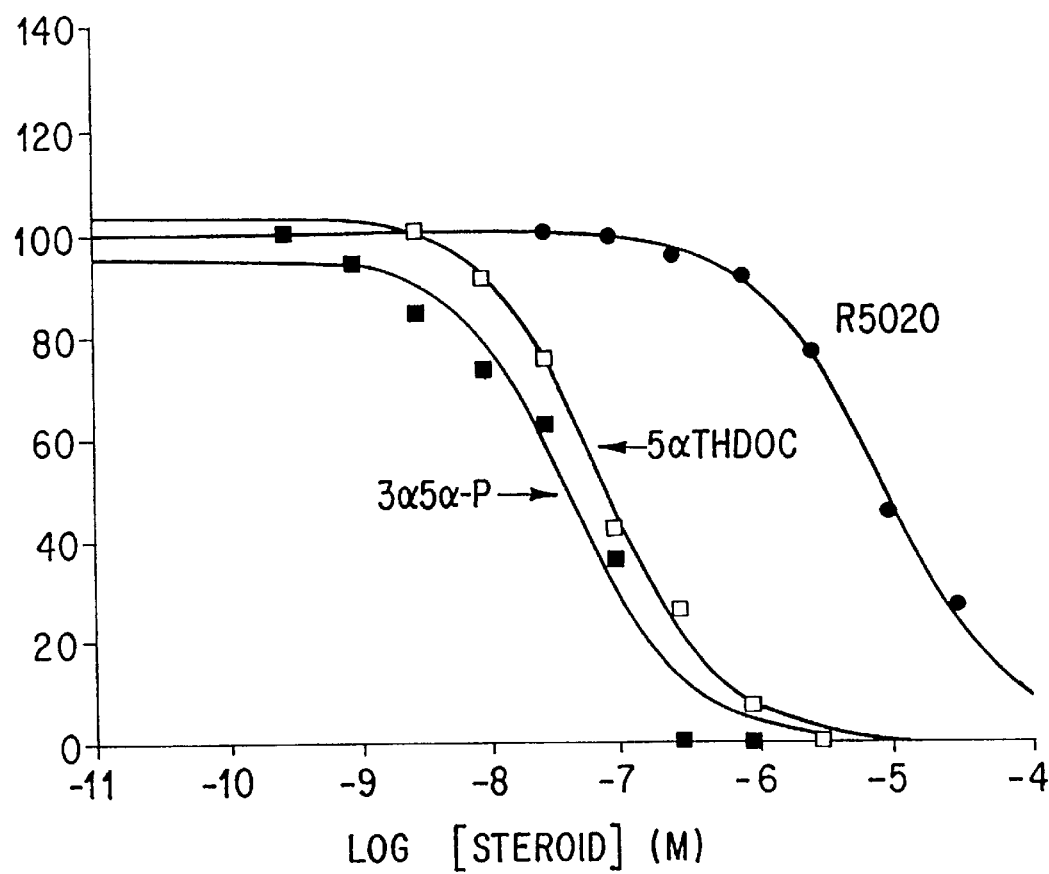
FIG. 4 is a plot of the effect of 3α-hydroxy-5α-pregnan-20-one, 3α,21-dihydroxy-5α-pregnan-20-one (5α-THDOC) and R5020 (promegesterone) on inhibiting [$^{35}$S] TBPS binding in rat cerebral cortex homogenate.

Various compounds were screened to determine their potential as modulators of [$^{35}$S]TBPS binding in vitro. These assays were performed in accordance with the above discussed procedures. Based on these assays, we have established the structure-activity requirements for their specific interaction at the GR complex and their rank order potency and efficacy. FIG. 4 provides [$^{35}$S]TBPS inhibition of curves of 3α-hydroxy-5α-pregnan-20-one (3α,5α-P), 3α,21-dihydroxy-5α-pregnan-20-one (5α-THDOC) and R5020 (promogesterone) as experimental examples, while Table 1 provides $IC_{50}$ and maximum inhibition of numerous compounds, including examples of those claimed in the application. $IC_{50}$ is defined as concentration of compounds to inhibit 50% of control [$^{35}$S]TBPS binding. It is an indication of a compound's in vitro potency. Maximum inhibition is an indication of a compound's in vitro efficacy.

TABLE 1

| COMPOUND | $IC_{50}$ (nM) | IMAX (%) |
|---|---|---|
| 3β-(4'-Acetylphenylethynyl)-3α,21-dihydroxy-5α-pregnan-20-one | 4 | 92 |
| 3β-(4'-Acetylphenyl)ethynyl-3α-hydroxy-5α-pregnan-20-one | 5 | 93 |
| 3β-(4'-Acetylphenyl)ethynyl-3α-hydroxy-5α-19-norpregnan-20-one | 6 | 90 |
| 3β-(4'-Carboxyphenyl)ethynyl-3α-hydroxy-5α-pregnan-20-one ethyl ester | 7 | 79 |
| 3β-(4'-Carboxyphenyl)ethynyl-3α-hydroxy-5β-pregnan-20-one ethyl ester | 8 | 98 |
| 3β-(4-Hydroxybutyn-1-yl)-3α-hydroxy-5β-pregnan-20-one | 13 | 103 |
| 3β-(4'-Acetylphenyl)ethynyl-3α-hydroxy-5β-pregnan-20-one | 14 | 103 |
| 3β-(4'-Carboxyphenyl)ethynyl-3α-hydroxy-19-nor-5β-pregnan-20-one ethyl ester | 15 | 94 |
| 3β-(4-Acetoxybutyn-1-yl)-3α-hydroxy-5β-pregnan-20-one | 20 | 96 |
| 3β-(4'-Acetylphenylethynyl)-3α,21-dihydroxy-5β-pregnan-20-one | 22 | 99 |
| 3β-(4-Hydroxybutyn-1-yl)-3α-hydroxy-5β-19-norpregnan-20-one | 22 | 102 |
| 3β-(3'-Methoxy-1'-propynyl)-3α-hydroxy-5β-pregnan-20-one | 27 | 105 |
| 3β-(4'-Dimethylaminophenyl)ethynyl-5β-pregnan-20-one | 28 | 77 |
| 3β-[3-(2-propynyloxy)propyn-1-yl]-3α-hydroxy-5β-pregnan-20-one | 28 | 105 |
| 3β-(4-Hydroxybutyn-1-yl)-3α-hydroxy-5α-pregnan-20-one | 35 | 95 |
| 3α-Hydroxy-5α-pregnan-20-one | 37 | 95 |
| 3β-(4'-Biphenyl)ethynyl-3α-hydroxy-5β-pregnan-20-one | 43 | 83 |
| 3α-Hydroxy-3β-(4'-nitrophenyl)ethynyl-5β-pregnan-20-one | 46 | 103 |
| 3α-Hydroxy-21-(2H-1,2,3,4-tetrazol-2-yl)-5β-pregnan-20-one | 46 | 78 |
| 3α-Hydroxy-3β-(4'-methoxyphenyl)ethynyl-5β-pregnan-20-one | 47 | 89 |
| 3β-(4'-Trifluoromethylphenyl)ethynyl-3α-hydroxy-5β-pregnan-20-one | 52 | 87 |
| 3β-(5-Acetylthien-2-yl)ethynyl-3α-hydroxy-5β-pregnan-20-one | 52 | 89 |
| 21-(1-Benzimidazolyl)-3α-hydroxy-5β-pregnan-20-one | 53 | 100 |
| 3β-(4-Hydroxybutyn-1-yl)-3α-hydroxy-21-(1-imidazolyl)-5β-pregnan-20-one | 54 | 93 |
| 3α-Hydroxy-21-(2H-1,2,3-triazol-2-yl)-5β-pregnan-20-one | 56 | 79 |
| 3β-(4'-Hydroxybutyn-1'-yl)-3α-hydroxy-21-(1,2,3-triazol-2-yl)-5β-19-norpregnan-20-one | 56 | 93 |
| 3β-(4'-Chlorophenyl)ethynyl-3α-hydroxy-5β-pregnan-20-one | 58 | 89 |
| 3β-(5'-Hydroxypentyn-1'-yl)-3α-hydroxy-5β-pregnan-20-one | 58 | 100 |
| 3α-Hydroxy-3β-(thien-2-yl)ethynyl-5β-pregnan-20-one | 59 | 100 |
| 3β-(3'-Acetylphenyl)ethynyl-3α-hydroxy-5β-pregnan-20-one | 62 | 100 |
| 3α-Hydroxy-21-[1H-(4-methyl-5-carboxyl)imidazol-1-yl)]-5β-pregnan-20-one | 62 | 100 |
| 3α-Hydroxy-3β-[3'-(2H-1,2,3-triazol-2-yl)-1-propynyl]-5β-pregnan-20-one | 66 | 98 |
| 3α-Hydroxy-21-(9H-1,2,3-purin-9-yl)-5β-pregnan-20-one | 69 | 59 |
| 3α-Hydroxy-3β-[4'(R/S)-hydroxypentynyl]-5β-pregnan-20-one | 71 | 103 |
| 3α-Hydroxy-21-(imidazol-1-yl)-5α-pregnan-20-one | 71 | 99 |
| 3α-Hydroxy-21-(imidazol-1-yl)-5β-pregnan-20-one | 73 | 57 |
| 3β-(4'-Cyanophenyl)ethynyl-3α-hydroxy-5β-pregnan-20-one | 73 | 92 |
| 3β,21-Dihydroxy-5α-pregnan-20-one(5α-THDOC) | 76 | 100 |
| 3α-Hydroxy-3β-(pentafluorophenyl)-ethynyl-5β-pregnan-20- | 79 | 69 |

TABLE 1-continued

| COMPOUND | IC$_{50}$ (nM) | IMAX (%) |
|---|---|---|
| one | | |
| 3β-(4'-Hydroxybutyn-1'-yl)-3α-hydroxy-21-(1,2,3-triazol-1-yl)-5β-pregnan-20-one | 79 | 96 |
| 3β-Ethynyl-3α-hydroxy-21-(1'-imidazolyl)-5β-pregnan-20-one | 80 | 103 |
| 3α-Hydroxy-3β-[3'-(1H-pyrazol-1-yl)-1'-propynyl]-5β-pregnan-20-one | 81 | 98 |
| 3α-Hydroxy-3β-methyl-21-(2H-1,2,3-triazol-2-yl)-5α-pregnan-20-one | 85 | 99 |
| 3β-[4'-(N,N-Diethylcarboxamidophenyl)ethynyl]-3α-hydroxy-5β-pregnan-20-one | 87 | 94 |
| 3α-Hydroxy-3β-(4'-methylphenyl)ethynyl-5β-pregnan-20-one | 88 | 84 |
| 3α-Hydroxy-3β-(6-oxo-1-heptynyl)-5β-pregnan-20-one | 90 | 101 |
| 3β-(4'-Hydroxybutyn-1'-yl)-3α-hydroxy-21-(1,2,4-triazol-1-yl)-5β-pregnan-20-one | 93 | 96 |
| 3β-(4'-Hydroxybutyn-1'-yl)-3α-hydroxy-21-(tetrazol-1-yl)-5β-pregnan-20-one | 93 | 101 |
| 3α-Hydroxy-3β-[4'(R/S)-hydroxypentynyl]-5β-pregnan-20-one | 94 | 104 |
| 3β-(5'-Acetoxypentyn-1'-yl)-3α-hydroxy-5β-pregnan-20-one | 96 | 98 |
| 3α-Hydroxy-21-(1H-3,5-dimethylpyrazolyl)-5β-pregnan-20-one | 96 | 77 |
| 3α-Hydroxy-21-(1'-imidazolyl)-3β-methyl-5α-pregnan-20-one | 97 | 95 |
| 3α-Hydroxy-3β-(phenylethynyl)-5β-pregnan-20-one | 98 | 101 |
| 3β-(4'-Hydroxybutyn-1'-yl)-3α-hydroxy-21-(1'-imidazolyl)-5β-19-norpregnan-20-one | 98 | 98 |
| 3α-Hydroxy-21-(1'-pyrazolyl)-5α-pregnan-20-one | 100 | 98 |
| 3β-(2'-Hydroxyphenyl)ethynyl-3α-hydroxy-5β-pregnan-20-one | 101 | 83 |
| 3α-Hydroxy-3β-(3'-phenyl-1'-propynyl)-5β-pregnan-20-one | 103 | 95 |
| 3β-Ethynyl-3α-Hydroxy-21-(1'-pyrazolyl)-5β-pregnan-20-one | 106 | 99 |
| Sodium S-[3α-hydroxy-3β-(4'-hydroxybutynyl)-5β-pregnan-20-on-21-yl] thiosulfate | 107 | 97 |
| 3α-Hydroxy-3β-(2'-pyridyl)ethynyl-5β-pregnan-20-one | 108 | 98 |
| 3β-(2.4-Difluorophenyl)ethynyl-3α-hydroxy-5β-pregnan-20-one | 109 | 102 |
| 3β-Benzyl-3α-hydroxy-5β-pregnan-20-one | 109 | 102 |
| 21-(1'-Benzimidazolyl)-3α-hydroxy-3β-methyl-5α-pregnan-20-one | 109 | 95 |
| 3α-Hydroxy-21-(1'-pyrazolyl)-3β-methyl-5α-pregnan-20-one | 115 | 98 |
| 3α-Hydroxy-3β-(5'-oxo-1-hexynyl)-5β-pregnan-20-one | 118 | 101 |
| 3α-Hydroxy-21-(pyrazol-1-yl)-5β-pregnan-20-one | 121 | 67 |
| 3β-(4'-Hydroxybutyn-1'-yl)-3α-hydroxy-21-(1,2,3-triazol-1-yl)-5β-19-norpregnan-20-one | 124 | 95 |
| 3α-Hydroxy-3β-methyl-21-(1',2',4'-triazolyl)-5α-pregnan-20-one | 125 | 105 |
| 3β-Ethynyl-3α-hydroxy-21-(1',2',4'-triazolyl)-5β-pregnan-20-one | 127 | 98 |
| 3β-(4'-Cyanobutynyl)-3α-hydroxy-5β-pregnan-20-one | 131 | 86 |
| Sodium S-[3α-hydroxy-3β-(methoxymethyl)-5β-pregnan-20-on-21-yl] thiosulfate | 132 | 103 |
| Sodium S-(3α-hydroxy-5α-pregnan-20-on-21-yl)thiosulfate | 133 | 90 |
| 3α-Hydroxy-3β-(2'-phenylethyl)-5β-pregnan-20-one | 135 | 98 |
| 3α-Hydroxy-3β-methyl-21-(1',2',3'-triazol-1'-yl)-5α-pregnan-20-one | 136 | 99 |
| 3α-Hydroxy-3β-[3'-hydroxypropynyl]-5β-pregnan-20-one | 137 | 93 |
| 3α-Hydroxy-3β-(3-pyridyl)ethynyl-5β-pregnan-20-one | 138 | 100 |
| 3α-Hydroxy-3β-[3'(RS)-hydroxybutynyl]-5α-pregnan-20-one | 144 | 99 |
| 3α-Hydroxy-3β-(4-pyridyl)ethynyl-5β-pregnan-20-one | 149 | 103 |
| 3α-Hydroxy-21-(1',2',4'-triazol-1-yl)-5β-pregnan-20-one | 151 | 60 |
| Sodium S-(3α-hydroxy-3β-methyl-5α-pregnan-20-on-21-yl)thiosulfate | 151 | 101 |
| 3β-(5'-Cyanopentynyl)-3α-hydroxy-5β-pregnan-20-one | 158 | 100 |
| 3β-(4'-Acetoxyacetylphenyl)ethynyl-3α-hydroxy-5β-pregnan-20-one | 171 | 91 |
| 3α-Hydroxy-3β-phenylpropyl-5β-pregnan-20-one | 173 | 92 |
| 3α-Hydroxy-3β-[4'(R/S)-hydroxypentynyl]-5α-pregnan-20-one | 178 | 101 |
| 3α-Hydroxy-3β-[3'(RS)-hydroxybutynyl]-5β-pregnan-20-one | 202 | 102 |
| 3β-(6-Hydroxyhexyn-1-yl)-3α-hydroxy-5β-pregnan-20-one | 222 | 99 |
| 3α-Hydroxy-21-[1H-(2-methyl)imidizol-1-yl]-5β-pregnan-20-one | 222 | 95 |
| 3β-(3'-Acetoxypropyn-1'-yl)-3α-hydroxy-5β-pregnan-20-one | 224 | 104 |
| 3α-hydroxy-21-(1'H-1,2,3,4-tetrazol-1'-yl)-5β-pregnan-20-one | 227 | 60 |
| 3α-Hydroxy-21-(2-formylimidazol-1-yl)-5β-pregnan-20-one | 213 | 81 |
| 3α-Hydroxy-3β-(2'-methoxyphenyl)ethynyl-5β-pregnan-20-one | 238 | 99 |

TABLE 1-continued

| COMPOUND | IC$_{50}$ (nM) | IMAX (%) |
|---|---|---|
| 3β-(4'-(hydroxy-1'-butynyl)-3α-hydroxy-5β-pregnan-11,20-dione | 268 | 102 |
| 3β-[(3',4'-Dimethoxyphenyl)ethynyl]-3α-hydroxy-5β-pregnan-20-one | 283 | 106 |
| 3α-Hydroxy-21-[1H-(4-nitro)imidazol-1-yl)]-5β-pregnan-20-one | 267 | 71 |
| Sodium S-(3α-hydroxy-5β-pregnan-20-on-21-yl)thiosulfate | 268 | 88 |
| 3β-(6'-Acetoxyhexyn-1'-yl)-3α-hydroxy-5β-pregnan-20-one | 306 | 99 |
| Sodium S-(3α-hydroxy-3β-trifluoromethyl-5β-19-norpregnan-20-on-21-yl) thiosulfate | 325 | 98 |
| 3α-Hydroxy-3β-phenyl-5β-pregnan-20-one | 382 | 86 |
| 3β-(3'-Hydroxyphenyl)ethynyl-3α-hydroxy-5β-pregnan-20-one | 407 | 99 |
| 3α-Hydroxy-3β-(3-hydroxypropyn-1-yl)-21-(1,2,3-triazol-2-yl)-5β-pregnan-20-one | 430 | 107 |
| 3α-Hydroxy-21-(7'H-purin-7'-yl)-5β-pregnan-20-one | 430 | 71 |
| 3α-Hydroxy-21-(1'-uracil)-5α-pregnan-20-one | 434 | 90 |
| 3α-Hydroxy-3β-[3'-(pyrid-4-yloxy)-1'-propynyl]-5β-pregnan-20-one | 465 | 94 |
| 3β-[2-(3',4'-Dimethoxyphenyl)ethyl]-3α-hydroxy-5β-pregnan-20-one | 507 | 66 |
| 3α-Hydroxy-3β-(3'-hydroxyphenyl)-ethynyl-5β-pregnan-20-one | 619 | 98 |
| 3α-Hydroxy-3β-[3'-(1H-1,2,3-triazol-1-yl)-1'-propynyl]-5β-pregnan-20-one | 655 | 102 |
| 3α-Hydroxy-3β-[3'-(1H-1,2,4-triazol-1-yl)-1'-propynyl]-5β-pregnan-20-one | 843 | 99 |
| 3α-Hydroxy-3β-(3-hydroxypropyn-1-yl)-21-(1,2,3-triazol-1-yl)-5β-pregnan-20-one | 1089 | 101 |
| 3β-[3'-(N,N-dimethylamino)-1'-propynyl]-3α-hydroxy-5β-pregnan-20-one | 1420 | 100 |
| 3β-(4'-Acetoxyphenyl)ethynyl-3α-hydroxy-5β-pregnan-20-one | 1430 | 100 |
| 3β-(4-Hydroxyphenyl)ethynyl-3α-hydroxy-5β-pregnan-20-one | 1550 | 88 |
| 3α-Hydroxy-2β-morpholinyl-21-(1H-1,2,4-tirazol-1-yl)-5α-pregnan-20-one | 1553 | 97 |
| 3α-Hydroxy-3β-(3'-oxopropynyl)-5β-pregnan-20-one | 1720 | 76 |
| 3β-(4'-Carboxamidophenyl)ethynyl-3α-hydroxy-5β-pregnan-20-one | 2240 | 98 |
| 3β-(4'-Carboxamidobutynyl)-3α-hydroxy-5β-pregnan-20-one | 2340 | 102 |
| 3α-Hydroxy-3β-(3'-oxobutynyl)-5β-pregnan-20-one | 2690 | 107 |
| 3α-Hydroxy-3β-[3'-(N-imidazolyl)-1'-propynyl]-5β-pregnan-20-one | 2720 | 107 |
| 5β-(5'-Carboxamidopentynyl)-3α-hydroxy-5β-pregnan-20-one | 3090 | 102 |
| Progesterone | 5200 | 100 |
| 3α-Hydroxy-3β-[3'-oxobutynyl]-5α-pregnan-20-one | 6510 | 104 |
| 3β-(4'-Aminophenyl)ethynyl-3β-hydroxy-5β-pregnan-20-one | 22500 | 103 |
| 3β-Hydroxy-5α-pregnan-20-one (Allopregnanolone) | >10$^6$ | 33 |
| 4-Pregnen-11β-21-diol-3,20-dione (Corticosterone) | >10$^6$ | 30 |
| 17β-Estradiol | na[a] | 0 |
| Cholesterol | na | 0 |

[a]na = not active

Figure 5:
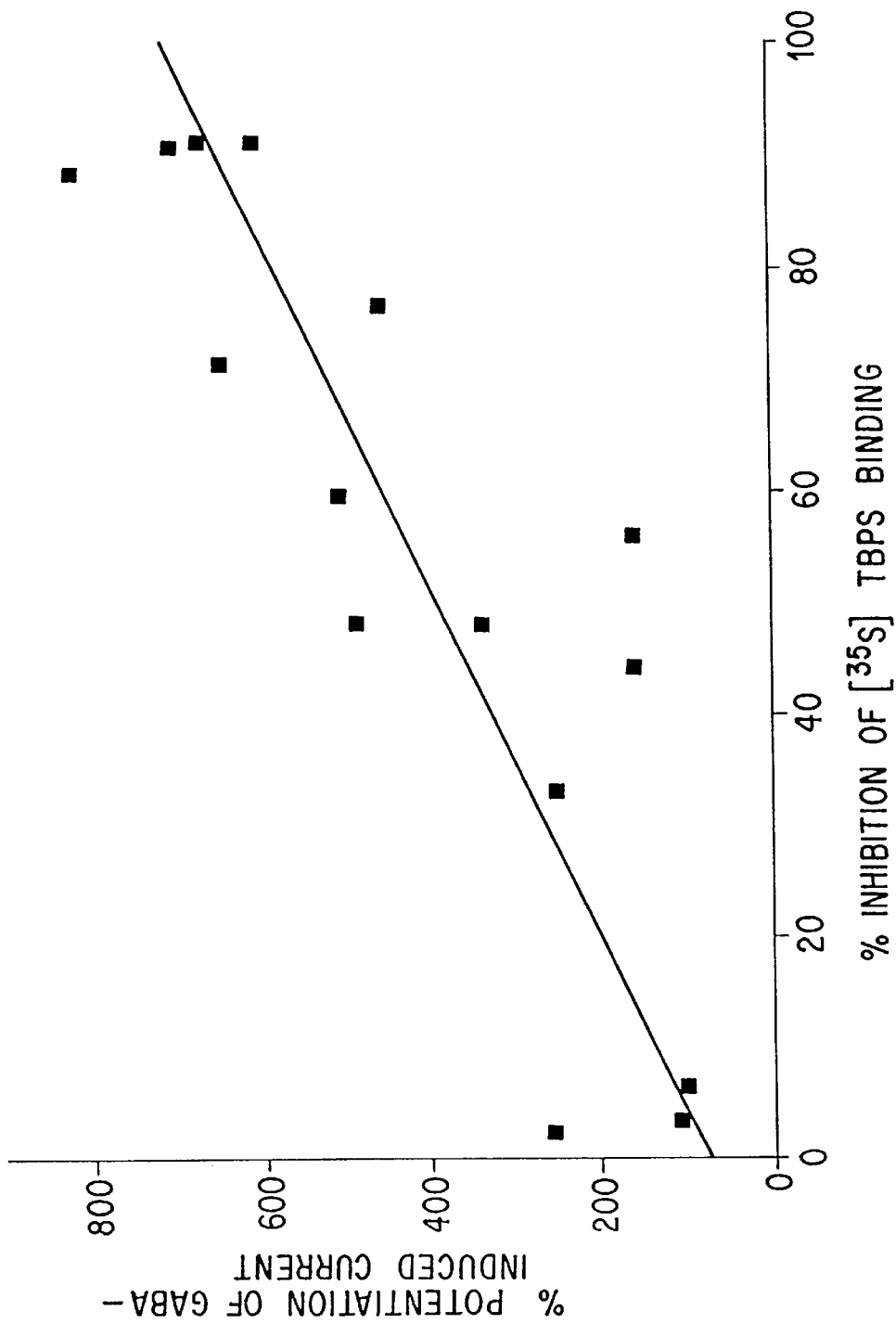
FIG. 5 is a plot of the correlation between TBPS binding and electrophysiological activity of 15 different 3α-hydroxylated steroids.

As can be seen from FIG. 4 and Table 1, 3α-hydroxy-5α-pregnan-20-one, 3α,21-dihydroxy-5α-pregnan-20-one and compounds of and used in the invention have low IC$_{50}$, which is the concentration necessary to achieve 50% maximal inhibition of [$^{35}$S]TBPS binding, while compounds such as sex steroids (R5020, estradiol and progesterone), glucocorticoids (corticosterone) and cholesterol having a high IC$_{50}$ are essentially inactive. Thus, it is anticipated that hormonal steroids and cholesterol per se will not have any therapeutic value for the indications described herein. In order to distinguish this unique class of steroids from hormonal steroids, they are now termed neuroactive steroids. However, sex steroids such as progesterone can be metabolized in the body to steroids similar to 3α-hydroxy-5α-pregnan-20-one. Thus, progesterone can be considered as a prodrug. The TBPS data correlates with data on $^{36}$Cl ion uptake-potentiated by various 3α-hydroxylated steroids described in Purdy R. H., et al., "Synthesis, Metabolism, and Pharmacological Activity of 3α-Hydroxy Steroids Which Potentiate GABA-Receptor-Mediated Chloride Ion Uptake in Rat Cerebral Cortical Synaptoneurosomes," J. Med. Chem 33: 1572–1581 (1990), incorporated herein by reference and these data also correlate with electrophysiological data obtained by measuring steroid's activity to potentiate GABA-induced current in oocytes injected with human GABA receptors as shown in FIG. 5. This indicates that the TBPS assay is an approximate measurement of steroids ability to allosterically modulate Cl$^-$ channel activity.

Compounds with Limited Efficacy

In as much as the desired therapeutical activity should be available to the patient with the least undesirable side effects, a notable aspect of this invention involves the discovery of agonists with partial activity in those compounds with a 5α-pregnan-3α,20α-diol, 5β-pregnan-3α, 20β-diol group or the derivatives and prodrugs of these compounds. In addition, a subset of neuroactive steroids other than these two groups also show partial efficacy in TBPS assay (Table 1). For the patients who desire amelioration of anxiety or convulsions, hypnosis is undesired. For the patients who desire amelioration of insomnia, anesthetic is undesired. The compounds and activities described as agonists with partial activity expected to have the desired effect with minimal undesired effect.

Figure 6:
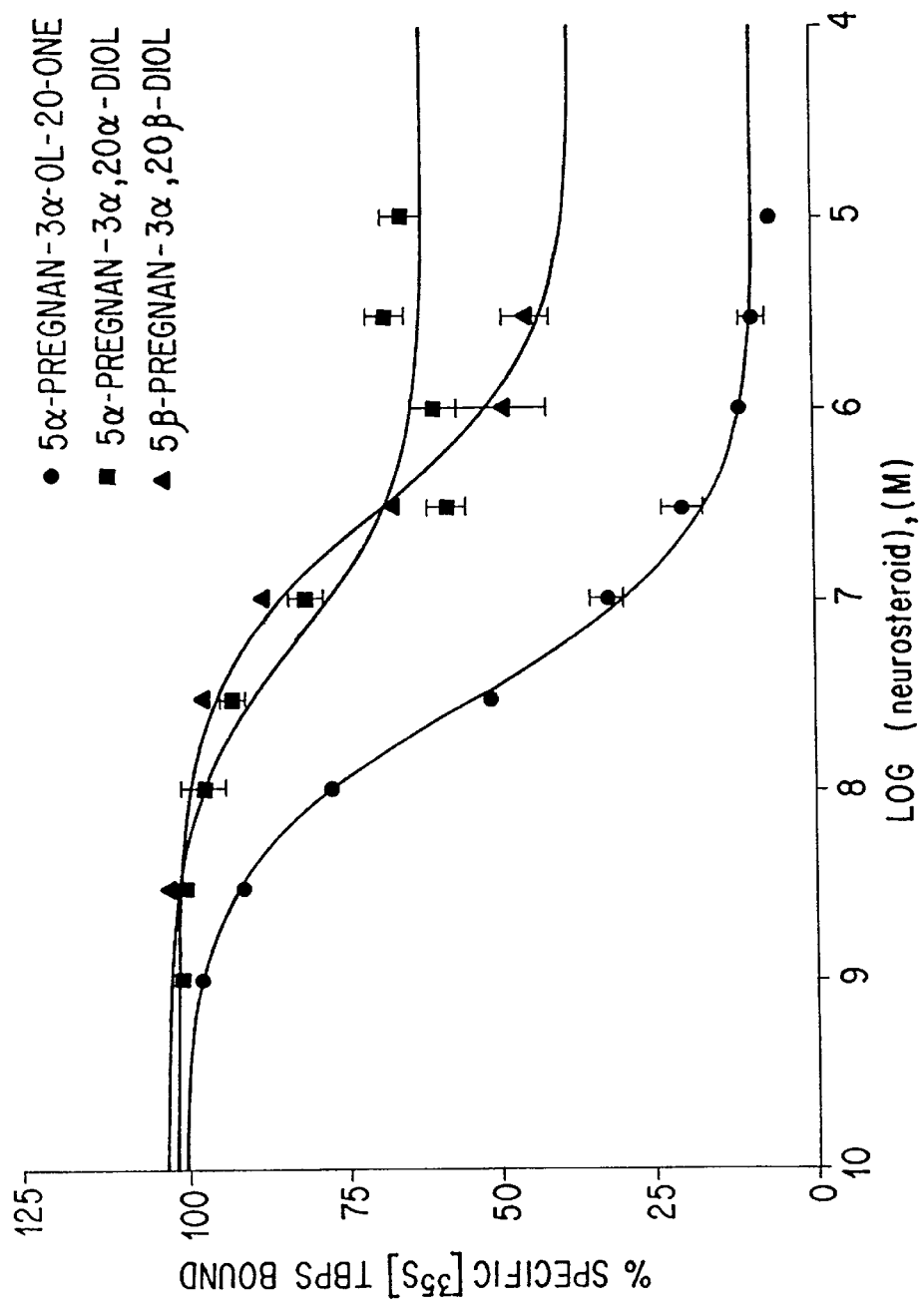
FIG. 6 is a plot of the effect of 3α-OH-5α-pregnan-20-one, 5α-pregnan-3α,20α-diol and 5β-pregnan-3α,20β-diol on inhibiting [$^{35}$S] TBPS binding in rat cortex homogenate.

To show the agonists with limited efficacy, the ability of 5α-pregnan-3α,20α-diol and 5β-pregnan-3α,20α-diol to partially modulate the [$^{35}$S]TBPS binding even at very high concentrations is illustrated (FIG. 6).

Figure 7:
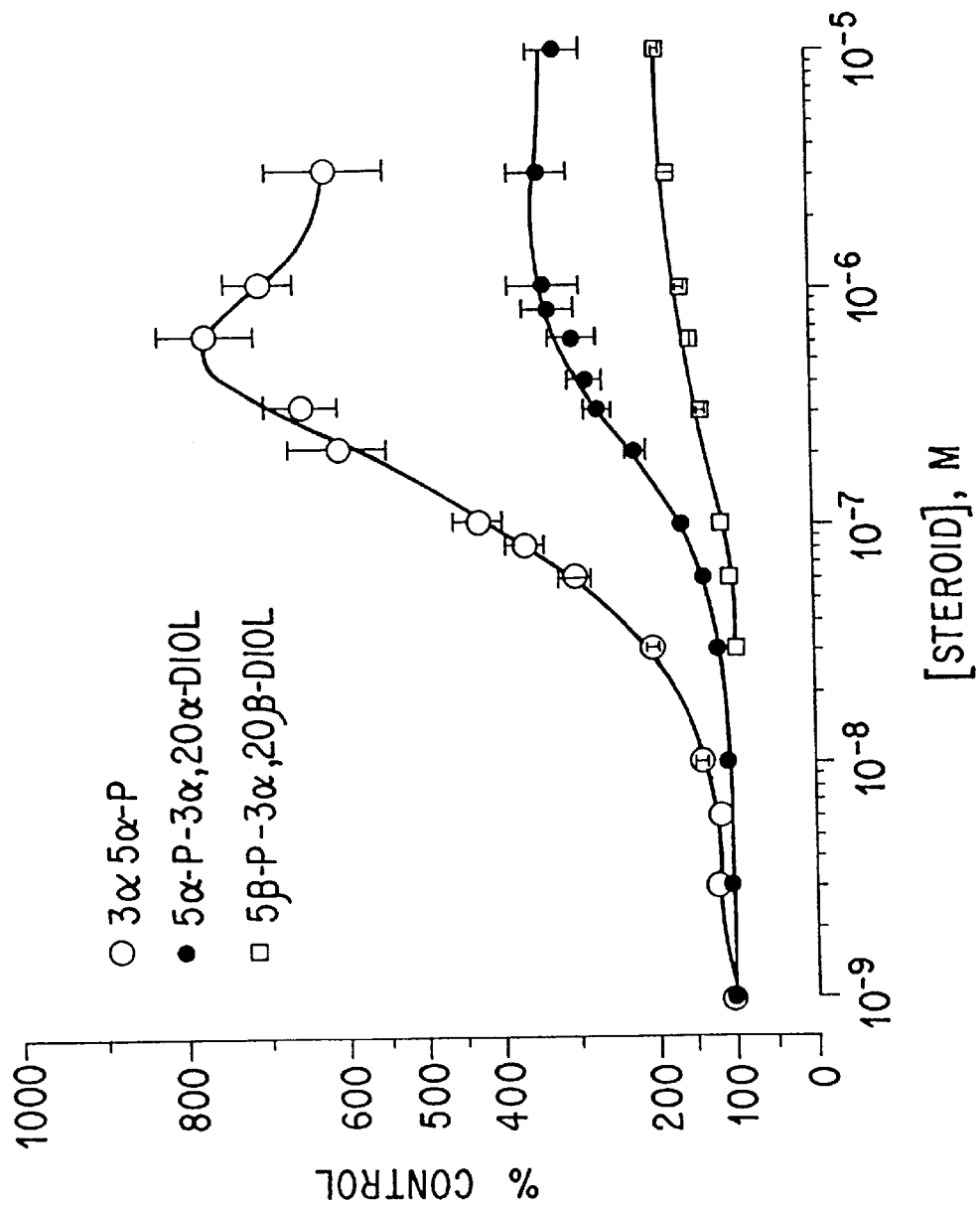
FIG. 7 is a plot showing the effect of 3α-OH-5α-pregnan-20-one, 5α-pregnan-3α,20α-diol, and 5β-pregnan-3α,20β-diol on the GABA-evoked current in Xenopus oocytes injected with human recombinant GABA receptor subunit α1β1γ2L.

In addition, the partial ability of these compounds to potentiate GABA-mediated enhancement of Cl$^-$ current were compared to that of 3α-hydroxy-5α-pregnan-20-one (FIG. 7) in Xenopus oocyte injected with human GABA$_A$ receptor genes is also shown.

When Xenopus oocyte expression system was used to test the limit efficacy property of some neuroactive steroids, the following procedure was performed. Xenopus laevis oocytes (stage VI) which had been "defolliculated" using the collagenase digestion method (3 hrs @18–23° C., 2 mg ml$^{-1}$ collagenase 'A' in Barth's saline with Ca$^{2+}$ salts omitted) were injected with cRNA transcripts of human GABA$_A$ receptor subunit complex α1 β1 and γ1. The major GABA$_A$ receptor complex is comprised of αβγ subunits. Injected oocytes were individually maintained in 96-well plates (200 μL per well of normal Barth's solution supplemented with penicillin 50 IU ml$^{-1}$, streptomycin 50 mg ml$^{-1}$ and gentomycin 100 mg ml$^{-1}$) for up to 9 days at 19–20° C. Agonist-induced currents were recorded from Xenopus oocytes voltage clamped at a holding potential of −60 mV, using an Axoclamp 2 A (Axon Instruments) voltage clamp amplifier in the twin electrode voltage clamp mode. The voltage-sensing and current-passing microelectrodes were filled with 3M KCl, and resistances of 1–3M Ohams when measured in the standard extracellular saline. The oocytes were continuously superfused with frog Ringer (120 mM NaCl; 2 mM KCl; 1.0 mM CaCl$_2$; 5 mM HEPES pH 7.4) at the rate of 5–7 ml min$^{-1}$ at rt (17–21° C.).

All drugs were applied via the perfusion system. Steroids (10$^{-2}$M) were prepared as concentrated stock solutions either in DMSO or ethanol and then diluted in the Ringer solution at the appropriated concentration. The final DMSO and ethanol concentration was 0.2% v/v, a concentration which had no effect upon GABA evoked responses. Stock solutions of all other drugs were made in Ringer solution. Membrane current responses were low-pass filtered at 100 Hz and recorded onto magnetic tape using an FM tape recorder (Racal Store 4DS) for subsequent analysis.

Compounds of and used in the present invention exhibit partial efficacy analogous to those described above also shown in the above tables.

Benefits Over Progesterone

The correlations between reduced levels of progesterone and the symptoms associated with PMS, PND, and catamenial epilepsy (Backstrom, et al., 1983; Dalton, K., 1984) led to the use of progesterone in their treatment (Mattson, et al., 1984; and Dalton, 1984). However, progesterone is not consistently effective in the treatment of the aforementioned syndromes. For example, no dose-response relationship exists for progesterone in the treatment of PMS (Maddocks, et al., 1987). These results are predictable when considered in light of the results of our in vitro studies which demonstrate that progesterone has very low potency at the GR complex, as seen in Table 1, compared to certain metabolites of progesterone.

The beneficial effect of progesterone is probably related to the variable conversion of progesterone to the active progesterone metabolites. The use of specific progesterone metabolites in the treatment of the aforementioned syndromes is clearly superior to the use of progesterone based upon the high potency and efficacy of the metabolites and their derivatives (See Gee, et al., 1987, and Table 1).

No Hormonal Side Effects

It has also been demonstrated that neuroactive steroids lack hormonal side effects by the lack of affinity for the progesterone and other hormonal steroid receptors (Tables 2–5). The data presented were obtained by performing assays in accordance with the procedures described in Gee, et al., 1988 previously to determine the effect of progesterone metabolites and their derivatives and the progestin R5020 on the binding of [$^3$H]R5020 to the progesterone receptor in rat uterus (Gee et al., 1988).

$^3$H-progesterone (0.15 nM) was incubated with the rat uterus cytosol in the presence of the test compounds. The specific bindings were determined after incubation and compared to the control incubation without the compounds. The data are expressed as percent inhibition of binding. If the compounds bind to the progesterone receptor with high affinity, a 100% inhibition of binding would be expected at the concentration tested.

Various hormonal activities of representative neuroactive steroids were further studied through testing their potential estrogenic, mineralocorticoid and glucocorticoid activities. These activities were analyzed by monitoring the ability of the compounds to inhibit binding of the steroid hormones to their respective hormone receptors. The results are shown in Tables 3–5. They are expressed as percent inhibition of $^3$H-ligand binding to the various steroid hormone receptors for the compounds at 10$^{-6}$M. Control values are represented by the binding in the absence of testing compounds.

In Table 3, rats were adrenalectomized 3 days prior to sacrifice. To isolate the mineralocorticoid receptor, brain cytosol fractions were prepared as describe in Gee, et al., 1988. The drugs were incubated with 3 nM of $^3$H-aldosterone (the specific ligand for the mineralocorticoid receptor) in the presence of the selective type II agonist RU28362 (0.5 μM) which blocks $^3$H-aldosterone binding to the type II (glucocorticoid) receptors.

TABLE 2

Inhibition of $^3$H-Progesterone Binding to the Boving Uteral Progesterone Receptors

| Competitor (10$^{-6}$ M) | % of Inhibition |
|---|---|
| R5020 | 100 |
| 5α-pregnan-3α-ol-20-one | 14 |
| 5α-pregnan-3α,21-diol-20-one | 13 |
| 5α-pregnan-3α,20-diol | 6 |
| 5α-pregnan-3α-ol-3α,-methyl-20-one | 4 |
| 5β-pregnan-3α,21-diole-20-one | 6 |
| 5α-pregnan-3β,20-trimethyl-3α,20-diol | 8 |
| 5β-pregnan-3α,20α-diol | 0 |
| 5β-pregnan-3α-ol-20-one | 9 |
| 5α-pregnan-20-dimethyl-3α,20-diol | 0 |

TABLE 3

Inhibition of $^3$H-Aldosterone Binding to Hippocampal Mineralocorticoid Receptors

| Competitor (10$^{-6}$ M) | % of Inhibition |
|---|---|
| Aldosterone | 95.5 |
| 5α-pregnan-3α,21-diol-20-one | 76.7 |
| 5β-pregnan-3α,21-diol-20-one | 13.8 |
| 5α-pregnan-3α,ol-20-one | 0 |
| 5β-pregnan-3α,ol-20-one | 0 |
| 5α-pregnan-3α,20α-diol | 0 |

TABLE 3-continued

Inhibition of $^3$H-Aldosterone Binding
to Hippocampal Mineralocorticoid Receptors

| Competitor ($10^{-6}$ M) | % of Inhibition |
|---|---|
| 5β-pregnan-3α,20α-diol | 0 |
| 5α-pregnan-3α,20-diol-20-dimethyl | 0 |
| 5α-pregnan-3α,ol-3β-methyl-20-one | 3.2 |
| 5α-pregnan-3β,20-trimethyl-3α,20-diol | 0 |

For Table 4, brain cytosol fractions were prepared as for Table 3, and the compounds were incubated with 3 nM of $^3$H-dexamethasone (the specific ligand for the glucocorticoid receptor).

TABLE 4

Inhibition of $^3$H-Dexamethasone Binding to
Glucocorticoid Receptors

| Competitor ($10^{-6}$ M) | % of Inhibition |
|---|---|
| Dexamethasone | 100 |
| 5α-pregnan-3α,21-diol-20-one | 29.5 |
| 5β-pregnan-3α,21-diol-20-one | 8.2 |
| 5α-pregnan-3α-ol-20-one | 8.7 |
| 5β-pregnan-3α-ol-20-one | 5.9 |
| 5α-pregnan-3α,20α-diol | 2.6 |
| 5β-pregnan-3α,20α-diol | 1.4 |
| 5α-pregnan-20-dimethyl-3α,20-diol | 2.6 |
| 5α-pregnan-3α-ol-3β-methyl-20-one | 0.6 |

Table 5 shows the inhibition of $^3$H-estradiol (the specific ligand for the estrogen receptor) binding to bovine uteri cytosol, prepared as previously described (Gee, et al., 1988). $^3$H-Estradiol (0.15 nM) was incubated with the cytosol in the presence of the compounds.

TABLE 5

Inhibition of $^3$H-Estradiol Binding to Bovine
Uteral Estrogen Receptors

| Competitor ($10^{-6}$ M) | % of Inhibition |
|---|---|
| 17β-estradiol | 100 |
| 5α-pregnan-3α-ol-20-one | 0 |
| 5α-pregnan-3α,21-diol-20-one | 2 |
| 5α-pregnan-3α,20α-diol | 0 |
| 5α-pregnan-3α-ol-3-methyl-20-one | 0 |
| 5β-pregnan-3α,21-diol-20-one | 0 |
| 5α-pregnan-3β,20-trimethyl-3α,20-diol | 0 |
| 5β-pregnan-3α,20α-diol | 8 |
| 5β-pregnan-3α-ol-20-one | 0 |
| 5α-pregnan-20-dimethyl-3α,20-diol | 0 |

The results of these experiments clearly show that neuroactive steroids do not have a strong affinity for any of the above steroid receptors. Thus, they will not have predicted hormonal side-effects which would result from such steroid receptor binding.

Anti-Convulsant Activity

Experiments were also performed to determine the physiological relevance of neuroactive steroid and GABA receptor interactions by assessing the ability of the compounds of and used in the invention to prevent metrazol induced convulsions in mice. Mice were injected with various doses of the test compounds of the invention, 10 minutes prior to the injection of metrazol. The time to onset of myoclonus (presence of forelimb clonic activity) induced by metrazol was determined by observing each mouse for a period of 30 minutes. In control mice, metrazol (85 mg/kg) will induce convulsion in 95% of the animals. The ability of several compounds of and used in the invention to protect mice from convulsion is shown in Table 6.

TABLE 6

Antimetrazol Activity of Neuroactive Steroids in Mice

| Name | Route | Vehicle | Dose (mg/kg) | % Protected |
|---|---|---|---|---|
| 3β-(4'-Acetylphenyl)ethynyl-3α-hydroxy-5α-pregnan-20-one | IP | 50% hpbcd | 10 | 75 |
| 3β-(4'-Acetylphenyl)ethynyl-3α-hydroxy-19-nor-5β-pregnan-20-one | IP | 50% hpbcd | 10 | 100 |
| 3β-(4'-Carboxyphenyl)ethynyl-3α-hydroxy-5β-pregnan-20-one ethyl ester | IP | 50% hpbcd | 10 | 18.75 |
| 3β-(4'-Hydroxybutyn-1'-yl)-3α-hydroxy-5β-pregnan-20-one | IP | 50% hpbcd | 10 | 100 |
| 3β-(4'-Acetylphenyl)ethynyl-3α-hydroxy-5β-pregnan-20-one | IP | 50% hpbcd | 10 | 75 |
| 3β-(4'-Acetoxybutyn-1'-yl)-3α-hydroxy-5β-pregnan-20-one | IP | 50% hpbcd | 10 | 100 |
| 3α-Hydroxy-3β-(3'-methoxy-1'-propynyl)-5β-pregnan-20-one | IP | 50% hpbcd | 10 | 75 |
| 3β-(4'-Acetylphenylethynyl)-3α,21-dihydroxy-5α-pregnan-20-one | IP | 50% hpbcd | 1 | 87.5 |
| 3β-(4'-Acetylphenylethynyl)-3α,21-dihydroxy-5β-pregnan-20-one | IP | 50% hpbcd | 10 | 75 |
| 3β-(4'-Acetylphenylethynyl)-3α,21-dihydroxy-5α-pregnan-20-one 21-hemsuccinate salt | PO | water | 10 | 80 |
| 3β-(4'-Acetylphenylethynyl)-3α,12-dihydroxy-5β-pregnan-20-one 21-hemsuccinate salt | PO | water | 10 | 75 |
| 3β-(4'-hydroxy-1'-butynyl)-3α-hydroxy-5β-pregnan-11,20-dione | IP | 50% hpbcd | 10 | 50 |
| 3β-[3-(2-propynyloxy)propyn-1-yl]-3α-hydroxy-5β-pregnan-20-one | IP | 50% hpbcd | 10 | 50 |
| 3β-(4'-Hydroxybutyn-1'-yl)-3α-hydroxy-5α-pregnan-20-one | IP | 50% hpbcd | 10 | 50 |

TABLE 6-continued

Antimetrazol Activity of Neuroactive Steroids in Mice

| Name | Route | Vehicle | Dose (mg/kg) | % Protected |
|---|---|---|---|---|
| 3α-Hydroxy-3β-(5'-oxo-1-hexynyl)-5β-pregnan-20-one cyclic 5'-(1,2-ethanediyl acetal) | IP | 50% hpbcd | 10 | 50 |
| 3β-(4'-Biphenyl)ethynyl-3α-hydroxy-5β-pregnan-20-one | IP | dmso | 10 | 0 |
| 3β-(5-Acetylthien-2-yl)ethynyl-3α-Hydroxy-5β-pregnan-20-one | IP | 50% hpbcd | 10 | 25 |
| 3β-(4'-Trifuoromethylphenyl)ethynyl-3α-hydroxy-5β-pregnan-20-one | IP | dmso | 10 | 25 |
| 3β-(4'-Chlorophenyl)ethynyl-3α-hydroxy-5β-pregnan-20-one | IP | dmso | 10 | 37.5 |
| 3β-(5'-Hydroxypentyn-1'-yl)-3α-hydroxy-5β-pregnan-20-one | IP | 50% hpbcd | 10 | 12.5 |
| 3α-Hydroxy-3β-(thien-2-yl)ethynyl-5β-pregnan-20-one | IP | 50% hpbcd | 10 | 37.5 |
| 3β-(3'-Acetylphenyl)ethynyl-3α-hydroxy-5β-pregnan-20-one | IP | 50% hpbcd | 10 | 75 |
| 3α-Hydroxy-3β-[4'(R/S)-hydroxypentynyl]-5β-pregnan-20-one | IP | 50% hpbcd | 10 | 87.5 |
| 3β-(4'-Cyanophenyl)ethynyl-3α-hydroxy-5β-pregnan-20-one | IP | 50% hpbcd | 10 | 43.7 |
| 3β-(4'-Hydroxybutyn-1'-yl)-3α-hydroxy-5β-pregnan-20-one 4'-hemisuccinate sodium salt | IP | water | 10 | 87.5 |
| 3α-Hydroxy-3β-[3'-(1H-pyrazol-1-yl)-1'-propynyl]-5β-pregnan-20-one | IP | 50% hpbcd | 10 | 25 |
| 3α-Hydroxy-3β-(4'-methylphenyl)ethynyl-5β-pregnan-20-one | IP | 50% hpbcd | 10 | 75 |
| 3α-Hydroxy-3β-(6-oxo-1-heptynyl)-5β-pregnan-20-one | IP | 50% hpbcd | 10 | 62.5 |
| 3β-(5'-Acetoxypentyn-1'-yl)-3α-hydroxy-5β-pregnan-20-one | IP | 50% hpbcd | 10 | 12.5 |
| 3α-Hydroxy-3β-(2'-pyridylethynyl)-5β-pregnan-20-one | IP | 50% hpbcd | 10 | 37.5 |
| 3α-Hydroxy-3β-(5'-oxo-1-hexynyl)-5β-pregnan-20-one | IP | 50% hpbcd | 10 | 25 |
| 3β-(4'-Cyano-1'-butynyl)-3α-hydroxy-5β-pregnan-20-one | IP | 50% hpbcd | 10 | 12.5 |
| 3α-Hydroxy-3β-(3'-hydroxypropynyl)-5β-pregnan-20-one | IP | 50% hpbcd | 10 | 25 |
| 3α-Hydroxy-3β-[3'(RS)-hydroxybutynyl]-5α-pregnan-20-one | IP | 50% hpbcd | 10 | 50 |
| 3α-Hydroxy-3β-[4'(R/S)-hydroxypentynyl]-5β-pregnan-20-one 4'(R/S)-hemisuccinate sodium salt | IP | water | 10 | 50 |
| 3β-(5'-Cyanopentynyl)-3α-hydroxy-5β-pregnan-20-one | IP | 50% hpbcd | 10 | 25 |
| 3α-Hydroxy-3β-[4'(R/S)-hydroxypentynyl]-5α-pregnan-20-one | IP | 50% hpbcd | 10 | 25 |
| 3α-Hydroxy-3β-[3'(RS)-hydroxybutynyl]-5β-pregnan-20-one | IP | 50% hpbcd | 10 | 25 |
| 3β-(5'-Hydroxypentyn-1'-yl)-3α-hydroxy-5β-pregnan-20-one 5'-hemisuccinate sodium salt | IP | 50% hpbcd | 10 | 37.5 |
| 3β-(3'-Acetoxypropyn-1'-yl)-3α-hydroxy-5β-pregnan-20-one | IP | 50% hpbcd | 10 | 12.5 |
| 3α-Hydroxy-3β-(2'-methoxyphenyl)ethynyl-5β-pregnan-20-one | IP | dmso | 10 | 12.5 |
| 3β-(6'-Acetoxyhexyn-1'-yl)-3α-hydroxy-5β-pregnan-20-one | IP | 50% hpbcd | 10 | 37.5 |
| 3α-Hydroxy-3β-[3'-(pyrid-4-yloxy)-1'-propynyl]-5β-pregnan-20-one | IP | 50% hpbcd | 10 | 12.5 |
| 3β-[2-(3',4'-Dimethoxyphenyl)ethyl]-3α-hydroxy-5β-pregnan-20-one | IP | 50% hpbcd | 10 | 12.5 |
| 3β-(3'-Hydroxy-3'-methylbutyn-1'-yl)-3α-hydroxy-5β-pregnan-20-one | IP | 50% hpbcd | 10 | 43.7 |
| 3α-Hydroxy-3β-[3'-(1H-1,2,3-triazol-1-yl)-1'-propynyl]-5β-pregnan-20-one | IP | 50% hpbcd | 10 | 25 |
| 3α-Hydroxy-3β-[3'-(1H-1,2,4-triazol-1-yl)-1'-propynyl]-5β-pregnan-20-one | IP | 50% hpbcd | 10 | 10 |
| Sodium S-(3α-hydroxy-5β-pregnan-20-on-21-yl) thiosulfate | IP | water | 10 | 37.5 |
| Sodium S-(3α-hydroxy-3β-methyl-5α-pregnan-20-on-21-yl) thiosulfate | IP | water | 10 | 62.5 |
| Sodium S-[3α-hydroxy-3β-(4'-hydroxybutynyl)-5β-pregnan-20-on-21-yl] thiosulfate | PO | water | 40 | 33.3 |
| Sodium S-(3α-hydroxy-3β-methoxymethyl-5α-pregnan-20-on-21-yl) thiosulfate | IP | water | 10 | 62.5 |

TABLE 6-continued

Antimetrazol Activity of Neuroactive Steroids in Mice

| Name | Route | Vehicle | Dose (mg/kg) | % Protected |
|---|---|---|---|---|
| Sodium S-(3α-hydroxy-3β-trifluoromethyl-19-nor 5β-pregnan-20-on-21-yl)thiosulfate | IP | water | 40 | 37.5 |
| 3α-Hydroxy-21-(1'-imidazolyl)-5β-pregnan-20-one hemisuccinate sodium salt | IP | 50% hpbcd | 10 | 50 |
| 3α-hydroxy-21-(2'H-1,2,3,4-tetrazol-2'-yl)-5β-pregnan-20-one | IP | 50% hpbcd | 10 | 37.5 |
| 3α-Hydroxy-21-(2H-1,2,3-triazol-2-yl)-5β-pregnan-20-one | IP | 50% hpbcd | 10 | 100 |
| 3α-Hydroxy-21-[1H-(4-methyl-5-carboxyl)imidazol-1-yl)-5β-pregnan-20-one ethyl ester | IP | 50% hpbcd | 10 | 37.5 |
| 21-[1'-(4,5-Dichloro)imidazolyl]-3α-hydroxy-5β-pregnan-20-one | IP | 50% hpbcd | 10 | 37.5 |
| 3α-Hydroxy-21-(1'-imidazolyl)-5α-pregnan-20-one | IP | 50% hpbcd | 10 | 50 |
| 3α-Hydroxy-21-(1'-imidazolyl)-5β-pregnan-20-one | IP | 50% hpbcd | 10 | 12.5 |
| 3β-Ethynyl-3α-Hydroxy-21-(1'-imidazolyl)-5β-pregnan-20-one | IP | 50% hpbcd | 10 | 50 |
| 3α-Hydroxy-21-(1H-3,5-dimethylpyrazolyl)-5β-pregnan-20-one | IP | 50% hpbcd | 10 | 50 |
| 3α-Hydroxy-21-(1'-imidazolyl)-3β-methyl-5α-pregnan-20-one | IP | 50% hpbcd | 10 | 75 |
| 3β-Ethynyl-3α-Hydroxy-21-(1'-pyrazolyl)-5β-pregnan-20-one | IP | 50% hpbcd | 10 | 62.5 |
| 3α-Hydroxy-21-(1'-pyrazolyl)-3β-methyl-5α-pregnan-20-one | IP | 50% hpbcd | 10 | 87.5 |
| 3α-Hydroxy-21-(pyrazol-1-yl)-5β-pregnan-20-one | IP | 50% hpbcd | 10 | 62.5 |
| 3α-Hydroxy-3β-methyl-21-(1',2',4'-triazolyl)-5α-pregnan-20-one | IP | 50% hpbcd | 10 | 87.5 |
| 3α-Hydroxy-21-(1',2',4'-triazol-1-yl)-5β-pregnan-20-one | IP | 50% hpbcd | 10 | 37.5 |
| 21-[1'-(4,5-Dicyano)imidazolyl]-3α-hydroxy-5β-pregnan-20-one | IP | 50% hpbcd | 10 | 50 |
| 3α-Hydroxy-21-[1H-(2-methyl)imidazol-1-yl)-5β-pregnan-20-one | IP | 50% hpbcd | 10 | 6.2 |
| 3α-Hydroxy-21-(1'-pyrazolyl)-3β-trifluoromethyl-5β-19-nor-pregnan-20-one | IP | 50% hpbcd | 10 | 12.5 |
| 3α-Hydroxy-21-(1'-imidazolyl)-3β-trifluoromethyl-5β-19-nor-pregnan-20-one | IP | 50% hpbcd | 10 | 50 |

The ability of neuroactive steroids to protect animals against other chemical convulsants was further demonstrated for 3α-hydroxy-5α-pregnan-20-one, 3α,21-dihydroxy-5α-pregnan-20-one and 3α-hydroxy-3β-methyl-5α-pregnan-20one. The anticonvulsant tests are similar to that described above. The following chemical convulsants are: metrazole (85 mg/kg); (+)bicuculline (2.7 mg/kg); picrotoxin (3.15 mg/kg); strychnine (1.25 mg/kg); or vehicle (0.9% saline). Immediately after the injection of convulsant or vehicle, the mice were observed for a period of 30 to 45 minutes. The number of animals with tonic and/or clonic convulsions was recorded. In the maximal electroshock test, 50 mA of current at 60 Hz was delivered through corneal electrodes for 200 msec to induce tonic seizure. The ability of compounds to abolish the tonic component was defined as the endpoint. General CNS depression potential was determined by a rotorod test 10 minutes after the injection of compounds where the number of mice staying on a rotating (6 rpm) rod for 1 minute in one of the three trials was determined. The $ED_{50}$ (the dose at which the half-maximal effect occurs) was determined for each screen and are presented in Table 7, infra. The results demonstrate that neuroactive steroids, in comparison to other clinically useful anti-convulsants, are highly effective with profiles similar to that of the BZ clonazepam. These observations demonstrate the therapeutic utility of these compounds as modulators of brain excitability, which is in correspondence with their high affinity interaction with the GR complex in vitro.

TABLE 7

Anticonvulsant Activity of Exemplified Neuroactive Steroids and those of Selected Clinically Useful Anticonvulsants in Mice $ED_{50}$ (mg/Kg)

| Compound | RR | MES | MTZ | BIC | PICRO | STR |
|---|---|---|---|---|---|---|
| 3α5α[a]-P | 30 | 28.6 | 4.9 | 12.3 | 10.2 | >300 |
| 5α-THDOC[a] | 22.9 | 26.7 | 8.1 | 17.8 | 5.6 | >300 |
| 3α-hydroxy-3β-methyl-5α-pregnan-20 one[b] | 246.2 | >100 | 6.3 | 61.9 | 35.4 | >100 |
| Clonazepam* | 0.184 | 93 | 0.009 | 0.0086 | 0.043 | NP |
| Phenobarbital* | 69 | 22 | 13 | 38 | 28 | 95 |
| Phenytoin* | 65 | 10 | NP | NP | NP | ** |

TABLE 7-continued

Anticonvulsant Activity of Exemplified
Neuroactive Steroids and those of Selected Clinically Useful
Anticonvulsants in Mice
$ED_{50}$ (mg/Kg)

| Compound | RR | MES | MTZ | BIC | PICRO | STR |
|---|---|---|---|---|---|---|
| Progabide*** | — | 75 | 30 | 30 | 105 | 75 |
| Valproate* | 426 | 272 | 149 | 360 | 387 | 293 |

The abbreviations are RR (Rotorrod); MES (maximal electroschock); MTZ (metrazol); BIC (bicuculline); PICRO (picrotoxin); STR (styrchnine); NP (no protection)
(a)Dissolved in 20% hydroxypropyl-β-cyclodextrin in water. The route of administration for steroids and convulsants was i.p. and s.c., respectively.
*Anticonvulsant data are from Swinyard & Woodhead, General principles: experimental detection, quantification and evaluation of anticonvulsants, in Antiepileptic Drugs, D. M. Woodbury, J. K. Penry, and C. E. Pippenger, eds. p. 111, (Raven Press, New York), 1982.
(b)Vehicle contained 0.32% hydroxypropylmethyl cellulose and 4% tween 80 in saline.
**Maximum protection of 50% at 55–100 mg/kg.
***The chemical convulsants in the progabide studies were administered i.v., all data from Worms et al., Gamma-aminobutyric acid (GABA) receptor stimulation. I. Neuropharmacological profiles of progabide (SL 76002) and SL 75102, with emphasis on their anticonvulsant spectra, Journal of Pharmacology and Experimental Therapeutics 220: 660–671 (1982).

Anxiolytic Effects

The following experiments demonstrate that the progesterone metabolites, 3α-OH-5α-pregnan-20-one and 3α-OH-5β-pregnan-20-one are effective anxiolytics in four animal models of human anxiety that measure the behavioral effects of anxiolytic compounds. It is to be understood that these two compounds describe the invention by way of illustration. Data on their synthetic derivatives in these measurements also is presented in Table 8–10. The four animal models used to measure the behavioral effects of anxiolytic compounds are: 1) light/dark transition test; 2) elevated plus-maze; 3) Geller-Seifter conflict test and 4) Vogel test.

a) Light/dark Transition Test

The light/dark transition test (Crawley and Goodwin, "Preliminary report of a simple animal behavior model for th anxiolytic effect of benzodiazepines", Pharmacol. Biochem. Behav. 13:67–70 (1980)) is based on the observation that rodents naturally tend to explore novel environments, but open, brightly lit arenas are aversive to the rodents and inhibit exploratory behavior (Christmas and Maxwell, "A comparison of effects of some benzodiazepines and other drugs on aggressive and exploratory behavior in mice and rats", Neuropharmacol. 9:17–29 (1970); File, "The use of social interaction as a method of detecting anxiolytic activity of chlordiazepoxide-like drugs", J. Neurosci. Meth. 2:219–238 (1980)). A variety of clinically established anxiolytics including diazepam, clonazepam and pentobarbital have been shown to increase the number of transitions between the light box and the dark box, whereas non-anxiolytic drugs do not demonstrate this behavioral effect (Crawley et al., "Absence of intrinsic antagonist actions of benzodiazepine antagonists on an exploratory model of anxiety in the mice", Neuropharmacol. 23:531–537 (1984)).

Male N.I.J. Swiss-Webster mice (Harlan, Harlan, Indianapolis, Ind.) weighing 15–20 g were housed four per cage in polyethylene cages with sawdust bedding. The colony room was environmentally controlled (22° C.) with a 12 hr light/dark cycle (0600–1800 hr). Food and water were available ad libitum, except during testing. The experiments were run from 0700–1500 hr and groups were counterbalanced for time of day effects. Mice were only administered drug or vehicle once.

The method used was a modification of methods previously described (Wieland et al., "Anxiolytic activity of progesterone metabolite 5α-pregnan-3α-ol-20-one", Br. Res. 565:263–268 (1991)). The apparatus included two 2-compartment automated test chambers (Model RXYZCM16, Omnitech Electronics, Columbus, Ohio). The open compartment was connected to the enclosed compartment via a 7.5×7.5 cm passageway. The open compartment was brightly lit using a 200 W incandescent light bulb. The experimental room was kept dark. Interruptions of the infrared beams in either chamber were automatically recorded by being linked to a computer through a Digiscan Analyzer (Omnitech Electronics) and the data was analyzed using the Integrated Lab Animal Monitoring System (Omnitech Electronics). N.I.H. Swiss-Webster mice were administered vehicle or test drug intraperitoneally (IP), 10 min later they were placed in the center of the lit compartment. The number of transitions between the lit and dark chambers, total activity in the lit chamber and the time spent in the lit chamber were measured during a 10 min test period.

Figure 8:
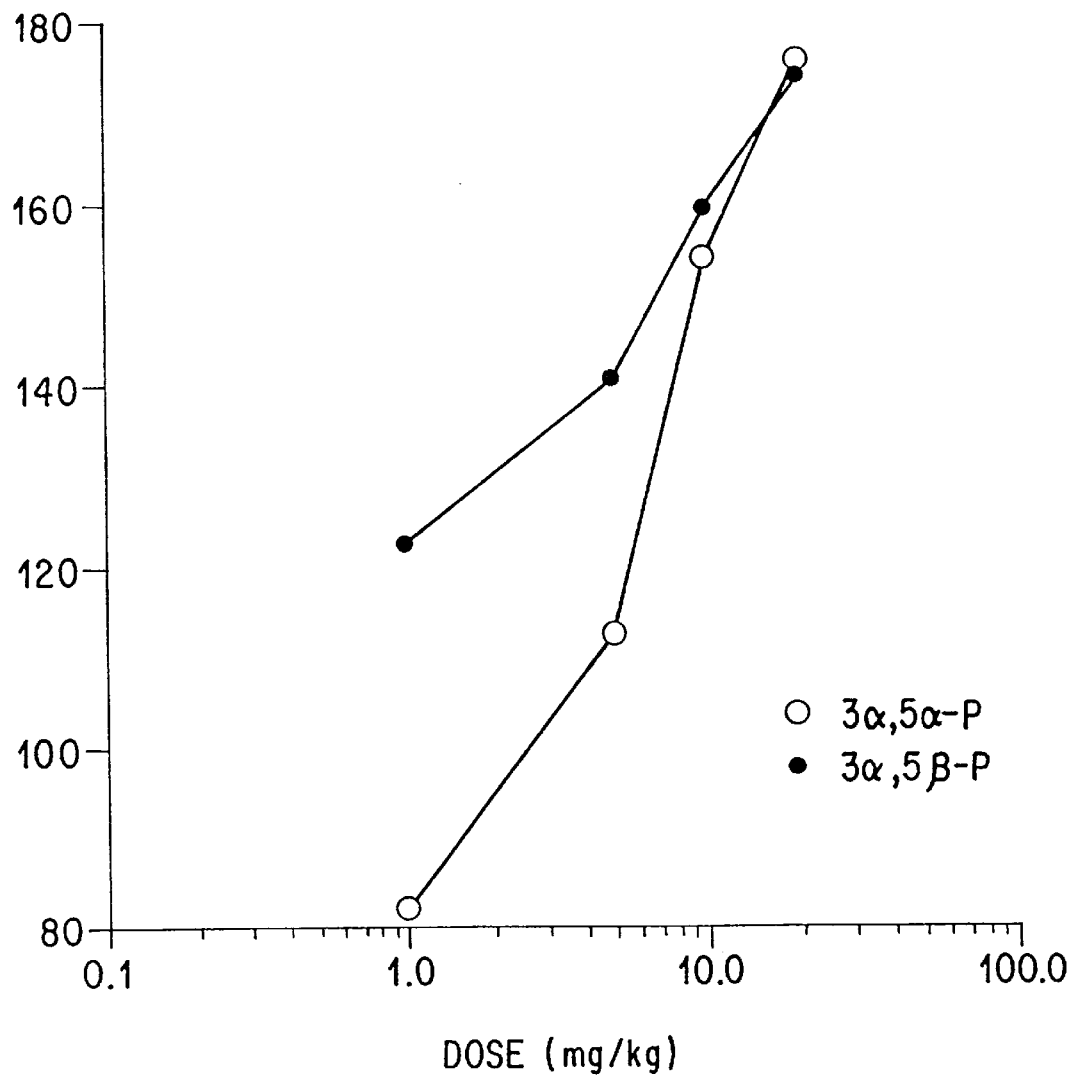
FIG. 8 is a line graph of the number of transitions from light to dark occurring within ten minutes of injection of 3α-OH-5α-pregnan-20-one and 3α-OH-5β-pregnan-20-one.

FIG. 8 shows the effects of 3α-OH-5α-pregnan-20-one and 3α-OH-5β-pregnan-20-one in the light-dark transition test. Both compounds produced a significant dose-response curve in relation to the number of transitions between the dark box and the light box. Post-hoc comparisons showed that the number of the crossing for doses for both 3α-OH-5α-pregnan-20-one and 3α-OH-5β-pregnan-20-one were significantly increased at doses tested from control (Dunnett's t-test).

In addition both 3α-OH-5α-pregnan-20-one and 3α-OH-5β-pregnan-20-one produced significant ($p<0.01$) increases in activity at 10 & 20 mg/kg as compared to control groups (Dunnett's t-test). There were no significant differences between the two compounds at any dose tested.

b) Elevated Plus-Maze

The theoretical basis for the elevated plus-maze test is similar to that of the light/dark transition test. As it was described previously (Pellow et al. "Validation of open-:closed arm entries in an elevated plus-maze as a measure of anxiety in the rat", J. Neurosci. Meth. 14:149–167 (1985)), the elevated plus-maze apparatus is designed to utilize the mice's natural aversion to open spaces. The apparatus consists of two open-arms and two enclosed-arms. The elevated plus-maze test allows for two measures of anxiety, the number of entries into the open-arms and the time spent on the open-arms, both expressed as a percentage of the total number of entries and time spent in/on both the open-arms and enclosed-arms.

Male N.I.H. Swiss-Webster mice (Harlan, Indianapolis, Ind.) weighing 15–20 g were housed four per cage in polyethylene cages with sawdust bedding. The colony room was environmentally controlled (22° C.) with a 12 hr light/dark cycle (0600–1800 hr). Food and water were available ad libitum, except during testing. The experiments were run from 0700–1500 hr and groups were counterbalanced for time of day effects. Mice were only administered drug or vehicle once.

The method used was previously described (Lister, "The use of Plus-Maze to measure anxiety in the mouse", Psychlopharmacol. 92:180–185 (1987)). The apparatus included two open arms perpendicular to two enclosed arms elevated 50 cm from the floor. Each arm was 50 cm long and the walls of the enclosed arms were 40 cm tall. The maze was made completely of black plexiglass. Incandescent 200 W light bulbs were above each of the open arms to produce a strong contrast between the open arms and the enclosed arms.

Figure 9A:
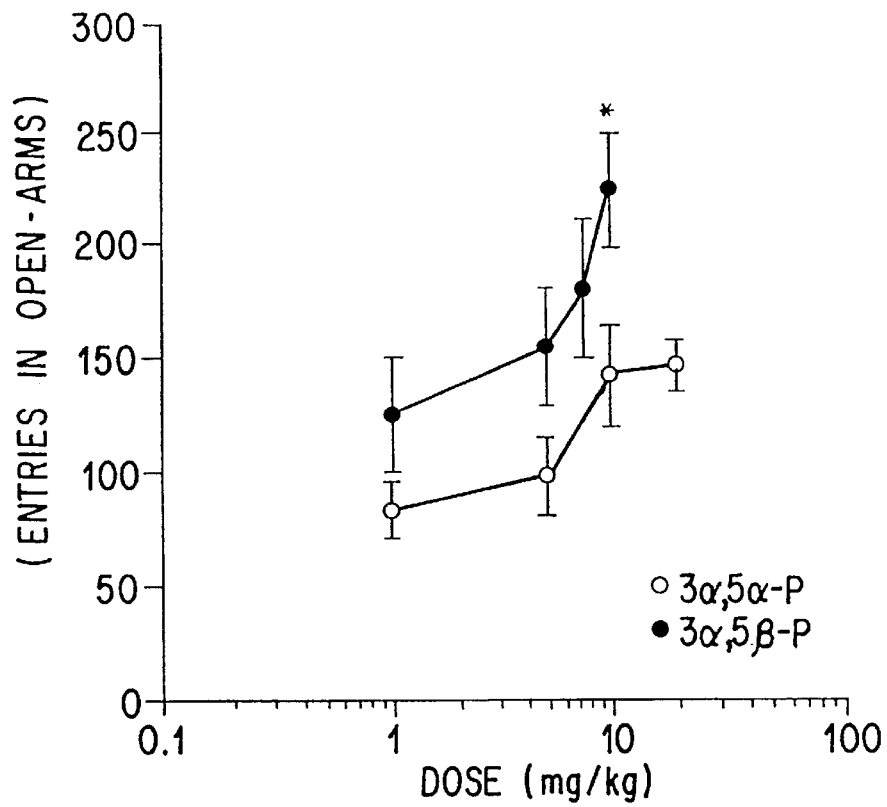
FIGS. 9A and 9B are two line graphs of the percentage of (A) entries into and (B) the time on the open-arms during a five-minute test period of 3α-OH-5α-pregnan-20-one and 3α-OH-5β-pregnan-20-one in the elevated plus-maze test.

Ten minutes after an injection, the N.I.H. Swiss-Webster mice were placed in the center of the plus-maze facing an open arm. During the 5 min test period, the number of entries onto the open arms and the enclosed arms, and the time spent in the open arms and enclosed arms were measured. All four paws had to be within an arm for the dependent variable to be measured. Therefore, the time spent in the center of the maze is not counted, so the total time spent in the open arms and the enclosed arms may not equal 5 min. The effects of 3α-OH-5α-pregnan-20-one and 3α-OH-5β-pregnan-20-one in the elevated plus-maze test are shown in FIG. 9A. Both compounds demonstrate increase proportion of entries into the open-arms across doses. 3α-OH-5α-pregnan-20-one produced significant increase in entries at 20 mg/kg (p≦0.05), whereas 3α-OH-5β-pregnan-20-one produced significant increases in entries at 5 mg/kg (p≦0.05), 7.5 mg/kg (p≦0.01), and 10 mg/kg (p≦0.01).

Figure 9B:
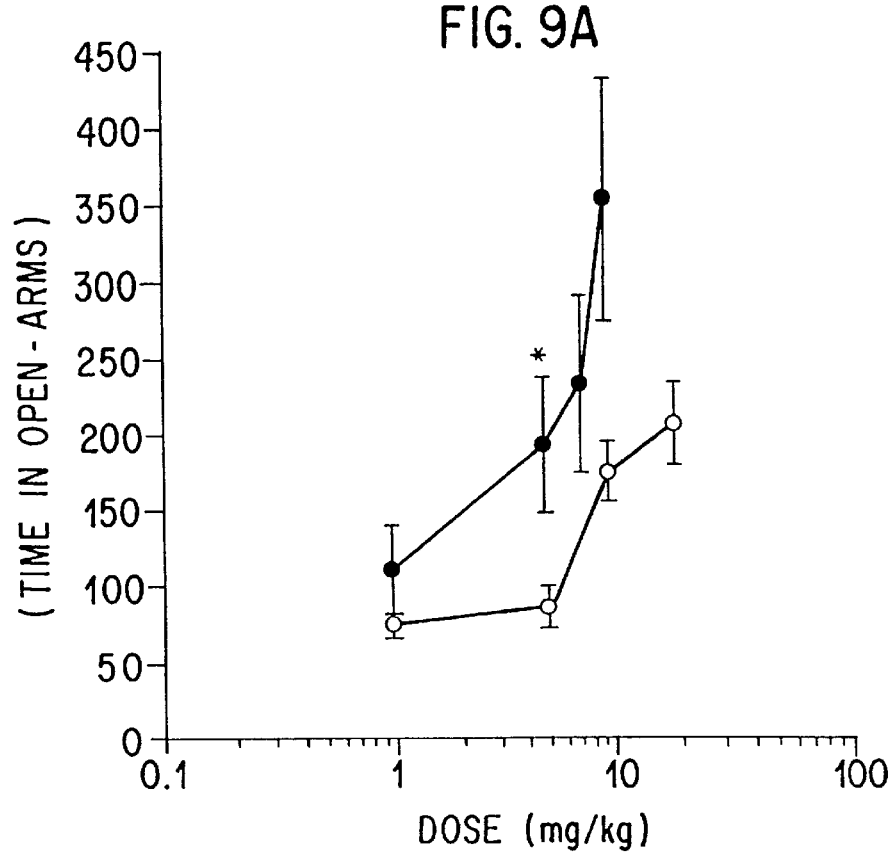

In addition, 3α-OH-5α-pregnan-20-one and 3α-OH-5β-pregnan-20-one produced dose-dependent increases in the time spent in the open-arms (FIG. 9B). 3α-OH-5α-pregnan-20-one produced significant increases in time spent on the open-arms at 10 mg/kg (p≦0.01), whereas 3α-OH-5β-pregnan-20-one produced significant increases in time spent on the open-arms at 7.5 mg/kg (p≦0.01) and 10 mg/kg (p≦0.01).

Table 8 shows the summary of anxiolytic activities of compounds of and used in the invention using the elevated plus-maze under the same conditions described above.

TABLE 8

Anxiolytic Activity in Plus Maze in Mice

| Name | Route | Dose mg/kg | Vehicle | % Control |
|---|---|---|---|---|
| 3β-(4'-Acetylphenyl)ethynyl-3α-hydroxy-5α-pregnan-20-one | IP | 10 | 50% hpbcd | 175.7 |
| 3β-(4'-Acetylphenyl)ethynyl-3α-hydroxy-19-nor-5β-pregnan-20-one | IP | 10 | 50% hpbcd | 191 |
| 3β-(4'-Hydroxybutyn-1'-yl)-3α-hydroxy-5β-pregnan-20-one | IP | 10 | 50% hpbcd | 141 |
| 3β-(4'-Acetoxybutyn-1'-yl)-3α-hydroxy-5β-pregnan-20-one | IP | 10 | 50% hpbcd | 159 |
| 3α-Hydroxy-3β-(3'-methoxy-1'-propynyl)-5β-pregnan-20-one | IP | 10 | 50% hpbcd | 134 |
| 3β-[3-(2-Propynyloxy)propyn-1-yl]-3α-hydroxy-5β-pregnan-20-one | IP | 10 | 50% hpbcd | 178 |
| 3β-(4'-Hydroxybutyn-1'-yl)-3α-hydroxy-5α-pregnan-20-one | IP | 10 | 50% hpbcd | 186 |
| 3β-(4'-Biphenyl)ethynyl-3α-hydroxy-5β-pregnan-20-one | IP | 10 | dmso | 111 |
| 3β-(5-Acetylthien-2-yl)ethynyl-3α-Hydroxy-5β-pregnan-20-one | IP | 10 | 50% hpbcd | 83 |
| 3β-(4'-Chlorophenyl)ethynyl-3α-hydroxy-5β-pregnan-20-one | IP | 10 | dmso | 161 |
| 3β-(5'-Hydroxypentyn-1'-yl)-3α-hydroxy-5β-pregnan-20-one | IP | 10 | 50% hpbcd | 137 |
| 3α-Hydroxy-3β-(thien-2-yl)ethynyl-5β-pregnan-20-one | IP | 10 | 50% hpbcd | 148 |
| 3β-(4'-Acetylphenylethynyl)-3α,21-dihydroxy-5α-pregnan-20-one | IP | 1 | 50% hpbcd | 150 |
| 3β-(4'-Acetylphenylethynyl)-3α,21-dihydroxy-5β-pregnan-20-one | IP | 10 | 50% hpbcd | 115 |
| 3β-(4'-Acetylphenylethynyl)-3α,21-dihydroxy-5α-pregnan-20-one 21-hemsuccinate salt | PO | 10 | water | 166 |
| 3β-(4'-Acetylphenylethynyl)-3α-21-dihydroxy-5β-pregnan-20-one 21-hemsuccinate salt | PO | 10 | water | 248 |
| 3β-(4'-hydroxy-1'-butynyl)-3α-hydroxy-5α-pregnan-11,20-dione | IP | 10 | 50% hpbcd | 119 |
| 3β-(3'-Acetylphenyl)ethynyl-3α-hydroxy-5β-pregnan-20-one | IP | 10 | 50% hpbcd | 143 |
| 3β-(4'-Cyanophenyl)ethynyl-3α-hydroxy-5β-pregnan-20-one | IP | 10 | 50% hpbcd | 169 |
| 3β-(4'-Hydroxybutyn-1'-yl)-3α-hydroxy-5β-pregnan-20-one 4'-hemisuccinate sodium salt | IP | 10 | water | 149 |
| 3α-Hydroxy-3β-[3'-(1H-pyrazol-1-yl)-1'-propynyl]-5β-pregnan-20-one | IP | 10 | 50% hpbcd | 116 |
| 3α-Hydroxy-3β-(4'-methylphenyl)ethynyl-5β-pregnan-20-one | IP | 10 | 50% hpbcd | 148 |
| 3α-Hydroxy-3β-(6-oxo-1-heptynyl)-5β-pregnan-20-one | IP | 10 | 50% hpbcd | 130.5 |
| 3α-Hydroxy-3β-(2'-pyridylethynyl)-5β-pregnan-20-one | IP | 10 | 50% hpbcd | 123 |
| 3β-(4'-Cyano-1'-butynyl)-3α-hydroxy-5β-pregnan-20-one | IP | 10 | 50% hpbcd | 184 |
| 3α-Hydroxy-3β-(3'-hydroxypropynyl)-5β-pregnan-20-one | IP | 10 | 50% hpbcd | 128 |
| 3α-Hydroxy-3β-[4'(R/S)-hydroxypentynyl]-5α-pregnan-20-one | IP | 10 | 50% hpbcd | 102 |
| 3α-Hydroxy-3β-[3'(RS)-hydroxybutynyl]-5β-pregnan- | IP | 10 | 50% | 137.7 |

TABLE 8-continued

Anxiolytic Activity in Plus Maze in Mice

| Name | Route | Dose mg/kg | Vehicle | % Control |
|---|---|---|---|---|
| 20-one | | | hpbcd | |
| 3β-(5'-Hydroxypentyn-1'-yl)-3α-hydroxy-5β-pregnan-20-one 5'-hemisuccinate sodium salt | IP | 10 | 50% hpbcd | 155 |
| 3β-(3'-Acetoxypropyn-1'-yl)-3α-hydroxy-5β-pregnan-20-one | IP | 10 | 50% hpbcd | 109 |
| 3α-Hydroxy-3β-(2'-methoxyphenyl)ethynyl-5β-pregnan-20-one | IP | 10 | dmso | 152 |
| 3β-(6'-Acetoxyhexyn-1'-yl)-3α-hydroxy-5β-pregnan-20-one | IP | 10 | 50% hpbcd | 206 |
| 3α-Hydroxy-3β-[3'-(1H-1,2,3-triazol-1-yl)-1'-propynyl]-5β-pregnan-20-one | IP | 10 | 50% hpbcd | 116 |
| 3α-Hydroxy-3β-[3'-(1H-1,2,4-triazol-1-yl)-1'-propynyl]-5β-pregnan-20-one | IP | 10 | 50% hpbcd | 122 |
| Sodium S-(3α-hydroxy-5β-pregnan-20-on-21-yl) thiosulfate | IP | 10 | 50% hpbcd | 143 |
| Sodium S-(3α-hydroxy-3β-methyl-5α-pregnan-20-on-21-yl) thiosulfate | IP | 10 | water | 125 |
| Sodium S-[3α-hydroxy-3β-(4'-hydroxybutynyl)-5β-pregnan-20-on-21-yl] thiosulfate | IP | 10 | water | 135 |
| Sodium S-(3α-hydroxy-3β-methoxymethyl-5α-pregnan-20-on-21-yl) thiosulfate | IP | 10 | water | 126 |
| Sodium S-(3α-hydroxy-3β-trifluoromethyl-19-nor-5β-pregnan-20-on-21-yl)thiosulfate | IP | 10 | 50% hpbcd | 139 |
| 3α-hydroxy-21-(2'H-1,2,3,4-tetrazol-2'-yl)-5β-pregnan-20-one | IP | 10 | 50% hpbcd | 117 |
| 3α-Hydroxy-21-(2H-1,2,3-triazol-2-yl)-5β-pregnan-20-one | IP | 10 | 50% hpbcd | 164 |
| 3α-Hydroxy-21-[1H-(4-methyl-5-carboxyl)imidazol-1-yl)-5β-pregnan-20-one ethyl ester | IP | 10 | 50% hbpcd | 112 |
| 3α-Hydroxy-21-(1'-imidazolyl)-5α-pregnan-20-one | IP | 10 | 50% hpbcd | 141 |
| 3α-Hydroxy-21-(1'-imidazolyl)-5β-pregnan-20-one | IP | 10 | 50% hpbcd | 138 |
| 3β-Ethynyl-3α-Hydroxy-21-(1'-imidazolyl)-5β-pregnan-20-one | IP | 10 | 50% hpbcd | 179 |
| 3α-Hydroxy-21-(1H-3,5-dimethylpyrazolyl)-5β-pregnan-20-one | IP | 10 | 50% hpbcd | 128 |
| 3α-Hydroxy-21-(1'-imidazolyl)-3β-methyl-5α-pregnan-20-20-one | IP | 10 | 50% hpbcd | 144 |
| 3β-Ethynyl-3α-Hydroxy-21-(1'-pyrazolyl)-5β-pregnan-20-one | IP | 10 | 50% hpbcd | 180 |
| 3α-Hydroxy-21-(1'-pyrazolyl)-3β-methyl-5α-pregnan-20-one | IP | 10 | 50% hpbcd | 154 |
| 3α-Hydroxy-21-(pyrazol-1-yl)-5β-pregnan-20-one | IP | 10 | 50% hpbcd | 129 |
| 3α-Hydroxy-3β-methyl-21-(1',2',4'-triazolyl)-5α-pregnan-20-one | IP | 10 | 50% hpbcd | 153 |
| 3α-Hydroxy-21-(1',2',4'-triazol-1-yl)-5β-pregnan-20-one | IP | 10 | 50% hpbcd | 135 |
| 3α-Hydroxy-21-[1H-(2-methyl)imidazol-1-yl)-5β-pregnan-20-one | IP | 10 | 50% hpbcd | 96 | c) Geller-Seifter Conflict Test

This animal model of human anxiety utilizes a conditioned state of conflict in rats to ascertain the anxiolytic properties of drugs. Rats are conditioned to bar press for positive reinforcement under two schedules of behavior (Geller and Seifter, "The effects of meprobamate, barbiturates, d-amphetamine and promazine on experimentally induced conflict in the rat," Psychopharmacologia 1:482–492 (1960)). The first includes bar pressing under a variable ratio schedule without punishment. The second component is a fixed ratio schedule with each bar press resulting in a positive reinforcement and a punishment. The punished component produces a state of conflict within the animal. The unpunished component allows for the observation of any response depressant effects a drug may possess. An anxiolytic response would increase the punished responding without affecting the unpunished responding.

Male albino Sprague-Dawley rats (Charles River Labs, Wilmington, Mass.) weighing 250–300 g were used for conflict experiments and were kept on a restricted diet of Purina Lab Chow food pellets with water available at all times to maintain body weight at 85% of their free-feeding young adult levels. Rats were housed individually under a 12-hour light-dark cycle with lights on from 0700–1900.

The anti-anxiety (punishment-lessening) and response depressant effects of 3α-OH-5α-pregnan-20-one and 3α-OH-5β-pregnan-20-one were measured in rats by the conflict test of Geller and Seifter (1960). In this 63-min test, hungry rats perform a lever-press response to obtain a sweetened milk reward. The reinforcement schedule consists of punishment and nonpunishment components, alternating approximately every 15 min. Rats were trained in test chambers (Coulbourn instruments) with a lever mounted in one wall, a small dipper that delivered the 0.1-mL milk reward (1 part Eagle condensed:milk 2 parts water), and a metal grid floor through which the foot-shock punishment was administered. A DEC PDP 11/73 minicomputer running SKED (State Systems) was used for programming and recording.

Rates initially learned to respond on a continuous reinforcement schedule and progressed rapidly to 30-sec, 1-min, and 2-min variable interval (VI) schedules. On the continuous reinforcement schedule, rats received milk reward following every lever press; on the VI schedules, milk rewards were available at infrequent and variable intervals, eventually at an average of once every 2 min. Four 3-min "conflict" periods were then introduced on the unpunished VI baseline; the first started after 3 min of VI performance and the others were alternated between 12-min periods of VI responding. During conflict periods, which were signalled by the presentation of a light and a tone, the continuous reinforcement schedule was again in force and each lever press delivered both a milk reward and a brief (0.25 msec) foot-shock punishment. Shock intensity was 0.2 mA initially, and was increased daily in increments of 0.02 mA in order to gradually suppress lever pressing to 5 responses or less per conflict period. This training took 4–6 weeks, after which stable low rates of response were observed during conflict periods and stable high rates in the nonpunishment periods. Drug-induced increases in the rate of punished responses were taken as an index of antianxiety activity, while decreases in the rate of unpunished responses were taken as an index of response depression or sedation.

Figure 10:
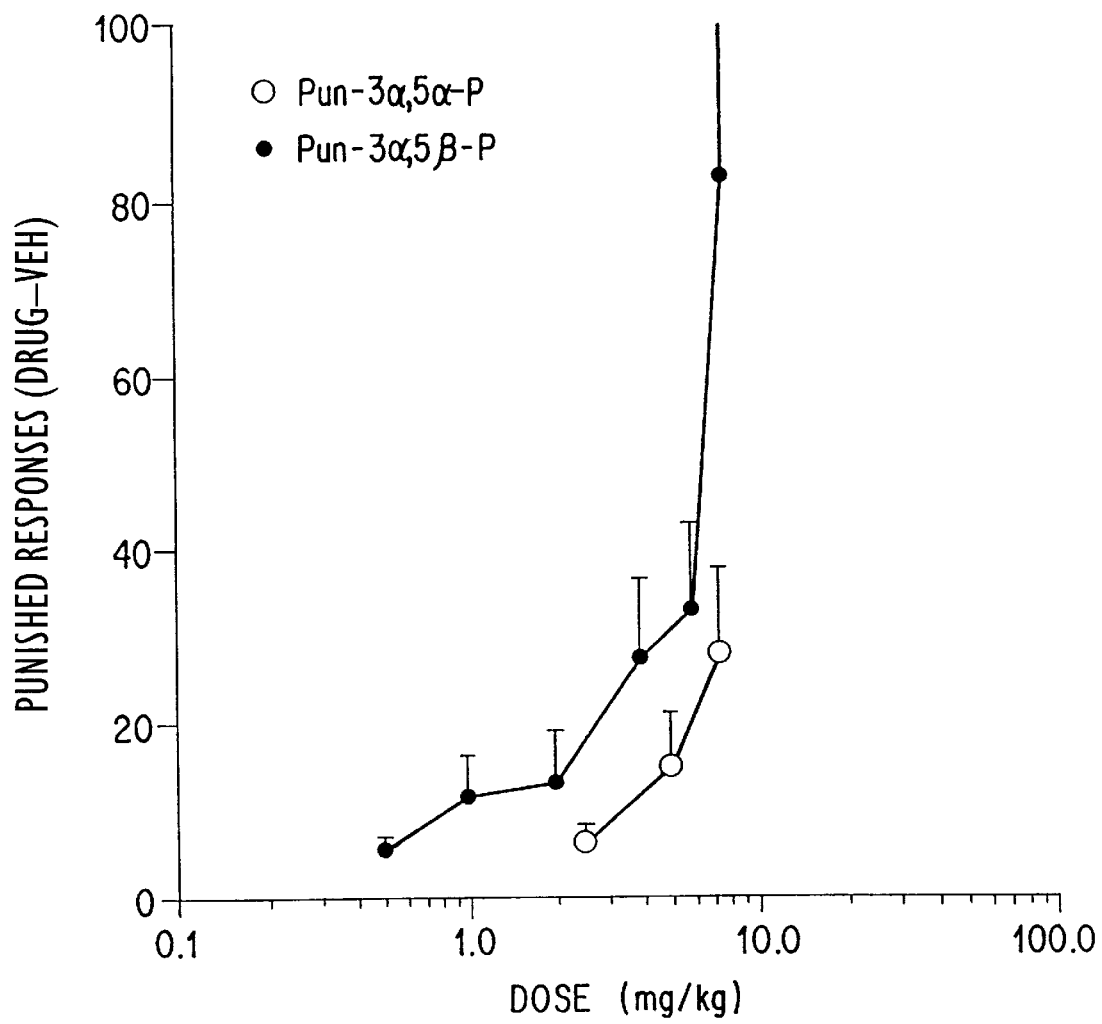
FIG. 10 is a line graph of the change in punished rats responding from baseline for 3α-OH-5α-pregnan-20-one and 3α-OH-5β-pregnan-20-one in the Geller Seifter test.

The effects of 3α-OH-5α-pregnan-20-one and 3α-OH-5β-pregnan-20-one in the conflict test are summarized in FIG. 10. Both compounds produced large increases in the rate of punished responses, suggesting that both would be active as antianxiety agents. The peak effect of 3α-OH-5β-pregnan-20-one was observed at 2 mg/kg and that of 3α-OH-5α-pregnan-20-one at 4.4 mg/kg following subcutaneous administration. (For statistical analysis and because of the small number of tests at each dose, all tests with each compound were combined for comparison against vehicle control tests, using a t-test for related measures: for 3α-OH-5α-pregnan-20-one, p<0.02; for 3α-OH-5β-pregnan-20-one, p<0.008).

Table 9 shows the summary of anxiolytic activities of compounds of and used in the invention using Geller-Seifter test under the experimental conditions described above.

TABLE 9

Anxiolytic Activity in Geller/Seifter in Rats

| Compounds | Route | Vehicle | Dose (mg/kg) | Geller/Seifter (% of control) |
|---|---|---|---|---|
| 3α-Hydroxy-3β-methoxymethyl-5α-pregnan-20-one | IP | 50% hpbcd | 10 | 958 |
| 11α-N,N-Dimethylamino-3α-hydroxy-3β-trifluoromethyl-5β-pregnan-20-one | IP | citrate | 20 | 145 |
| Sodium S-(3α-hydroxy-3β-methoxymethyl-5α-pregnan-20-on-21-yl)thiosulfate | PO | water | 32 | 4487.5 |
| 3α-hydroxy-3β-ethoxymethyl-5α-pregnan-20-one | IP | 50% hpbcd | 40 | 3743 | d) Vogel Test

The Vogel test is based on the development of a conflict between a highly motivated behavior and an aversion. For this test, the strong motivation is thirst. The animal is water deprived for 12–16 hrs to produce the motivation to drink. During the training period the animals are exposed to the testing environment so they become accustomed to the drinking spout and minimize the fear of a novel environment. Following training, the animals are allowed access to water for 2 hrs. During this time, the animals will drink and eat their normal amount of water and food, compensating for the deprivation time. However, this schedule still produces a strong motivation to drink during the testing period.

Having been deprived of water for twelve to sixteen hours, an animal is placed in a test cage where it is allowed to drink freely for five minutes. This period is used to habituate the animal to the environment and the drinking spout. Following the training period, animals have access to water and food in their home cage for 2 hrs. Food is available at all times. Twenty-four hours later, drug is administered to the animal intracerebroventricularly.

After an indicated delay started from the time of injection the animal is again placed in the test cage for ten minutes. A computer counts each time the animal licks, and after every twentieth lick administers a mild electric stimulus across the tongue and/or feet. The electrical stimulus consists of a 0.6 mA current with a duration of 100 msec. This procedure produces a state of conflict for the animal that is reduced by the administration of clinically used anxiolytic agents (i.e., Valium). For dose-response curves, separate groups of animals are injected with increasing doses of test drug and are tested at a predetermined time.

Data of representative compounds using these measurements are summarized in Table 10.

TABLE 10

Anxiolytic Activity in Vogel Test in Rats

| Compounds | Route | Vehicle | Dose (μg/kg) | Vogel (% of control) |
|---|---|---|---|---|
| 3α,20α-Dihydroxy-2β-isopropoxy-5α-pregnane | i.c.v. | g-CD | 10 | 169.0 |
| 3α,20-Dihydroxy-20-methyl-5α-pregnane | i.c.v. | g-CD | 20 | 179.0 |
| 3α,20α-Dihydroxy-21-methyl-5α-pregnane | i.c.v. | g-CD | 10 | 157.9 |
| 3α,20α(S)-Dihydroxy-5α-pregnane | i.c.v. | g-CD | 10 | 193.0 |
| 3α-Hydroxy-5α-pregnan-20-one | i.c.v. | g-CD | 10 | 431.1 |
| 3α,20α-Dihydroxy-5α-pregnane | i.c.v. | g-CD | 10 | 283.3 |
| 2β-Fluoro-3α,20α-dihydroxy-5α-pregnane | i.c.v. | g-CD | 20 | 264.9 |
| 3α,20α-Dihydroxy-21-ethyl-5α-pregnane | i.c.v. | g-CD | 20 | 225.8 |
| 3α,20α-Dihydroxy-5α-pregnane | i.c.v. | g-CD | 20 | 267.3 |

Prodrugs

Figure 11:
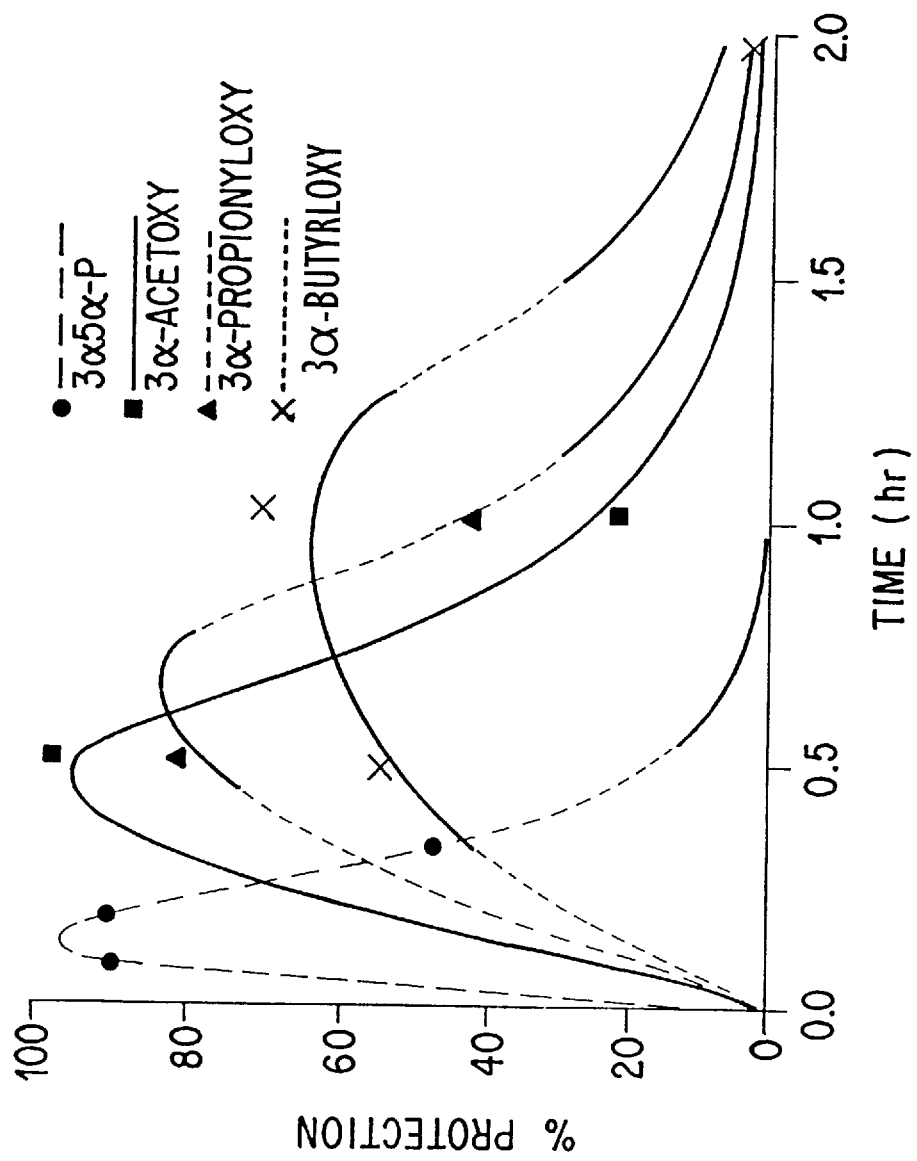
FIG. 11 is a plot of the time course of anti-metrazol activity of several prodrugs of 3α-OH-5α-pregnan-20-one.

Anti-convulsant and anxiolytic activities of prodrugs of the basic compounds 3α-hydroxy-5α-pregnan-20-one and 3α,21-dihydroxy-5α-pregnan-20-one and their derivatives were assessed as using the same procedures described above. Percent protection by several prodrugs of 3α-hydroxy-5α-pregnan-20-one against metrazol-induced seizures was plotted against time after administration of the compounds. (FIG. 11 and Table 11).

Modification of the basic compounds 3α-hydroxy-5α-pregnan-20-one and 3α,21-dihydroxy-5α-pregnan-20-one at the 3α and 21 hydroxyls with various esters maintains their biological activity and in some cases such modification increased the time of protection provided by the compound. Thus, the compounds of this invention can be modified to provide anti-convulsant and anxiolytic activities over a period of time, with varying degrees of protection.

TABLE 11

Anti-Metrazol Activity of Prodrug Esters of
3α-Hydroxy-5α-pregnane-20-one (3α-(RCOO)-5α-pregnan-20-one)

| R | % Protection 60 mg/kg 1 hr, IP |
|---|---|
| Methyl | 25 |
| Ethyl | 75 |
| Propyl | 75 |
| Butyl | 33 |
| 2-Propyl | 75 |
| 4-Heptyl | 16 (4 hour) |
| Cyclobutyl | 17 |
| Phenyl | 33 |
| 4-Chlorophenyl | 50 |
| 4-Methoxyphenyl | 17 |
| 3-Pyridyl | 50 (20 hour) |
| 3-(1-Methyl-1,4-dihydropyridinyl) | 63 (20 hour) |

In contrast to benzodiazepines, neuroactive steroids can also induce anesthesia. Their ability to induce anesthesia is thought to be due to their ability to open the chloride ion channel in the absence of GABA, which is a property not possessed by benzodiazepines. Therefore, neurosteroids can act directly in the absence of GABA, at the receptor, and also "indirectly", in the presence of GABA. This "indirect" action is called "modulating" the receptor. (Lambert, et al., "Actions of synthetic and endogenous steroids on the $GABA_A$ receptor," *Trends Pharmacology Science* 8: 224–227 (1987).)

The compounds of and used in the invention can also be used for anesthetic indications at high doses. However, the preferred route of administration to induce anesthesia is intravenous (i.v.) administration. In animals, a drug's anesthetic properties is measured by the drug's ability to produce a loss-of-righting reflex. The loss-of-righting reflex is defined as the inability of an animal to right itself within 30 seconds when placed on its back. Mice were administered drug i.v. in the lateral tail vein. Following administration, mice were placed on their backs and observed for loss-of-righting reflex. Illustrative results are presented in Table 12.

TABLE 12

Anesthetic Activity of Neuroactive Steroids in Mice

| Compounds | Route | Vehicle | Dose (mg/kg) | Loss-of-Righting Reflex |
|---|---|---|---|---|
| 3α,21-Dihydroxy-3β-ethynyl-5β-pregnan-20-one | iv | 20% cremophor | 10 | 100 |
| 3β-(Chloroethynyl)-3α-hydroxy-5β-pregnan-20-one | iv | micronizing solution | 20 | 100 |
| 3β-Ethynyl-3α-hydroxy-5β-pregnan-20-one | iv | 10% hpbcd | 30 | 100 |
| 3α-Hydroxy-3β-methyl-5α-pregn-16-en-20-one | iv | micronizing solution | 50 | 100 |
| 3α-Hydroxy-5α-pregn-9-en-20-one | iv | micronizing solution | 10 | 100 |
| 3α-Hydroxy-17(Z)-methoxymethylene-19-nor-5α-androstane | iv | micronizing solution | 5 | 75 |
| 3α-Hydroxy-3β-methyl-5β-pregnan-20-one | iv | micronizing solution | 2.5 | 100 |
| 2β-Ethoxy-3α-hydroxy-5α-pregnan-20-one | iv | 20% cremophor | 5 | 100 |
| 2β-Fluoro-3α-hydroxy-5α-pregnan-20-one | iv | micronizing solution | 5 | 100 |

TABLE 12-continued

Anesthetic Activity of Neuroactive Steroids in Mice

| Compounds | Route | Vehicle | Dose (mg/kg) | Loss-of-Righting Reflex |
|---|---|---|---|---|
| 3α-Hydroxy-3β-methyl-21-methoxymethyl-5α-pregnan-20-one | iv | micronizing solution | 20 | 100 |

It is anticipated that prodrugs, with similar modifications as described above, of compounds of and used in the invention will have activity as prodrugs of 3α-hydroxy-5-reduced-pregnanes.

While the preferred embodiments have been described and illustrated, various substitutions and modifications may be made thereto without departing from the scope of the invention. Accordingly, it is to be understood that the present invention has been described by way of illustration and not limitation.

What is claimed is:

1. A compound of the formula:

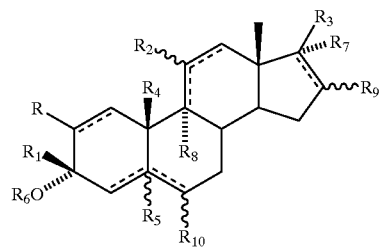

wherein:

R is hydrogen, halogen, lower alkoxy, alkyl, optionally substituted 1-alkynyl or substituted alkyl;

$R_1$ is a substituted aralkynyl, arylalkyl, arylalkenyl, aryl, optionally substituted aralkylalkynyl, alkanoyloxyalkynyl, optionally substituted heteroaryloxyalkynyl, oxoalkynyl or a ketal thereof, cyanoalkynyl, optionally substituted heteroarylalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl;

$R_2$ is hydrogen, hydroxy, alkoxy, alkanoyloxy, carbalkoxyl, a keto group or amino group;

$R_3$ is an acetyl group, a ketal of an acetyl group; an alkoxyacetyl group, an alkylthioacetyl group, an alkylsulfinylacetyl group, an alkylsulfonylacetyl group, an aminoacetyl group, a trifluoroacetyl group; a hydroxyacetyl group; an alkoxyalkylacetyl group; a hydroxyalkyl group; a hydroxyacetyl dioic acid hemi-ester salt; an alkanoyloxyacetyl group; a sulfoxyacetyl group; an alkylacetyl group; a haloacetyl group; an ethynyl group; an optionally substituted heteroaralkylacetyl group which may also optionally be substituted on the alkylene with a hydroxy, alkoxy, alkanoyloxy or carbalkoxyl group; an optionally substituted heterocyclic-acetyl group; an acetyl thiosulfate salt; a cyano group; a methylene group (together with $R_7$); an alkylmethylene group (together with $R_7$); or an alkoxymethylene group (together with $R_7$);

$R_4$ is hydrogen or methyl, $R_5$ is hydrogen;

$R_6$ is hydrogen, alkanoyl, aminocarbonyl or alkoxycarbonyl;

$R_7$ is hydrogen, halogen, hydroxy, alkoxy, alkanoyloxy, carbalkoxyl, a methylene group (together with $R_3$), or an alkoxymethylene group (together with $R_3$);

$R_8$ is hydrogen or halogen;

$R_9$ is hydrogen, halogen, alkyl, alkoxy, arylalkoxy or amino; and $R_{10}$ is hydrogen, halogen; alkyl, haloalkyl, hydroxy, alkoxy, alkanoyloxy, carbalkoxyl, cyano, thiocyano or mercapto;

with the proviso that when $R_3$ is an acetylthiosulfate salt or when R is an optionally substituted 1-alkynyl group, then $R_1$ may further be hydrogen, alkyl, alkenyl, aryl, aralkyl, alkynyl, optionally substituted aralkynyl, alkoxyalkyl, aminoalkyl, cyano, cyanoalkyl, thiocyanoalkyl, or azidoalkyl;

or a physiologically acceptable 3-ester, 20-ester, 21-ester, 3,20-diester, or 3,21-diester thereof.

2. A compound of claim 1, wherein $R_3$ is an acetyl thiosulfate salt.

3. A compound of claim 2 which is sodium S-(3α-hydroxy-5α-pregnan-20-on-21-yl)thiosulfate; sodium S-(3α-hydroxy-3β-methoxymethyl-5α-pregnan-20-on-21-yl)thiosulfate; sodium S-(3α-hydroxy-5β-pregnan-20-on-21-yl)thiosulfate; sodium S-[3α-hydroxy-3β-(4'-hydroxybutynyl)-5β-pregnan-20-on-21-yl] thiosulfate; or sodium S-(3α-hydroxy-3β-trifluoromethyl-5β-19-norpregnan-20-on-21-yl) thiosulfate.

4. A compound of claim 2 which is sodium S-(3α-hydroxy-3β-methyl-5α-pregnan-20-on-21-yl)thiosulfate.

5. A compound of the formula:

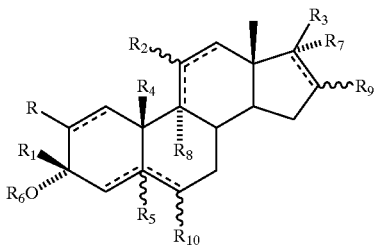

or a physiologically acceptable 3-ester, 20-ester, 21-ester, 3,20-diester, or 3,21-diester thereof; wherein:

R is hydrogen, halogen, lower alkoxy, dialkylamino, alkyl or substituted alkyl;

$R_1$ is a substituted aralkynyl, arylalkyl, arylalkenyl, optionally substituted aralkylalkynyl, alkanoyloxyalkynyl, optionally substituted heteroaryloxyalkynyl, oxoalkynyl or a ketal thereof, cyanoalkynyl, substituted heteroarylalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl;

$R_2$ is hydrogen, hydroxy, alkoxy, alkanoyloxy, carbalkoxy, a keto group or amino group;

$R_3$ is an acetyl group, a ketal of an acetyl group; an alkoxyacetyl group, an alkylthioacetyl group, an alkylsulfinylacetyl group, an alkylsulfonylacetyl group, an aminoacetyl group, a trifluoroacetyl group; a hydroxyacetyl group; an alkoxyalkylacetyl group; a hydroxyalkyl group; a hydroxyacetyl dioic acid hemi-ester salt; an alkanoyloxyacetyl group; a sulfoxyacetyl group; an alkylacetyl group; a haloacetyl group; an ethynyl group; or a cyano group; or $R_3$ together with $R_7$ is a methylene group; or $R_3$ together with $R_7$ is an alkylmethylene group; or $R_3$ together with $R_7$ is an alkoxymethylene group;

$R_4$ is hydrogen or methyl, $R_5$ is hydrogen;

$R_6$ is hydrogen, alkanoyl, aminocarbonyl or alkoxycarbonyl;

$R_7$ is hydrogen, halogen, hydroxy, alkoxy, alkanoyloxy, or carbalkoxyl, or $R_7$ together with $R_3$ is a methylene group, or $R_7$ together with $R_3$ is an alkoxymethylene group;

$R_8$ is hydrogen or halogen;

$R_9$ is hydrogen, halogen, alkyl, alkoxy, arylalkoxy or amino; and $R_{10}$ is hydrogen, halogen, alkyl, haloalkyl, hydroxy, alkoxy, alkanoyloxy, carbalkoxyl, cyano, thiocyano or mercapto.

6. The compound of claim 5, wherein the substituted aralkynyl and substituted heteroarylalkynyl groups of $R_1$ are substituted by one to five substituents selected from the group consisting of alkanoyl, carboxy, aryl, nitro, alkoxy, haloalkyl, halo, cyano, lower alkyl, halo, and —CONRR" groups, wherein R and R" are independently lower alkyl groups;

the heteroaryl of the heteroaryl-containing groups is selected from the group consisting of pyridine, oxazole, indole, purine, pyrimidine, imidazole, benzimidazole, indazole, 2H-1,2,4-triazole, 1,2,3-triazole, 2H-1,2,3,4-tetrazole, 1H-1,2,3,4-tetrazole, benzotriazole, 1,2,3-triazolo[4,5-b]pyridine, thiazole, isoxazole, pyrazole, quinoline, cytosine, thymine, uracil, adenine, guanine, pyrazine, picolinic acid, picoline, furoic acid, furfural, furyl alcohol, carbazole, 9H-pyrido[3,4-b]indole, isoquinoline, pyrrole, thiophene, furan, 9(10H)-acridone, phenoxazine and phenothiazine, and the aryl group of the aryl-containing groups is phenyl or naphthyl.

7. A compound of claim 6, wherein $R_1$ is phenylethynyl, substituted by one to five substituents selected from the group consisting of alkanoyl, carboxy or alkyl ester thereof, aryl, nitro, alkoxy, haloalkyl, halo, cyano, lower alkyl, and —CONR'R" groups, wherein R' and R" are independently lower alkyl groups.

8. A compound of claim 7, wherein said phenylethynyl is substituted by one substituent at the 4'-position.

9. A compound of claim 7, wherein said phenylethynyl is substituted by one substituent at the 3'-position or 5'-position.

10. A compound of claim 7, which is selected from the group consisting of:

3β-(4'-acetylphenylethynyl)-3β,21-dihydroxy-5α-pregnan-20-one,

3β-(4'-acetylphenyl)ethynyl-3α-hydroxy-5α-pregnan-20-one,

3β-(4'-acetylphenyl)ethynyl-3α-hydroxy-19-nor-5β-pregnan-20-one,

3β-(4'-carboxyphenyl)ethynyl-3α-hydroxy-5α-pregnan-20-one ethyl ester,

3β-(4'-carboxyphenyl)ethynyl-3α-hydroxy-5β-pregnan-20-one ethyl ester,

3β-(4'-acetylphenyl)ethynyl-3α-hydroxy-5β-pregnan-20-one,

3β-(4'-carboxyphenyl)ethynyl-3α-hydroxy-19-nor-5β-pregnan-20-one ethyl ester,

3β-(4'-acetylphenylethynyl)-3α,21-dihydroxy-5β-pregnan-20-one,

3β-(4'-biphenyl)ethynyl-3α-hydroxy-5β-pregnan-20-one,

3α-hydroxy-3β-(4'-nitrophenyl)ethynyl-5β-pregnan-20-one,

3α-hydroxy-3β-(4'-methoxyphenyl)ethynyl-5β-pregnan-20-one,

3β-(4'-trifluoromethylphenyl)ethynyl-3α-hydroxy-5β-pregnan-20-one,

3β-(4'-chlorophenyl)ethynyl-3α-hydroxy-5β-pregnan-20-one,

3β-(3'-acetylphenyl)ethynyl-3α-hydroxy-5β-pregnan-20-one,

3β-(4'-cyanophenyl)ethynyl-3α-hydroxy-5β-pregnan-20-one,

3β-(pentafluorophenyl)ethynyl-3α-hydroxy-5β-pregnan-20-one,

3β-[4'-(N,N-diethylcarboxamidophenyl)ethynyl]-3α-hydroxy-5β-pregnan-20-one, and

3α-hydroxy-3β-(4'-methylphenyl)ethynyl-5β-pregnan-20-one.

11. The compound of claim 5, wherein:

R is hydrogen, fluoro, chloro or lower alkoxy;

$R_1$ is substituted arylethynyl;

$R_2$ is hydrogen, a keto group or a dimethylamino group;

$R_3$ is a β-acetyl group, a dimethyl ketal of a β-acetyl group, a trifluoroacetyl group, a β-(hydroxyacetyl) group, a β-methoxymethylacetyl group, a β-(ethoxy)methyl-2'-methylene acetyl group, a β-(1'-hydroxyethyl) group, a β-(1'-hydroxypropyl) group, a β-(2'-hydroxy-2'propyl) group, a β-succinyloxyacetyl group, a β-hydroxyacetyl sodium succinate group, a β-acetoxyacetyl group, a β-sulfoxyacetyl group, a β-methylacetyl group, a β-haloacetyl group, or a β-ethynyl group;

$R_4$ is hydrogen or methyl;

$R_5$, $R_6$, $R_8$, $R_9$ and $R_{10}$ are hydrogen;

the dotted lines all represent single bonds; and $R_7$ is hydrogen or, when $R_3$ is β-hydroxyacetyl, $R_7$ is hydrogen or hydroxy.

12. The compound of claim 5, wherein $R_1$ is substituted arylethynyl.

13. A compound of claim 12 which is 3α-hydroxy-3β-(4'-nitrophenyl)ethynyl-5β-pregnan-20-one, 3α-hydroxy-3β-(4'-methoxyphenyl)ethynyl-5β-pregnan-20-one, 3α-hydroxy-3β-[2-(3',4'-dimethoxyphenyl)ethynyl]-5β-pregnan-20-one, 3α-hydroxy-3β-(4'-methylphenyl)ethynyl-5β-pregnan-20-one, 3β-(4'-trifluoromethylphenyl)ethynyl-3α-hydroxy-5β-pregnan-20-one, 3α-hydroxy-3β-(2'-methoxyphenyl)ethynyl-5β-pregnan-20-one, 3β-(4'-dimethylaminophenyl)ethynyl-3α-hydroxy-5β-pregnan-20-one, 3β-(4'-acetylphenyl)ethynyl-3α-hydroxy-5β-pregnan-20-one, 3β-(4'-chlorophenyl)ethynyl-3α-hydroxy-5β-pregnan-20-one, 3β-(4'-acetylphenyl)ethynyl-3α-hydroxy-5α-pregnan-20-one, 3β-(4'-carboxyphenylethynyl)-3α-hydroxy-5β-pregnan-20-one ethyl ester; 3α-hydroxy-3β-(4'-acetoxyacetylphenyl)ethynyl-5β-pregnan-20-one, or 3β-(4'-cyanophenyl)ethynyl-3α-hydroxy-5β-pregnan-20-one.

14. A compound of claim 12 which is 3β-(4'-acetylphenylethynyl)-3α-hydroxy-19-nor-5β-pregnan-20-one; 3β-(4'-carboxyphenylethynyl)-3α-hydroxy-19-nor-5β-pregnan-20-one ethyl ester; 3β-(4'-carboxyphenylethynyl)-3α-hydroxy-5α-pregnan-20-one ethyl ester; 3β-[4'-(N,N-diethylcarboxamido)phenyl]ethynyl-3α-hydroxy-5β-pregnan-20-one; 3β-(4'-acetoxyphenylethynyl)-3α-hydroxy-5β-pregnan-20-one; 3β-(4'-acetylphenylethynyl)-3α,21-dihydroxy-5α-pregnan-20-one; 3β-(4'-acetylphenylethynyl)-3α,21-dihydroxy-5β-pregnan-20-one; 3β-(4'-acetylphenylethynyl)-3α,21-dihydroxy-5α-pregnan-20-one 21-hemsuccinate salt; or 3β-(4'-acetylphenylethynyl)-3α,21-dihydroxy-5β-pregnan-20-one 21-hemsuccinate salt.

15. A compound of claim 5, wherein $R_1$ is aralkyl.

16. A compound of claim 15 which is 3α-hydroxy-3β-benzyl-5β-pregnan-20-one; 3α-hydroxy-3β-(2'-phenylethyl)-5β-pregnan-20-one; 3α-hydroxy-3β-(3'-phenylpropyl)-5β-pregnan-20-one or 3α-hydroxy-3β-[2-(3',4'-dimethoxyphenyl)ethyl]-5β-pregnan-20-one.

17. A compound of claim 5 wherein $R_1$ is cyanoalkynyl.

18. A compound of claim 17, which is 3α-hydroxy-3β-(5'-cyano-1'-pentynyl)-5β-pregnan-20-one or 3α-hydroxy-3β-(4'-cyano-1'-butynyl)-5β-pregnan-20-one.

19. A compound of claim 5, wherein $R_1$ is oxoalkynyl.

20. A compound of claim 19 which is 3α-hydroxy-3β-[6'-oxo-1'-heptynyl]-5β-pregnan-20-one; 3α-hydroxy-3β-(7'-oxo-1'-octynyl)-5β-pregnan-20-one; 3α-hydroxy-3β-(5'-oxo-1'-hexynyl)-5β-pregnan-20-one, or 3α-hydroxy-3β-(5'-oxo-1'-pentynyl)-5β-pregnan-20-one.

21. A compound of claim 5, wherein $R_1$ is hydroxyalkynyl or a physiologically acceptable ester thereof.

22. A compound of claim 21 which is 3β-(4'(R/S)-hydroxypentynyl)-3α-hydroxy-5β-pregnan-20-one, 3β-[5'-(R/S)-hydroxyhexynyl]-3α-hydroxy-5β-pregnan-20-one, 3β-(5'-hydroxy-1'-pentynyl)-3α-hydroxy-5β-pregnan-20-one, 3β-(5'-hydroxy-1'-pentynyl)-3α-hydroxy-5β-pregnan-20-one hemisuccinate sodium salt, 3β-(6'-hydroxy-1'-hexynyl)-3α-hydroxy-5β-pregnan-20-one, 3β-(6'-hydroxy-1'-hexynyl)-3α-hydroxy-5β-pregnan-20-one 6'-hemisuccinate sodium salt, 3β-(4'-hydroxy-1'-butynyl)-3α-hydroxy-5β-pregnan-20-one, 3β-(4'-hydroxy-1'-butynyl)-3α-hydroxy-5β-pregnan-20-one 4'-hemisuccinate sodium salt, 3β-(4'-hydroxy-1'-butynyl)-3α-hydroxy-5α-pregnan-20-one, 3β-(4'-hydroxy-1'-butynyl)-3α-hydroxy-5α-pregnan-20-one 4'-hemisuccinate sodium salt, 3β-(4'-hydroxy-1'-butynyl)-3α-hydroxy-5β-19-norpregnan-20-one, 3β-(4'-hydroxy-1'-butynyl)-3α-hydroxy-5β-19-norpregnan-20-one 4'-hemisuccinate sodium salt, 3β-[3'(R/S)-hydroxy-1'-butynyl]-3α-hydroxy-5α-pregnan-20-one or 3β-(3'-hydroxy-1'-propynyl)-3α-hydroxy-5β-pregnan-20-one.

23. A compound of claim 5 wherein $R_1$ is alkanoyloxyalkynyl.

24. The compound of claim 23 which is 3β-(3'-acetoxy-1'-propynyl)-3α-hydroxy-5β-pregnan-20-one; 3β-(4'-acetoxy-1'-butynyl)-3α-hydroxy-5β-pregnan-20-one; 3β-(4'-acetoxy-1'-butynyl)-3α-hydroxy-5α-pregnan-20-one; 3β-(5'-acetoxy-1'-pentynyl)-3α-hydroxy-5β-pregnan-20-one; or 3β-(6'-acetoxy-1'-hexynyl)-3α-hydroxy-5β-pregnan-20-one.

25. A compound of claim 1, wherein $R_1$ is alkynyloxyalkynyl.

26. A compound of claim 25 which is 3α-hydroxy-3β-[3-(2'-propynyloxy)-1-propynyl]-5β-pregnan-20-one.

27. A compound of claim 5, wherein $R_1$ is alkoxyalkynyl.

28. A compound of claim 27 which is 3α-hydroxy-3β-(3-methoxy-1-propynyl)-5β-pregnan-20-one or 3α-hydroxy-3β-(3-methoxy-1-propynyl)-5α-pregnan-20-one.

29. A compound of claim 5, wherein $R_1$ is heteroaryloxyalkynyl.

30. A compound of claim 29 which is 3α-hydroxy-3β-[3-(4'-pyridinyloxy)-1-propynyl]-5β-pregnan-20-one.

31. A compound of claim 5, wherein $R_1$ is substituted heteroarylalkynyl.

32. A compound of claim 31 which is 3α-hydroxy-3β-(2'-thienyl)ethynyl-5β-pregnan-20-one, 3α-hydroxy-3β-(2-pyridyl)ethynyl-5β-pregnan-20-one, 3α-hydroxy-3β-[3-(1'H-1,2,3-triazol-1'-yl)-1-propynyl]-5β-pregnan-20-one; 3α-hydroxy-3β-[3-(2'H-1,2,3-triazol-2'-yl)-1-propynyl]-5β-pregnan-20-one, 3α-hydroxy-3β-[3-(1'H-pyrazol-1'-yl)-1-propynyl]-5β-pregnan-20-one, 3α-hydroxy-3β-(5'-acetyl-2'-thienyl)ethynyl-5β-pregnan-20-one, 3α-hydroxy-3β-(3-pyridyl)ethynyl-5β-pregnan-20-one, or 3α-hydroxy-3β-(4-pyridyl)ethynyl-5β-pregnan-20-one.

33. A pharmaceutical composition comprising the compound of claim 5 and a pharmaceutically acceptable carrier.

34. A method of modulating the $GABA_A$ receptor-chloride ionophore complex in an animal subject in need of such treatment through binding to the neurosteroid site on said complex, comprising administrating to said animal subject an amount, effective to modulate said complex, of a compound of claim 5.

35. A method of treating stress or anxiety, treating mood disorders, alleviating seizure activity, insomnia, premenstrual syndrome or postnatal depression, or inducing anesthesia, comprising administering to an animal subject in need of such treatment an effective amount of the compound of claim 5.

* * * * *